US011525146B2

(12) United States Patent
Scholz

(10) Patent No.: US 11,525,146 B2
(45) Date of Patent: Dec. 13, 2022

(54) EXPRESSION CONSTRUCTS, FUSOGENIC LIPID-BASED NANOPARTICLES AND METHODS OF USE THEREOF

(71) Applicant: OISIN BIOTECHNOLOGIES, INC., Seattle, WA (US)

(72) Inventor: Matthew Rein Scholz, Seattle, WA (US)

(73) Assignee: OISIN BIOTECHNOLOGIES, INC., Seattle, WA (US)

( * ) Notice: Subject to any disclaimer, the term of this patent is extended or adjusted under 35 U.S.C. 154(b) by 437 days.

(21) Appl. No.: 16/476,865

(22) PCT Filed: Jan. 9, 2018

(86) PCT No.: PCT/US2018/013033
§ 371 (c)(1),
(2) Date: Jul. 9, 2019

(87) PCT Pub. No.: WO2018/129563
PCT Pub. Date: Jul. 12, 2018

(65) Prior Publication Data
US 2019/0330657 A1 Oct. 31, 2019

Related U.S. Application Data

(60) Provisional application No. 62/444,360, filed on Jan. 9, 2017.

(51) Int. Cl.
*C12N 15/88* (2006.01)
*A61K 48/00* (2006.01)
*A61K 9/127* (2006.01)
*C12N 15/86* (2006.01)

(52) U.S. Cl.
CPC ............ *C12N 15/88* (2013.01); *A61K 9/1271* (2013.01); *A61K 48/0025* (2013.01); *A61K 48/0058* (2013.01); *C12N 15/86* (2013.01); *C12N 2720/12043* (2013.01); *C12N 2840/007* (2013.01)

(58) Field of Classification Search
None
See application file for complete search history.

(56) References Cited

U.S. PATENT DOCUMENTS

| | | | |
|---|---|---|---|
| 5,869,337 | A | 2/1999 | Crabtree et al. |
| 9,968,076 | B2 | 5/2018 | Kirkland et al. |
| 10,098,911 | B2 | 10/2018 | Pule et al. |
| 2003/0129221 | A1 | 7/2003 | Semple et al. |
| 2004/0044185 | A1 | 3/2004 | Duncan |
| 2006/0002895 | A1 | 1/2006 | McDonnell et al. |
| 2011/0244026 | A1 | 10/2011 | Guild et al. |
| 2011/0286980 | A1 | 11/2011 | Brenner |
| 2012/0183534 | A1 | 7/2012 | Gruber |
| 2013/0150430 | A1 | 6/2013 | Croce et al. |
| 2014/0314831 | A1 | 10/2014 | Duncan et al. |
| 2015/0064137 | A1 | 3/2015 | Lichtsteiner et al. |
| 2015/0306039 | A1 | 10/2015 | Akinc et al. |
| 2015/0374842 | A1 | 12/2015 | Brown et al. |
| 2016/0010110 | A1 * | 1/2016 | Scholz ............... A61K 48/0058 424/450 |
| 2016/0166613 | A1 | 6/2016 | Spencer et al. |
| 2018/0117173 | A1 | 5/2018 | Krizhanovsky et al. |
| 2020/0009268 | A1 | 1/2020 | Scholz |

FOREIGN PATENT DOCUMENTS

| | | | |
|---|---|---|---|
| EP | 1767642 | A1 | 3/2007 |
| JP | 2002530436 | A | 9/2002 |
| WO | WO-9209298 | A1 | 6/1992 |
| WO | WO-9909191 | A1 | 2/1999 |
| WO | WO-9924582 | A1 | 5/1999 |

(Continued)

OTHER PUBLICATIONS

Alemany, R.: Chapter four-Design of improved oncolytic adenoviruses. Adv Cancer Res. 115: 93-114 (2012).
Alharbi et al.: The role of HOX genes in normal hematopoiesis and acute leukemia. Leukemia 27(5): 1000-1008 (2013).
Anesti et al.: Delivery of RNA interference triggers to sensory neurons in vivo using herpes simplex virus. Expert Opin Biol Ther. 10(1): 89-103 (2010).
Baker, et al. Clearance of p16lnk4a-positive senescent cells delays ageing-associated disorders. Nature. Nov. 2, 2011;479(7372):232-6.
Boussif et al.: Enhanced in vitro and in vivo cationic lipid-mediated gene delivery with a fluorinated glycerophosphoethanolamine helper lipid. J Gene Med. 3(2): 109-114 (2001).
Bungener et al.: Delivery of protein antigens to the immune system by fusion-active virosomes: a comparison with liposomes and ISCOMs. Biosci Rep. 22(2): 323-338 (2002).

(Continued)

*Primary Examiner* — Robert M Kelly
(74) *Attorney, Agent, or Firm* — Wilson Sonsini Goodrich & Rosati

(57) ABSTRACT

Provided nucleic acid-based expression construct for the target cell-specific production of a therapeutic protein, such as a pro-apoptotic protein, within a target cell, including a target cell that is associated with aging, disease, or other condition, in particular a target cell that is a senescent cell or a cancer cell. Also provided are formulations and systems, including fusogenic lipid nanoparticle (LNP) formulations and systems, for the delivery of nucleic acid-based expression constructs as well as methods for making and using such nucleic acid-based expression constructs, formulations, and systems for reducing, preventing, and/or eliminating the growth and/or survival of a cell, such as a senescent cell and/or a cancer cell, which is associated with aging, disease, or other condition as well as methods for the treatment of aging, disease, or other conditions by the in vivo administration of a formulation, such as a fusogenic LPN formulation, comprising an expression construct for the target cell-specific production of a therapeutic protein, such as a pro-apoptotic protein, in a target cell that is associated with aging, disease, or other condition, in particular a target cell that is a senescent cell or a cancer cell.

27 Claims, 54 Drawing Sheets

Specification includes a Sequence Listing.

(56) References Cited

FOREIGN PATENT DOCUMENTS

| | | | |
|---|---|---|---|
| WO | WO-0031238 A2 | 6/2000 | |
| WO | WO-0244206 A2 | 6/2002 | |
| WO | WO-02101076 A2 | 12/2002 | |
| WO | WO-2006043354 A1 | 4/2006 | |
| WO | WO-2008154644 A1 | 12/2008 | |
| WO | WO-2012040825 A1 | 4/2012 | |
| WO | WO-2012177927 A1 | 12/2012 | |
| WO | WO-2014160661 A2 | 10/2014 | |
| WO | WO-2015000856 A1 * | 1/2015 | ........... C12N 5/0605 |
| WO | WO-2016185481 A2 | 11/2016 | |
| WO | WO-2018129563 A1 | 7/2018 | |
| WO | WO-2019204666 A1 | 10/2019 | |
| WO | WO-2020163408 A2 | 8/2020 | |
| WO | WO-2020163408 A3 | 11/2020 | |

OTHER PUBLICATIONS

Buschmann et al. Chitosans for delivery of nucleic acids. Advanced drug delivery reviews 65.9 (2013): 1234-1270.

Campbell et al.: Increased expression of the interleukin-11 receptor and evidence of STAT3 activation in prostate carcinoma. Am J Pathol. 158(1): 25-32 (2001).

Cantile et al.: cAMP induced modifications of HOX D gene expression in prostate cells allow the identification of a chromosomal area involved in vivo with neuroendocrine differentiation of human advanced prostate cancers. J Cell Physiol. 205(2): 202-210 (2005).

Cantile et al.: HOX D13 expression across 79 tumor tissue types. Int J Cancer. 125(7): 1532-1541 (2009).

Cantile et al.: Hyperexpression of locus C genes in the HOX network is strongly associated in vivo with human bladder transitional cell carcinomas. Oncogene. 22(41): 6462-6468 (2003).

Cantile et al.: The HOX genes network in uro-genital cancers: mechanisms and potential therapeutic implications. Curr Med Chem. 18(32): 4872-4884 (2011).

Cardone et al.: Regulation of Cell Death Protease Caspase-9 by Phosphorylation. Science 282(5392): 1318-1321 (1998).

Carlotti et al.: Development of an inducible suicide gene system based on human caspase 8. Cancer Gene Ther. 12(7): 627-639 (2005).

Carrithers et al.: Enhanced susceptibility to endotoxic shock and impaired STAT3 signaling in CD31-deficient mice. Am J Pathol. 166(1): 185-196 (2005).

Chikh et al.: Liposomal delivery of CTL epitopes to dendritic cells. Biosci Rep. 22(2): 339-353 (2002).

Chung et al.: Age-related alterations in expression of apoptosis regulatory proteins and heat shock proteins in rat skeletal muscle. Biochim Biophys Acta. 1762(1):103-109 (2006).

Cillo et al.: The HOX gene network in hepatocellular carcinoma. Int J Cancer. 129(11): 2577-2587 (2011).

Clackson et al.: Redesigning an FKBP-ligand interface to generate chemical dimerizers with novel specificity. Proc Natl Acad Sci U S A. 95(18): 10437-10442 (1998).

Clevenger, C.V.: Roles and regulation of stat family transcription factors in human breast cancer. Am J Pathol. 165(5): 1449-1460 (2004).

Di Stasi et al., "Inducible apoptosis as a safety switch for adoptive cell therapy," New England Journal of Medicine, 365(18):1673-1683 (2011).

Ding et al.: Gold nanoparticles for nucleic acid delivery. Mol Ther. 22(6): 1075-1083 (2014).

Dreyer, J.: Lentiviral vector-mediated gene transfer and RNA silencing technology in neuronal dysfunctions. Mol Biotechnol. 47(2): 169-187 (2011).

Elsabahy et al.: Non-viral nucleic acid delivery: key challenges and future directions, Curr. Drug Deliv 8(3): 235-244 (2011).

Enlow et al.: Potent engineered PLGA nanoparticles by virtue of exceptionally high chemotherapeutic loadings. Nano Lett. 11(2): 808-813 (2011).

Farhood et al.: The role of dioleoyl phosphatidylethanolamine in cationic liposome mediated gene transfer. Biochim Biophys Acta. 1235(2): 289-295 (1995).

Fletcher et al.: A dialkynoyl analogue of DOPE improves gene transfer of lower-charged, cationic lipoplexes. Org Biomol Chem. 4(2): 196-199 (2006).

Fournier et al.: Comparative study of 64Cu/NOTA-[D-Tyr6,βAla11,Thi13,Nle14]BBN(6-14) monomer and dimers for prostate cancer PET imaging. EJNMMI Res. 2: 8, 15 pages total (2012).

Gagniuc et al.: Eukaryotic genomes may exhibit up to 10 generic classes of gene promoters. BMC Genomics. 13: 512, 17 pages total (2012).

Gaucheron et al.: Improved in vitro gene transfer mediated by fluorinated lipoplexes in the presence of a bile salt surfactant. J Gene Med. 3(4): 338-344 (2001).

Gaucheron et al.: In vitro cationic lipid-mediated gene delivery with fluorinated glycerophosphoethanolamine helper lipids. Bioconjug Chem. 12(6): 949-963 (2001).

Gee et al.: Overexpression of TFAP2C in invasive breast cancer correlates with a poorer response to anti-hormone therapy and reduced patient survival. J Pathol. 217(1): 32-41 (2009).

Gomes et al.: Role and regulation of the forkhead transcription factors FOXO3a and FOXM1 in carcinogenesis and drug resistance. Chin J Cancer. 32(7): 365-370 (2013).

Goodson, "Chapter 6: Dental Applications." Medical Applications of Controlled Release. 1984, vol. 2, p. 115-138.

Gratton et al.: The effect of particle design on cellular internalization pathways. Proc Natl Acad Sci U S A. 105(33): 11613-11618 (2008).

Grimm et al.: Adeno-associated virus vectors for short hairpin RNA expression. Methods Enzymol. 392: 381-405 (2005).

Gruner et al.: X-ray diffraction study of the polymorphic behavior of N-methylated dioleoylphosphatidylethanolamine. Biochemistry. 27(8): 2853-2866 (1988).

Hajitou, A.: Targeted systemic gene therapy and molecular imaging of cancer contribution of the vascular-targeted AAVP vector. Adv Genet. 69: 65-82 (2010).

Herreros-Villanueva et al.: Embryonic stem cell factors and pancreatic cancer. World J Gastroenterol . 20(9): 2247-2254 (2014).

Huang et al.: Development of hybrid viral vectors for gene therapy. Biotechnol Adv. 31(2): 208-223 (2013).

Iuliucci et al.: Intravenous safety and pharmacokinetics of a novel dimerizer drug, AP1903, in healthy volunteers. J Clin Pharmacol. 41(8): 870-879 (2001).

Jafari et al.: Nonviral approach for targeted nucleic acid delivery. Curr Med Chem. 19(2): 197-208 (2012).

Kasai et al.: DNA-based methods to prepare helper virus-free herpes amplicon vectors and versatile design of amplicon vector plasmids. Curr Gene Ther. 6(3): 303-314 (2006).

Kaufmann et al.: Virus chimeras for gene therapy, vaccination, and oncolysis: adenoviruses and beyond. Trends Mol Med. 18(7): 365-376 (2012).

Kelley et al.: YPEL3, a p53-regulated gene that induces cellular senescence. Cancer Res. 70(9): 3566-3575 (2010).

Kelly et al.: Shape-specific, monodisperse nano-molding of protein particles. J Am Chem Soc. 130(16): 5438-5439 (2008).

Kichler et al.: Influence of membrane-active peptides on lipospermine/DNA complex mediated gene transfer. Bioconjug Chern. 8(2): 213-221 (1997).

Krishnamurthy et al.: p16INK4a induces an age-dependent decline in islet regenerative potential. Nature. 443(7110): 453-457 (2006).

Li, et al., (2004). GALA: a designed synthetic pH-responsive amphipathic peptide with applications in drug and gene delivery. Adv Drug Deliv Rev, 56(7): 967-985.

Li et al.: Recent advances in delivery of drug-nucleic acid combinations for cancer treatment. J Control Release 172(2): 589-600 (2013).

Liu et al.: Activation of the apoptotic endonuclease DFF40 (caspase-activated DNase or nuclease). Oligomerization and direct interaction with histone H1. J Biol Chem. 274(20): 13836-13840 (1999) [Accessed on Oct. 1, 2020].

Liu et al.: Expression of p16(INK4a) in peripheral blood T-cells is a biomarker of human aging. Aging Cell. 8(4): 439-448 (2009).

(56) References Cited

OTHER PUBLICATIONS

Livak et al.: Analysis of relative gene expression data using real-time quantitative PCR and the 2(-Delta Delta C(T)) Method . Methods 25(4): 402-408 (2001).
Lofthouse, S.: Immunological aspects of controlled antigen delivery. Adv Drug Deliv Rev. 54(6): 863-870 (2002).
Lowe et al.: Prostate-specific expression of Bax delivered by an adenoviral vector induces apoptosis in LNCaP prostate cancer cells. Gene Ther. 8(18): 1363-1371 (2001).
Marconi et al.: HSV as a vector in vaccine development and gene therapy. Adv Exp Med Biol. 655: 118-144 (2009).
Marconi et al.: HSV as a vector in vaccine development and gene therapy. Human Vaccines 4(2): 91-105 (2008).
McCarty, D.M.: Self-complementary AAV vectors; advances and applications. Mol Ther. 16(10): 1648-1656 (2008).
Merkel et al.: Using mechanobiological mimicry of red blood cells to extend circulation times of hydrogel microparticles. Proc Natl Acad Sci USA. 108(2): 586-591 (2011).
Metselaar et al.: Liposomes for intravenous drug targeting: design and applications. Mini Rev Med Chem. 2(4): 319-329 (2002).
Midoux et al.: Chemical vectors for gene delivery: a current review on polymers, peptides and lipids containing histidine or imidazole as nucleic acids carriers. Br J Pharmacol. 157(2): 166-178 (2009).
Midoux et al.: Specific gene transfer mediated by lactosylated poly-L-lysine into hepatoma cells. Nucleic Acids Res. 21(4): 871-878 (1993).
Morgan et al.: Targeting HOX transcription factors in prostate cancer. BMC Urology 14: 17, 9 pages total (2014).
Mowa et al.: Therapeutic potential of adenoviral vectors for delivery of expressed RNAi activators. Expert Opin Drug Deliv. 7(12): 1373-1385 (2010).
Noureddine et al.: Probing the functional impact of sequence variation on p53-DNA interactions using a novel microsphere assay for protein-DNA binding with human cell extracts. PLoS Genet. 5(5):e1000462, 13 pages (2009).
O'Hagan, D.T.: Recent developments in vaccine delivery systems. Curr Drug Targets Infect Disord. 1(3): 273-286 (2001).
O'Hagan et al.: Microparticles as vaccine adjuvants and delivery systems. Expert Rev Vaccines. 2(2): 269-283 (2003).
Olsson et al.: Role of E2F3 expression in modulating cellular proliferation rate in human bladder and prostate cancer cells. Oncogene. 26(7): 1028-1037 (2007).
Parhamifar et al.: Live-cell fluorescent microscopy platforms for real-time monitoring of polyplex-cell interaction: Basic guidelines. Methods. 68(2): 300-307 (2014).
Park, Y.S.: Tumor-Directed Targeting of Liposomes. Bioscience Reports 22(2):267-281 (2002).
PCT/US2014/031638 International Search Report and Written Opinion dated Nov. 7, 2014.
PCT/US2018/013033 International Preliminary Reporton Patentability with Written Opinion dated Jul. 9, 2019.
PCT/US2018/013033 International Search Report and Written Opinion dated May 30, 2018.
Prata et al.: A new helper phospholipid for gene delivery. Chem Commun (Camb). (13): 1566, 6 pages total (2008).
Primo et al.: Lentiviral vectors for cutaneous RNA managing. Exp Dermatol . 21(3): 162-170 (2012).
Reeves et al.: Prostate cancer cells home to bone using a novel in vivo model: modulation by the integrin antagonist GLPG0187. Cancer Therapy. Int J Cancer. 136(7): 1731-1740 (2015).
Rychak et al.: Nucleic acid delivery with microbubbles and ultrasound. Adv Drug Deliv Rev. 72: 82-93 (2014).
Sakurai et al.: Effects of erythrocytes and serum proteins on lung accumulation of lipoplexes containing cholesterol or DOPE as a helper lipid in the single-pass rat lung perfusion system. Eur J Pharm Biopharm. 52(2): 165-172 (2001).
Sasaki et al.: An artificial virus-like nano carrier system: enhanced endosomal escape of nanoparticles via synergistic action of pH-sensitive fusogenic peptide derivatives. Anal Bioanal Chem. 391(8): 2717-2727 (2008).
Seo et al.: A novel method to label preformed liposomes with 64Cu for positron emission tomography (PET) imaging. Bioconjug Chem. 19(12): 2577-2584 (2008).
Shah et al.: Double-inducible gene activation system for caspase 3 and 9 in epidermis. Genesis. 45(4): 194-199 (2007).
Shariat et al.: Adenovirus-mediated transfer of inducible caspases: a novel "death switch" gene therapeutic approach to prostate cancer. Cancer Res. 61(6): 2562-2571 (2001).
Singh et al.: Recent advances in vaccine adjuvants. Pharm Res. 19(6): 715-728 (2002).
Sioud et al.: Cationic liposome-mediated delivery of siRNAs in adult mice. Biochem Biophys Res Commun. 312(4): 1220-1225 (2003).
Sizovs et al.: Precisely tunable engineering of sub-30 nm monodisperse oligonucleotide nanoparticles. J Am Chem Soc. 136(1): 234-240 (2014).
Smale, S.T.: Core promoters: active contributorsto combinatorial gene regulation. Genes Dev. 15(19): 2503-2508 (2001) [Accessed on Sep. 29, 2020].
Staunstrup et al.: Integrase-defective lentiviral vectors—a stage for nonviral integration machineries. Curr Gene Ther. 11 (5): 350-362 (2011).
Straathof et al.: An inducible caspase 9 safety switch for T-cell therapy. Blood. 105(11): 4247-4254 (2005) [Accessed on Oct. 1, 2020].
Szebeni, J.: Complement activation-related pseudoallergy: a stress reaction in blood triggered by nanomedicines and biologicals. Mol Immunol. 61(2): 163-173 (2014).
Talbot et al.: Acyl chain unsaturation and vesicle curvature alter outer leaflet packing and promote poly(ethylene glycol)-mediated membrane fusion. Biochemistry. 36(19): 5827-5836 (1997).
Thompson, C.B.: Apoptosis in the pathogenesis and treatment of disease. Science. 267(5203): 1456-1462 (1995).
Tu et al.: A fusogenic segment of glycoprotein H from herpes simplex virus enhances transfection efficiency of cationic liposomes. J Gene Med. 10(6): 646-654 (2008).
Ulrich, A.S.: Biophysical Aspects of using Liposomes as Delivery vehicles. Bioscience Reports 22(2): 129-150 (2002).
Van Deursen, Jan M. The role of senescent cells in ageing. Nature. May 22, 2014;509(7501):439-46.
Vasir et al.: Biodegradable nanoparticles for cytosolic delivery of therapeutics. Adv Drug Deliv Rev. 59(8): 718-728 (2007).
Wagner, E.: Application of membrane-active peptides for nonviral gene delivery. Adv Drug Deliv Rev. 38(3): 279-289 (1999).
Wagner et al.: Influenza virus hemagglutinin HA-2 N-terminal fusogenic peptides augment gene transfer by transferrin-polylysine-DNA complexes: toward a synthetic virus-like gene-transfer vehicle. Proc Natl Acad Sci U S A. 89(17): 7934-7938 (1992).
Wagner et al.: Progress and outlook of inorganic nanoparticles for delivery of nucleic acid sequences related to orthopedic pathologies: a review. Tissue Eng Part B Rev. 18(1): 1-14 (2012).
Wang, et al. Characterization of regulatory elements on the promoter region of p16(INK4a) that contribute to overexpression of p16 in senescent fibroblasts. J Biol Chem. Dec. 28, 2001;276(52):48655-61. Epub Oct. 11, 2001.
Wang et al.: The complex role of multivalency in nanoparticles targeting the transferrin receptor for cancer therapies. J Am Chem Soc. 132(32): 11306-11313 (2010).
Williams et al.: AP-2gamma promotes proliferation in breast tumour cells by direct repression of the CDKN1A gene. EMBO J. 28(22): 3591-3601 (2009).
Wong et al.: Lipid, sugar and liposaccharide based delivery systems. Curr Med Chem. 8(9): 1123-1136 (2001).
Wu et al.: Sp1 is Essential for p16INK4a Expression in Human Diploid Fibroblasts during Senescence. PLoS ONE 2(1):e164, 1-8 (2007).
Xie et al.: A mini review of biodegradable calcium phosphate nanoparticles for gene delivery. Curr Pharm Biotechnol. 14(10): 918-925 (2013).
Xie et al.: Adenovirus-mediated tissue-targeted expression of a caspase-9-based artificial death switch for the treatment of prostate cancer. Cancer Res. 61(18): 6795-6804 (2001).

(56) References Cited

OTHER PUBLICATIONS

Yi et al.: SIRT1 and p53, effect on cancer, senescence and beyond. Biochim Biophys Acta. 1804(8): 1684-1689 (2010).
Zhang et al.: A powerful cooperative interaction between a fusogenic peptide and lipofectamine for the enhancement of receptor-targeted, non-viral gene delivery via integrin receptors. J Gene Med. 3(6): 560-568 (2001).
Zhang et al.: Adsorption of DNA oligonucleotides by titanium dioxide nanoparticles. Langmuir. 30(3): 839-845 (2014).
Zhou et al.: Antigen Delivery to Mucosa-associated Lymphoid Tissues Using Liposomes as a Carrier. Bioscience Reports. 22(2):355-369. Apr. 2002.
Zhou et al.: Current methods for loading dendritic cells with tumor antigen for the induction of antitumor immunity. J Immunother. 25(4): 289-303 (2002).
Zhou et al.: Liposome-mediated cytoplasmic delivery of proteins: an effective means of accessing the MHC class I-restricted antigen presentation pathway. Immunomethods. 4(3): 229-235 (1994).
Nov. 15, 2018 Non-Final Office Action U.S. Appl. No. 14/862,161.
Jan. 19, 2017 Restriction Requirement U.S. Appl. No. 14/862,161.
Mar. 15, 2018 Final Office Action U.S. Appl. No. 14/862,161.
Apr. 14, 2022 Non-Final Office Action U.S. Appl. No. 16/388,775.
Jun. 17, 2019 Final Office Action U.S. Appl. No. 14/862,161.
Jul. 14, 2017 Non-Final Office Action U.S. Appl. No. 14/862,161.
Baar, et al. Targeted apoptosis of senescent cells restores tissue homeostasis in response to chemotoxicity and aging. Cell 169.1 (2017): 132-147.
Bayle, J.H., et al., "Rapamycin Analogs with Differential Binding Specificity Permit Orthogonal Control of Protein Activity", Chem. Bio, 2006, 13:99-107.
Clancy et al.: Reovirus FAST protein transmembrane domains function in a modular, primary sequence-independent manner to mediate cell-cell membrane fusion. J Virol. 83(7): 2941-2950 (2009).
Corcoran et al.: The p14 fusion-associated small transmembrane (FAST) protein effects membrane fusion from a subset of membrane microdomains. J Biol Chem. 281(42): 31778-31789 (2006).
Glinka, E., "Eukaryotic expression vectors bearing genes encoding cytotoxic proteins for cancer gene therapy", Plasmid, 68(2), pp. 69-85, May 18, 2012 (May 18, 2012).
Jensen et al.: Design of an inhalable dry powder formulation of DOTAP-modified PLGA nanoparticles loaded with siRNA. J Control Release. 157(1): 141-148 (2012).
Krabbe et al.: Fusogenic Viruses in Oncolytic Immunotherapy. Cancers (Basel). 10(7): 216, 19 pages total (2018).
Lau et al.: Oligomerization of fusogenic peptides promotes membrane fusion by enhancing membrane destabilization. Biophys J. 86(1 Pt 1): 272-284 (2004).
Li, S. et al., "In vivo gene transfer via intravenous administration of cationic lipid-protamine-DNA (LPD) complexes", Gene Therapy, 4, pp. 891-900, Sep. 1, 1997 (Sep. 1, 1997).
Mineev et al.: Structural investigation of influenza virus hemagglutinin membrane-anchoring peptide. Protein Eng Des Sei. 26(9): 547-552 (2013).
Mriouah et al.: Abstract 5143: Fusogenic targeted liposomes: novel nanotherapy for specific treatment of prostate cancer. AACR; Cancer Res 77(13 Suppl): Abstract nr 5143 (2017).
Nesbitt, R.L.: Targeted Intracellular Therapeutic Delivery Using Liposomes Formulated with Multifunctional FAST proteins. Electronic Thesis and Dissertation Repository. 388. https://ir.lib.uwo.ca/etd/388 126 pages total (2012).
PCT/US2019/028207 International Preliminary Report on Patentability with Written Opinion dated Oct. 20, 2020.
PCT/US2019/028207 International Search Report and Written Opinion dated Jul. 29, 2019.
PCT/US2020/016679 International Preliminary Report on Patentability dated Aug. 10, 2021.
PCT/US2020/016679 International Search Report and Written Opinion dated Oct. 5, 2020.
Sanchez-Garcia et al.: The fusogenic peptide HA2 impairs selectivity of CXCR4-targeted protein nanoparticles. Chem Commun (Camb). 53(33): 4565-4568 (2017).
Stavrou, M., et al., "A Rapamycin-Activated Caspase 9-Based Suicide Gene", Molecular Therapy, 2018, vol. 26, No. 5, pp. 1266-1276.
Sudo, et al. Human-derived fusogenic peptides for the intracellular delivery of proteins. J. Control. Release 255, 1-11 (2017).
Wong et al.: Expression of the fusogenic p14 FAST protein from a replication-defective adenovirus vector does not provide a therapeutic benefit in an immunocompetent mouse model of cancer. Cancer Gene Ther. 23(10): 355-364 (2016).
Zhao et al., An EBF3-Mediated Transcriptional Program That Induces Cell Cycle Arrest and Apoptosis. Cancer Research 66(19): 9445-9452 (2006).
Donehower, L. et al., "The tumor suppressor p53", Biochimica et Biophysica Acta, 1993, vol. 1155, No. 2, pp. 181-205.
Wang, S. et al., "p73 or p53 Directly Regulates Human p53 Transcription to Maintain Cell Cycle Checkpoints", Cancer Res, 2006 vol. 66, No. 14, pp. 6982-6989.

* cited by examiner

FIG. 3

| Company | Technology | Type | MTD | Clinical Development |
|---|---|---|---|---|
| Various | Lipotrust, DOTAP, others | CL | 0.045 mg/kg | Phase I (various - all terminated due to toxicity) |
| Calando/Arrowhead | RONDEL lipopolymer | CL | 0.81 mg/kg | Phase II (CALAA-01) |
| EGEN | PEG-PEI-Cholesterol Lipopolymer | CL | 0.65 mg/kg | Phase II (EGEN-001, failed due to toxicity) |
| Marina Biotech, ProNAi | Smarticles (amphoteric liposomes) | CCL | 3.2 mg/kg | Phase II (PNT2258) |
| Marina Biotech | DiLA$^2$ | CCL | 1 mg/kg | Phase I |
| Arbutus (Tekmira), Alnylam | SNALP | CCL | 0.9 mg/kg | 7 programs in Phase I and II |
| MD Anderson (Anil Sood) | DOPC liposomes | NL | >10 mg/kg | Phase I (siRNA-DOPC-EphA2) |
| innovascreen | *Fusogenix LNPs* | *NL* | *>15 mg/kg* | *Estimated from rat toxicity study* |

Homodimerizer
AP1903

Homodimerizer
AP20187 pVax1-p53-iCasp9-5 (saCasp9 - M&M's Version) (GenArt 16ADG2IC_1977690)
3740 bp

Annexin V flow cytometry pVax-p53 alone pVax-p53 + AP20187

*=p<0.05, =p<0.01, *=p<0.001

SEQUENCE LISTING

```
<160> NUMBER OF SEQ ID NOS: 11

<210> SEQ ID NO 1
<211> LENGTH: 3017
<212> TYPE: DNA
<213> ORGANISM: Homo sapiens

<400> SEQUENCE: 1

ttcagagaaa tccctgaatt cactgaaagt tttatctaga aatacatgtg caagtgaaca     60

catctttttt aaaaaaaatc attacctact ttcttttttg agaagaaggt atttatttca    120

acagactctt gaaggagcct actcttccca ctctcccacc cccattaaga accactgtag    180

gccgggcacg atggctcatg cctgtaatcc cagcactttg ggaggctaag gtgggtggat    240

cacctgaggt caggagttcg agacaagcct agccaacata gtgaaacccc gtctctacta    300

ataatacaaa aattagctgg gtatggcagc atgtgcctgt aatcccagct actcgggagg    360

ctgaggcagg agaattgctc gaacccggga ggcggaggtt gcagtgaacc gagagagatc    420

gtgcggtgcc atttcactcc agcctgggca acagagcgaa actccatctc aaaaaaacac    480

acaaaacaaa caaacaaaaa gaaagaacca ttgtattagt gatggaaatg tgttccctcc    540

ctcccatcct ggcaaccact ttcttcctcc tccatcataa aatatcttaa actaaactaa    600

aataatttta tttatcgata gtttgaattt tccctatcat tgctacacag ctaattgaga    660

ggtaccccga ggaaaatata aatggtacag taatgcattg tagattttaa taacatactt    720

gacatcccaa attgttttca ttggcttcat tttaaaaact acatgtttta aaatcaagca    780

gacactaaaa gtacaagata tactgggtct acaaggttta agtcaaccag ggattgaaat    840

ataacttttta aacagagctg gattatccag taggcagatt aagcatgtgc ttaaggcatc    900

agcaaagtct gagcaatcca ttttttaaaa cgtagtacat gtttttgata agcttaaaaa    960

gtagtagtca caggaaaaat tagaactttt acctccttgc gcttgttata ctctttagtg   1020

ctgtttaact ttctttgta agtgagggtg gtggagggtg cccataatct tttcagggag   1080

taagttcttc ttggtctttc tttctttctt tctttctttt tttcttgaga ccaagtttcg   1140

ctcttgtctc ccaggctgga gtgcaatggc gcgatctcgg ctcactgcaa cctccgcctt   1200

ctcctgggtt caagcgattc tcctacatca gcctccgagt agctgggatt acaggcatgc   1260

gccaccaagc cccgctaatt ttgtattttt tagtagagac agggtttcgc catgttggtc   1320

aggcttgtct cgaactcctg gcctcaggtg atccgcctgt ctcggcctcc cagaatgctg   1380
```

-continued

```
ggattataga cgtgagccac cgcatccgga ctttcctttt atgtaatagt gataattcta   1440

tccaaagcat ttttttttt ttttttgagt cggagtctca ttctgtcacc caggctggag   1500

ggtggtggcg cgatctcggc ttactgcaac ctctgcctcc cgggttcaag cgattctcct   1560

gcctcagcct cctgagtagc tggaattaca cacgtgcgcc accatggcca gctaattttt   1620

gtatttttag tagagacggg gtgtcaccat tttggccaag ctggcctcga actcctgacc   1680

tcaggtgatc tgcccgcctc ggcttcccaa agtgctggga ttacaggtgt gagccaccgc   1740

gtcctgctcc aaagcatttt ctttctatgc ctcaaaacaa gattgcaagc cagtcctcaa   1800

agcggataat tcaagagcta acaggtatta gcttaggatg tgtggcactg ttcttaaggc   1860

ttatatgtat taatacatca tttaaactca caacaacccc tataaagcag ggggcactca   1920

tattcccttc cccctttata attacgaaaa atgcaaggta ttttcagtag gaaagagaaa   1980

tgtgagaagt gtgaaggaga caggacagta tttgaagctg gtctttggat cactgtgcaa   2040

ctctgcttct agaacactga gcactttttc tggtctagga attatgactt tgagaatgga   2100

gtccgtcctt ccaatgactc cctccccatt ttcctatctg cctacaggca gaattctccc   2160

ccgtccgtat taaataaacc tcatcttttc agagtctgct cttataccag gcaatgtaca   2220

cgtctgagaa acccttgccc cagacagccg ttttacacgc aggaggggaa ggggaggggga   2280

aggagagagc agtccgactc tccaaaagga atcctttgaa ctagggtttc tgacttagtg   2340

aaccccgcgc tcctgaaaat caagggttga gggggtaggg ggacactttc tagtcgtaca   2400

ggtgatttcg attctcggtg gggctctcac aactaggaaa gaatagtttt gctttttctt   2460

atgattaaaa gaagaagcca tactttccct atgacaccaa acaccccgat tcaatttggc   2520

agttaggaag gttgtatcgc ggaggaagga aacggggcgg gggcggattt ctttttaaca   2580

gagtgaacgc actcaaacac gcctttgctg gcaggcgggg gagcgcggct gggagcaggg   2640

aggccggagg gcggtgtggg gggcaggtgg ggaggagccc agtcctcctt ccttgccaac   2700

gctggctctg gcgagggctg cttccggctg gtgcccccgg gggagaccca acctggggcg   2760

acttcagggg tgccacattc gctaagtgct cggagttaat agcacctcct ccgagcactc   2820

gctcacggcg tccccttgcc tggaaagata ccgcggtccc tccagaggat ttgagggaca   2880

gggtcggagg gggctcttcc gccagcaccg gaggaagaaa gaggaggggc tggctggtca   2940

ccagagggtg gggcggaccg cgtgcgctcg gcggctgcgg agagggggag agcaggcagc   3000

gggcggcggg gagcagc                                                  3017


<210> SEQ ID NO 2
<211> LENGTH: 20
<212> TYPE: DNA
<213> ORGANISM: Homo sapiens

<400> SEQUENCE: 2

gggcatgtcc gggcatgtcc                                                 20


<210> SEQ ID NO 3
<211> LENGTH: 1251
<212> TYPE: DNA
<213> ORGANISM: Homo sapiens

<400> SEQUENCE: 3

atggacgaag cggatcggcg gctcctgcgg cggtgccggc tgcggctggt ggaagagctg     60

caggtggacc agctctggga cgccctgctg agccgcgagc tgttcaggcc ccatatgatc    120
```

-continued gaggacatcc agcgggcagg ctctggatct cggcgggatc aggccaggca gctgatcata 180
gatctggaga ctcgagggag tcaggctctt cctttgttca tctcctgctt agaggacaca 240
ggccaggaca tgctggcttc gtttctgcga actaacaggc aagcagcaaa gttgtcgaag 300
ccaaccctag aaaaccttac cccagtggtg ctcagaccag agattcgcaa accagaggtt 360
ctcagaccgg aaacacccag accagtggac attggttctg gaggatttgg tgatgtcggt 420
gctcttgaga gtttgagggg aaatgcagat ttggcttaca tcctgagcat ggagccctgt 480
ggccactgcc tcattatcaa caatgtgaac ttctgccgtg agtccgggct ccgcacccgc 540
actggctcca acatcgactg tgagaagttg cggcgtcgct tctcctcgct gcatttcatg 600
gtggaggtga agggcgacct gactgccaag aaaatggtgc tggctttgct ggagctggcg 660
cagcaggacc acggtgctct ggactgctgc gtggtggtca ttctctctca cggctgtcag 720
gccagccacc tgcagttccc aggggctgtc tacggcacag atggatgccc tgtgtcggtc 780
gagaagattg tgaacatctt caatgggacc agctgcccca gcctgggagg gaagcccaag 840
ctctttttca tccaggcctg tggtggggag cagaaagacc atgggtttga ggtggcctcc 900
acttcccctg aagacgagtc ccctggcagt aaccccgagc cagatgccac cccgttccag 960
gaaggtttga ggaccttcga ccagctggac gccatatcta gtttgcccac acccagtgac 1020
atctttgtgt cctactctac tttcccaggt tttgtttcct ggagggaccc caagagtggc 1080
tcctggtacg ttgagaccct ggacgacatc tttgagcagt gggctcactc tgaagacctg 1140
cagtccctcc tgcttagggt cgctaatgct gtttcggtga aagggattta taaacagatg 1200
cctggttgct ttaatttcct ccggaaaaaa cttttcttta aaacatcata a 1251

<210> SEQ ID NO 4
<211> LENGTH: 834
<212> TYPE: DNA
<213> ORGANISM: Homo sapiens

<400> SEQUENCE: 4
atggagaaca ctgaaaactc agtggattca aaatccatta aaaatttgga accaaagatc 60
atacatggaa gcgaatcaat ggactctgga atatccctgg acaacagtta taaaatggat 120
tatcctgaga tgggtttatg tataataatt aataataaga attttcataa aagcactgga 180
atgacatctc ggtctggtac agatgtcgat gcagcaaacc tcagggaaac attcagaaac 240
ttgaaatatg aagtcaggaa taaaaatgat cttacacgtg aagaaattgt ggaattgatg 300
cgtgatgttt ctaaagaaga tcacagcaaa aggagcagtt ttgtttgtgt gcttctgagc 360
catggtgaag aaggaataat tttggaaca aatggacctg ttgacctgaa aaaaataaca 420
aactttttca gaggggatcg ttgtagaagt ctaactggaa aacccaaact tttcattatt 480
caggcctgcc gtggtacaga actggactgt ggcattgaga cagacagtgg tgttgatgat 540
gacatggcgt gtcataaaat accagtggag gccgacttct tgtatgcata ctccacagca 600
cctggttatt attcttggcg aaattcaaag gatggctcct ggttcatcca gtcgctttgt 660
gccatgctga aacagtatgc cgacaagctt gaatttatgc acattcttac ccgggttaac 720
cgaaaggtgg caacagaatt tgagtccttt tcctttgacg ctacttttca tgcaaagaaa 780
cagattccat gtattgtttc catgctcaca aaagaactct atttttatca ctaa 834

<210> SEQ ID NO 5
<211> LENGTH: 1089
<212> TYPE: DNA
<213> ORGANISM: Homo sapiens -continued

<400> SEQUENCE: 5

```
atgctccaga agcccaagag cgtgaagctg cgggccctgc gcagcccgag gaagttcggc      60
gtggctggcc ggagctgcca ggaggtgctg cgcaagggct gtctccgctt ccagctccct     120
gagcgcggtt cccggctgtg cctgtacgag gatggcacgg agctgacgga agattacttc     180
cccagtgttc ccgacaacgc cgagctggtg ctgctcacct tgggccaggc ctggcagggc     240
tgtgagtggc aaggactttg gaggatgtgt cttctgctgg accggcacct tttgtttgtc     300
ccattggtgg cagatgtgag cgacatcagg cgcttcctca gtgcatttca cgagccacag     360
gtggggctca tccaggccgc ccagcagctg ctgtgtgatg agcaggcccc acagaggcag     420
aggctgctgg ctgacctcct gcacaacgtc agccagaaca tcgcggccga gacccgggct     480
gaggacccgc cgtggtttga aggcttggag tcccgatttc agagcaagtc tggctatctg     540
agatacagct gtgagagccg gatccggagt tacctgaggg aggtgagctc ctacccctcc     600
acggtgggtg cggaggctca ggaggaattc ctgcgggtcc tcggctccat gtgccagagg     660
ctccggtcca tgcagtacaa tggcagctac ttcgacagag gagccaaggg cggcagccgc     720
ctctgcacac cggaaggctg gttctcctgc cagggtccct ttgacatgga cagctgctta     780
tcaagacact ccatcaaccc ctacagtaac agggagagca ggatcctctt cagcacctgg     840
aacctggatc acataataga aaagaaacgc accatcattc ctacactggt ggaagcaatt     900
aaggaacaag atggaagaga agtggactgg gagtattttt atggcctgct ttttacctca     960
gagaacctaa aactagtgca cattgtctgc cataagaaaa ccacccacaa gctcaactgt    1020
gacccaagca gaatctacaa accccagaca aggttgaagc ggaagcagcc tgtgcggaaa    1080
cgccagtga                                                            1089
```

<210> SEQ ID NO 6
<211> LENGTH: 4198
<212> TYPE: DNA
<213> ORGANISM: Homo sapiens

<400> SEQUENCE: 6

```
gactcttcgc gatgtacggg ccagatatac gcgtacaggt gatttcgatt ctcggtgggg      60
ctctcacaac taggaaagaa tagttttgct tttcttatg attaaaagaa gaagccatac     120
tttccctatg acaccaaaca ccccgattca atttggcagt taggaaggtt gtatcgcgga     180
ggaaggaaac ggggcggggg cggatttctt tttaacagag tgaacgcact caaacacgcc     240
tttgctggca ggcgggggag cgcggctggg agcagggagg ccggagggcg gtgtgggggg     300
caggtgggga ggagcccagt cctccttcct tgccaacgct ggctctggcg agggctgctt     360
ccggctggtg cccccggggg agacccaacc tggggcgact tcaggggtgc cacattcgct     420
aagtgctcgg agttaatagc acctcctccg agcactcgct cacggcgtcc ccttgcctgg     480
aaagataccg cggtccctcc agaggatttg agggacaggg tcggaggggg ctcttccgcc     540
agcaccggag gaagaaagag gaggggctgg ctggtcacca gagggtgggg cggaccgcgt     600
gcgctcggcg gctgcggaga gggggagagc aggcagcggg cggcggggag cagctctggc     660
taactagaga acccactgct tactggctta tcgaaattaa tacgactcac tatagggaga     720
cccaagctgg ctagcatgct cgagggagtg caggtggaaa ccatctcccc aggagacggg     780
cgcaccttcc ccaagcgcgg ccagacctgc gtggtgcact acaccgggat gcttgaagat     840
ggaaagaaag ttgattcctc ccgggacaga aacaagccct ttaagtttat gctaggcaag     900
```

-continued

```
caggaggtga tccgaggctg ggaagaaggg gttgcccaga tgagtgtggg tcagagagcc    960
aaactgacta tatctccaga ttatgcctat ggtgccactg ggcacccagg catcatccca   1020
ccacatgcca ctctcgtctt cgatgtggag cttctaaaac tggaatctgg cggtggatcc   1080
ggagtcgacg gatttggtga tgtcggtgct cttgagagtt tgaggggaaa tgcagatttg   1140
gcttacatcc tgagcatgga gccctgtggc cactgcctca ttatcaacaa tgtgaacttc   1200
tgccgtgagt ccgggctccg cacccgcact ggctccaaca tcgactgtga gaagttgcgg   1260
cgtcgcttct cctcgctgca tttcatggtg gaggtgaagg gcgacctgac tgccaagaaa   1320
atggtgctgg ctttgctgga gctggcgcag caggaccacg gtgctctgga ctgctgcgtg   1380
gtggtcattc tctctcacgg ctgtcaggcc agccacctgc agttcccagg ggctgtctac   1440
ggcacagatg gatgccctgt gtcggtcgag aagattgtga acatcttcaa tgggaccagc   1500
tgccccagcc tgggagggaa gcccaagctc tttttcatcc aggcctgtgg tggggagcag   1560
aaagaccatg ggtttgaggt ggcctccact tcccctgaag acgagtcccc tggcagtaac   1620
cccgagccag atgccacccc gttccaggaa ggtttgagga ccttcgacca gctggacgcc   1680
atatctagtt tgcccacacc cagtgacatc tttgtgtcct actctacttt cccaggtttt   1740
gtttcctgga gggaccccaa gagtggctcc tggtacgttg agaccctgga cgacatcttt   1800
gagcagtggg ctcactctga agacctgcag tccctcctgc ttagggtcgc taatgctgtt   1860
tcggtgaaag ggatttataa acagatgcct ggttgcttta atttcctccg gaaaaaactt   1920
ttctttaaaa catcagtcga ctatccgtac gacgtaccag actacgcact cgactaagcg   1980
gccgctcgag tctagagggc ccgtttaaac ccgctgatca gcctcgactg tgccttctag   2040
ttgccagcca tctgttgttt gcccctcccc cgtgccttcc ttgaccctgg aaggtgccac   2100
tcccactgtc ctttcctaat aaaatgagga aattgcatcg cattgtctga gtaggtgtca   2160
ttctattctg gggggtgggg tggggcagga cagcaagggg gaggattggg aagacaatag   2220
caggcatgct ggggatgcgg tgggctctat ggcttctact gggcggtttt atggacagca   2280
agcgaaccgg aattgccagc tggggcgccc tctggtaagg ttgggaagcc ctgcaaagta   2340
aactggatgg ctttctcgcc gccaaggatc tgatggcgca ggggatcaag ctctgatcaa   2400
gagacaggat gaggatcgtt tcgcatgatt gaacaagatg gattgcacgc aggttctccg   2460
gccgcttggg tggagaggct attcggctat gactgggcac aacagacaat cggctgctct   2520
gatgccgccg tgttccggct gtcagcgcag gggcgcccgg ttctttttgt caagaccgac   2580
ctgtccggtg ccctgaatga actgcaagac gaggcagcgc ggctatcgtg gctggccacg   2640
acgggcgttc cttgcgcagc tgtgctcgac gttgtcactg aagcgggaag ggactggctg   2700
ctattgggcg aagtgccggg gcaggatctc ctgtcatctc accttgctcc tgccgagaaa   2760
gtatccatca tggctgatgc aatgcggcgg ctgcatacgc ttgatccggc tacctgccca   2820
ttcgaccacc aagcgaaaca tcgcatcgag cgagcacgta ctcggatgga agccggtctt   2880
gtcgatcagg atgatctgga cgaagagcat caggggctcg cgccagccga actgttcgcc   2940
aggctcaagg cgagcatgcc cgacggcgag gatctcgtcg tgacccatgg cgatgcctgc   3000
ttgccgaata tcatggtgga aaatggccgc ttttctggat tcatcgactg tggccggctg   3060
ggtgtggcgg accgctatca ggacatagcg ttggctaccc gtgatattgc tgaagagctt   3120
ggcggcgaat gggctgaccg cttcctcgtg ctttacggta tcgccgctcc cgattcgcag   3180
cgcatcgcct tctatcgcct tcttgacgag ttcttctgaa ttattaacgc ttacaatttc   3240
ctgatgcggt attttctcct tacgcatctg tgcggtattt cacaccgcat acaggtggca   3300
```

```
cttttcgggg aaatgtgcgc ggaacccta tttgtttatt tttctaaata cattcaaata   3360

tgtatccgct catgagacaa taaccctgat aaatgcttca ataatagcac gtgctaaaac   3420

ttcattttta atttaaaagg atctaggtga agatcctttt tgataatctc atgaccaaaa   3480

tcccttaacg tgagttttcg ttccactgag cgtcagaccc cgtagaaaag atcaaaggat   3540

cttcttgaga tccttttttt ctgcgcgtaa tctgctgctt gcaaacaaaa aaaccaccgc   3600

taccagcggt ggtttgtttg ccggatcaag agctaccaac tctttttccg aaggtaactg   3660

gcttcagcag agcgcagata ccaaatactg tccttctagt gtagccgtag ttaggccacc   3720

acttcaagaa ctctgtagca ccgcctacat acctcgctct gctaatcctg ttaccagtgg   3780

ctgctgccag tggcgataag tcgtgtctta ccgggttgga ctcaagacga tagttaccgg   3840

ataaggcgca gcggtcgggc tgaacggggg gttcgtgcac acagcccagc ttggagcgaa   3900

cgacctacac cgaactgaga tacctacagc gtgagctatg agaaagcgcc acgcttcccg   3960

aagggagaaa ggcggacagg tatccggtaa gcggcagggt cggaacagga gagcgcacga   4020

gggagcttcc agggggaaac gcctggtatc tttatagtcc tgtcgggttt cgccacctct   4080

gacttgagcg tcgatttttg tgatgctcgt caggggggcg gagcctatgg aaaaacgcca   4140

gcaacgcggc ctttttacgg ttcctgggct tttgctggcc ttttgctcac atgttctt     4198
```

<210> SEQ ID NO 7
<211> LENGTH: 3797
<212> TYPE: DNA
<213> ORGANISM: Homo sapiens

<400> SEQUENCE: 7

```
gactcttcgc gatgtacggg ccagatatac gcttgtcatg gcgactgtcc agctttgtgc     60

caggagcctc gcaggggttg atgggattgg ggtttcccc tcccatgtgc tcaagactgg    120

cgctaaaagt tttgagcttc tcaaaagtct agagccaccg tccagggagc aggtagctgc    180

tgggctccgg ggacactttg cgttcgggct gggagcgtgc tttccacgac ggtgacacgc    240

ttccctggat tggtctggct aactagagaa cccactgctt actggcttat cgaaattaat    300

acgactcact atagggagac ccaagctggc tagcatgctc gagggagtgc aggtggaaac    360

catctcccca ggagacgggc gcaccttccc caagcgcggc cagacctgcg tggtgcacta    420

caccgggatg cttgaagatg gaaagaaagt tgattcctcc cgggacagaa acaagccctt    480

taagtttatg ctaggcaagc aggaggtgat ccgaggctgg gaagaagggg ttgcccagat    540

gagtgtgggt cagagagcca aactgactat atctccagat tatgcctatg gtgccactgg    600

gcacccaggc atcatcccac cacatgccac tctcgtcttc gatgtggagc ttctaaaact    660

ggaatctggc ggtggatccg gagtcgacgg atttggtgat gtcggtgctc ttgagagttt    720

gaggggaaat gcagatttgg cttacatcct gagcatggag ccctgtggcc actgcctcat    780

tatcaacaat gtgaacttct gccgtgagtc cgggctccgc acccgcactg gctccaacat    840

cgactgtgag aagttgcggc gtcgcttctc ctcgctgcat ttcatggtgg aggtgaaggg    900

cgacctgact gccaagaaaa tggtgctggc tttgctggag ctggcgcagc aggaccacgg    960

tgctctggac tgctgcgtgg tggtcattct ctctcacggc tgtcaggcca gccacctgca   1020

gttcccaggg gctgtctacg gcacagatgg atgccctgtg tcggtcgaga agattgtgaa   1080

catcttcaat gggaccagct gccccagcct gggagggaag cccaagctct tttcatcca    1140

ggcctgtggt ggggagcaga aagaccatgg gtttgaggtg gcctccactt cccctgaaga   1200
```

-continued

```
cgagtcccct ggcagtaacc ccgagccaga tgccaccccg ttccaggaag gtttgaggac   1260
cttcgaccag ctggacgcca tatctagttt gcccacaccc agtgacatct ttgtgtccta   1320
ctctactttc ccaggttttg tttcctggag ggaccccaag agtggctcct ggtacgttga   1380
gaccctggac gacatctttg agcagtgggc tcactctgaa gacctgcagt ccctcctgct   1440
tagggtcgct aatgctgttt cggtgaaagg gatttataaa cagatgcctg gttgctttaa   1500
tttcctccgg aaaaaacttt tctttaaaac atcagtcgac tatccgtacg acgtaccaga   1560
ctacgcactc gactaagcgg ccgctcgagt ctagagggcc cgtttaaacc cgctgatcag   1620
cctcgactgt gccttctagt tgccagccat ctgttgtttg cccctccccc gtgccttcct   1680
tgaccctgga aggtgccact cccactgtcc tttcctaata aaatgaggaa attgcatcgc   1740
attgtctgag taggtgtcat tctattctgg ggggtggggt ggggcaggac agcaaggggg   1800
aggattggga agacaatagc aggcatgctg gggatgcggt gggctctatg gcttctactg   1860
ggcggtttta tggacagcaa gcgaaccgga attgccagct ggggcgccct ctggtaaggt   1920
tgggaagccc tgcaaagtaa actggatggc tttctcgccg ccaaggatct gatggcgcag   1980
gggatcaagc tctgatcaag agacaggatg aggatcgttt cgcatgattg aacaagatgg   2040
attgcacgca ggttctccgg ccgcttgggt ggagaggcta ttcggctatg actgggcaca   2100
acagacaatc ggctgctctg atgccgccgt gttccggctg tcagcgcagg ggcgcccggt   2160
tctttttgtc aagaccgacc tgtccggtgc cctgaatgaa ctgcaagacg aggcagcgcg   2220
gctatcgtgg ctggccacga cgggcgttcc ttgcgcagct gtgctcgacg ttgtcactga   2280
agcgggaagg gactggctgc tattgggcga agtgccgggg caggatctcc tgtcatctca   2340
ccttgctcct gccgagaaag tatccatcat ggctgatgca atgcggcggc tgcatacgct   2400
tgatccggct acctgcccat tcgaccacca agcgaaacat cgcatcgagc gagcacgtac   2460
tcggatggaa gccggtcttg tcgatcagga tgatctggac gaagagcatc aggggctcgc   2520
gccagccgaa ctgttcgcca ggctcaaggc gagcatgccc gacggcgagg atctcgtcgt   2580
gacccatggc gatgcctgct tgccgaatat catggtggaa aatggccgct tttctggatt   2640
catcgactgt ggccggctgg gtgtggcgga ccgctatcag gacatagcgt tggctacccg   2700
tgatattgct gaagagcttg gcggcgaatg ggctgaccgc ttcctcgtgc tttacggtat   2760
cgccgctccc gattcgcagc gcatcgcctt ctatcgcctt cttgacgagt tcttctgaat   2820
tattaacgct tacaatttcc tgatgcggta ttttctcctt acgcatctgt gcggtatttc   2880
acaccgcata caggtggcac ttttcgggga aatgtgcgcg gaacccctat ttgtttattt   2940
ttctaaatac attcaaatat gtatccgctc atgagacaat aaccctgata aatgcttcaa   3000
taatagcacg tgctaaaact tcatttttaa tttaaaagga tctaggtgaa gatccttttt   3060
gataatctca tgaccaaaat cccttaacgt gagttttcgt tccactgagc gtcagacccc   3120
gtagaaaaga tcaaaggatc ttcttgagat cctttttttc tgcgcgtaat ctgctgcttg   3180
caaacaaaaa aaccaccgct accagcggtg gtttgtttgc cggatcaaga gctaccaact   3240
ctttttccga aggtaactgg cttcagcaga gcgcagatac caaatactgt ccttctagtg   3300
tagccgtagt taggccacca cttcaagaac tctgtagcac cgcctacata cctcgctctg   3360
ctaatcctgt taccagtggc tgctgccagt ggcgataagt cgtgtcttac cgggttggac   3420
tcaagacgat agttaccgga taaggcgcag cggtcgggct gaacgggggg ttcgtgcaca   3480
cagcccagct tggagcgaac gacctacacc gaactgagat acctacagcg tgagctatga   3540
gaaagcgcca cgcttcccga agggagaaag gcggacaggt atccggtaag cggcagggtc   3600
```

ggaacaggag agcgcacgag ggagcttcca gggggaaacg cctggtatct ttatagtcct 3660
gtcgggtttc gccacctctg acttgagcgt cgatttttgt gatgctcgtc aggggggcgg 3720
agcctatgga aaaacgccag caacgcggcc tttttacggt tcctgggctt ttgctggcct 3780
tttgctcaca tgttctt 3797

<210> SEQ ID NO 8
<211> LENGTH: 3740
<212> TYPE: DNA
<213> ORGANISM: Homo sapiens

<400> SEQUENCE: 8
gactcttcgc gatgtacggg ccagatatac gcttgtcatg gcgactgtcc agctttgtgc 60
caggagcctc gcaggggttg atgggattgg ggttttcccc tcccatgtgc tcaagactgg 120
cgctaaaagt tttgagcttc tcaaaagtct agagccaccg tccagggagc aggtagctgc 180
tgggctccgg ggacactttg cgttcgggct gggagcgtgc tttccacgac ggtgacacgc 240
ttccctggat tggagaccca agctggctag cgccaccatg ctggaaggcg tgcaggtcga 300
gacaatttct cctggcgacg gcagaacatt ccccaagaga ggacagacct gcgtcgtgca 360
ctataccggc atgctcgagg atggcaagaa ggtggacagc agcagagaca gaaacaagcc 420
cttcaagttc atgctgggca agcaagaagt gatcagaggc tgggaagagg gcgtcgcaca 480
gatgtctgtg ggacagagag ccaagctgac aatcagccct gattacgcct acggcgccac 540
aggacatcct ggaatcatcc ctccacacgc cacactggtg ttcgacgtgg aactgctgaa 600
gctggaatct ggcggtggaa gcggagtgga tggctttgga gatgtgggag ccctggaatc 660
tctgagagga aacgccgatc tggcctacat cctgtccatg gaaccttgcg gccactgcct 720
gattatcaac aacgtgaact tctgcagaga gagcggcctg agaaccagaa ccggcagcaa 780
catcgactgc gagaagctga gaagaagatt cagcagcctg cacttcatgg tggaagtgaa 840
gggcgacctg accgccaaga aaatggtgct ggctctgctg gaactggccc agcaagatca 900
tggcgctctg gactgttgtg tggtggtcat cctgagtcac ggctgtcagg cctctcatct 960
gcaattccct ggcgccgtgt acggcacaga tggatgtcca gtgtccgtgg aaaagatcgt 1020
gaacatcttc aacggcacaa gctgccctag cctcggcgga aagcccaagc tgttctttat 1080
ccaagcctgt ggcggcgagc agaaggatca cggatttgag gtggccagca caagccctga 1140
ggatgagtct cctggaagca accctgagcc tgacgccaca cctttccaag agggactgag 1200
aaccttcgac cagctggacg ctatcagctc cctgcctaca cctagcgaca tcttcgtgtc 1260
ctacagcaca ttccccggct tcgtgtcttg gagagatccc aagtctggct cttggtacgt 1320
ggaaaccctg gacgatatct tcgagcagtg ggcccatagc gaggatctgc agtctctgct 1380
cctgagagtg gccaacgctg tgtccgtgaa gggcatctac aagcagatgc cctgcatcgt 1440
gtccatgctg aggaagaagc tgtttttcaa gaccagcgtg gactacccgt acgacgtgcc 1500
agattacgcc ctggactaag cggccgctcg agtctagagg gcccgtttaa acccgctgat 1560
cagcctcgac tgtgccttct agttgccagc catctgttgt ttgcccctcc cccgtgcctt 1620
ccttgaccct ggaaggtgcc actcccactg tcctttccta ataaaatgag gaaattgcat 1680
cgcattgtct gagtaggtgt cattctattc tggggggtgg ggtggggcag gacagcaagg 1740
gggaggattg ggaagacaat agcaggcatg ctggggatgc ggtgggctct atggcttcta 1800
ctgggcggtt ttatggacag caagcgaacc ggaattgcca gctggggcgc cctctggtaa 1860
ggttgggaag ccctgcaaag taaactggat ggctttctcg ccgccaagga tctgatggcg 1920
caggggatca agctctgatc aagagacagg atgaggatcg tttcgcatga ttgaacaaga 1980
tggattgcac gcaggttctc cggccgcttg ggtggagagg ctattcggct atgactgggc 2040
acaacagaca atcggctgct ctgatgccgc cgtgttccgg ctgtcagcgc aggggcgccc 2100
ggttcttttt gtcaagaccg acctgtccgg tgccctgaat gaactgcaag acgaggcagc 2160
gcggctatcg tggctggcca cgacgggcgt tccttgcgca gctgtgctcg acgttgtcac 2220
tgaagcggga agggactggc tgctattggg cgaagtgccg gggcaggatc tcctgtcatc 2280
tcaccttgct cctgccgaga aagtatccat catggctgat gcaatgcggc ggctgcatac 2340
gcttgatccg gctacctgcc cattcgacca ccaagcgaaa catcgcatcg agcgagcacg 2400
tactcggatg gaagccggtc ttgtcgatca ggatgatctg gacgaagagc atcaggggct 2460
cgcgccagcc gaactgttcg ccaggctcaa ggcgagcatg cccgacggcg aggatctcgt 2520
cgtgacccat ggcgatgcct gcttgccgaa tatcatggtg gaaaatggcc gcttttctgg 2580
attcatcgac tgtggccggc tgggtgtggc ggaccgctat caggacatag cgttggctac 2640
ccgtgatatt gctgaagagc ttggcggcga atgggctgac cgcttcctcg tgctttacgg 2700
tatcgccgct cccgattcgc agcgcatcgc cttctatcgc cttcttgacg agttcttctg 2760
aattattaac gcttacaatt tcctgatgcg gtattttctc cttacgcatc tgtgcggtat 2820
ttcacaccgc atacaggtgg cacttttcgg ggaaatgtgc gcggaacccc tatttgttta 2880
tttttctaaa tacattcaaa tatgtatccg ctcatgagac aataaccctg ataaatgctt 2940
caataatagc acgtgctaaa acttcatttt taatttaaaa ggatctaggt gaagatcctt 3000
tttgataatc tcatgaccaa aatcccttaa cgtgagtttt cgttccactg agcgtcagac 3060
cccgtagaaa agatcaaagg atcttcttga gatccttttt ttctgcgcgt aatctgctgc 3120
ttgcaaacaa aaaaaccacc gctaccagcg gtggtttgtt tgccggatca agagctacca 3180
actctttttc cgaaggtaac tggcttcagc agagcgcaga taccaaatac tgtccttcta 3240
gtgtagccgt agttaggcca ccacttcaag aactctgtag caccgcctac atacctcgct 3300
ctgctaatcc tgttaccagt ggctgctgcc agtggcgata agtcgtgtct taccgggttg 3360
gactcaagac gatagttacc ggataaggcg cagcggtcgg gctgaacggg gggttcgtgc 3420
acacagccca gcttggagcg aacgacctac accgaactga gatacctaca gcgtgagcta 3480
tgagaaagcg ccacgcttcc cgaagggaga aaggcggaca ggtatccggt aagcggcagg 3540
gtcggaacag gagagcgcac gagggagctt ccagggggaa acgcctggta tctttatagt 3600
cctgtcgggt ttcgccacct ctgacttgag cgtcgatttt tgtgatgctc gtcagggggg 3660
cggagcctat ggaaaaacgc cagcaacgcg gcctttttac ggttcctggg cttttgctgg 3720
ccttttgctc acatgttctt 3740

<210> SEQ ID NO 9
<211> LENGTH: 5456
<212> TYPE: DNA
<213> ORGANISM: Homo sapiens

<400> SEQUENCE: 9
gactcttcgc gatgtacggg ccagatatac gcttgtcatg gcgactgtcc agctttgtgc 60
caggagcctc gcaggggttg atgggattgg ggttttcccc tcccatgtgc tcaagactgg 120
cgctaaaagt tttgagcttc tcaaaagtct agagccaccg tccagggagc aggtagctgc 180
tgggctccgg ggacactttg cgttcgggct gggagcgtgc tttccacgac ggtgacacgc 240

-continued

```
ttccctggat tggagaccca agctggctag cgccaccatg ctggaaggcg tgcaggtcga    300
gacaatttct cctggcgacg gcagaacatt ccccaagaga ggacagacct gcgtcgtgca    360
ctataccggc atgctcgagg atggcaagaa ggtggacagc agcagagaca gaaacaagcc    420
cttcaagttc atgctgggca agcaagaagt gatcagaggc tgggaagagg gcgtcgcaca    480
gatgtctgtg ggacagagag ccaagctgac aatcagccct gattacgcct acggcgccac    540
aggacatcct ggaatcatcc ctccacacgc cacactggtg ttcgacgtgg aactgctgaa    600
gctggaatct ggcggtggat ctggcgtgga cggctttgga gatgtgggag ccctggaatc    660
tctgagagga aacgccgatc tggcctacat cctgtccatg gaaccttgcg gccactgcct    720
gattatcaac aacgtgaact tctgcagaga gagcggcctg agaaccagaa ccggcagcaa    780
catcgactgc gagaagctga gaagaagatt cagcagcctg cacttcatgg tggaagtgaa    840
gggcgacctg accgccaaga aaatggtgct ggctctgctg gaactggccc agcaagatca    900
tggcgctctg gactgttgtg tggtggtcat cctgagtcac ggctgtcagg cctctcatct    960
gcaattccct ggcgccgtgt acggcacaga tggatgtcca gtgtccgtgg aaaagatcgt   1020
gaacatcttc aacggcacaa gctgccctag cctcggcgga aagcccaagc tgttctttat   1080
ccaagcctgt ggcggcgagc agaaggatca cggatttgag gtggccagca caagccctga   1140
ggatgagtct cctggaagca accctgagcc tgacgccaca cctttccaag agggactgag   1200
aaccttcgac cagctggacg ctatcagctc cctgcctaca cctagcgaca tcttcgtgtc   1260
ctacagcaca ttccccggct tcgtgtcttg gagagatccc aagtctggct cttggtacgt   1320
ggaaaccctg gacgatatct tcgagcagtg ggcccatagc gaggatctgc agtctctgct   1380
cctgagagtg gccaacgctg tgtccgtgaa gggcatctac aagcagatgc ccggctgctt   1440
caacttcctg aggaagaagc tgtttttcaa gaccagcgtg gactacccgt acgacgtgcc   1500
agattacgcc ctggatggct ctggcgaagg cagaggatct ctgctgacat gtggcgacgt   1560
ggaagagaac cctggaccta tgtggctgca gtctctgctg ctgctgggaa cagtggcctg   1620
ttctatctct gcccctgcca gatctccatc tcctagcaca cagccttggg agcacgtgaa   1680
cgctatccaa gaagccagaa ggctgctgaa cctgagcaga gatacagccg ccgagatgaa   1740
cgagacagtg gaagtgatca gcgagatgtt cgacctgcaa gagcctacct gcctgcagac   1800
cagactggaa ctgtacaagc agggcctgag aggcagcctg acaaagctga agggccctct   1860
gacaatgatg gccagccact acaagcagca ctgccctcca acacctgaga caagctgcgc   1920
cacacagatc atcaccttcg agagcttcaa agagaacctg aaggacttcc tgctggtcat   1980
ccccttcgac tgctgggagc ctgttcaaga aggcagcgga gaaggacgag gcagtctgct   2040
gacttgcgga gatgtcgaag aaaatcccgg accaatggga tctatcggag ccgccagcat   2100
ggaattctgc ttcgacgtgt tcaaagagct gaaggtccac cacgccaacg agaacatctt   2160
ctactgccct atcgccatca tgagcgccct ggccatggtg tatctgggcg ccaaggatag   2220
caccagaaca cagatcaaca aggtcgtcag attcgacaag ctgcccggct tcggagatag   2280
catcgaagcc cagtgtggca ccagcgtgaa cgtgcacagc agcctgagag acatcctgaa   2340
ccagatcacc aagcctaacg acgtgtacag cttcagcctg gccagcagac tgtacgccga   2400
ggaaagatac cccatcctgc ctgagtacct gcagtgcgtg aaagagctgt acagaggcgg   2460
cctggaacct atcaacttcc agacagccgc cgatcaggcc agagagctga tcaactcttg   2520
ggtcgagagc cagaccaacg gcatcatcag aaacgtgctg cagcctagca gcgtggactc   2580
```

-continued

```
tcagacagcc atggtgctgg tcaacgccat cgtgtttaaa ggcctgtggg aaaagacctt   2640
caaggacgag gatacccagg ccatgccttt cagagtgacc gagcaagagt ccaagcctgt   2700
gcagatgatg taccagatcg gcctgtttag agtggcctcc atggcctccg agaagatgaa   2760
gatcctggaa ctgcctttcg cctccggcac catgtctatg ctggtgctgc tgcctgatga   2820
ggtgtccgga ctggaacagc tggaatccat catcaacttc gagaagctga ccgagtggac   2880
cagcagcaac gtgatggaag aacggaagat caaggtgtac ctgcctcgga tgaagatgga   2940
agagaagtac aacctgacca gcgtgctgat ggccatggga atcaccgatg tgttcagcag   3000
ctctgccaac ctgagcggca tctcttctgc cgagagcctg aagatttctc aggccgtgca   3060
tgctgcccac gccgagatta acgaagccgg cagagaagtt gtgggatctg ctgaagcagg   3120
cgtggacgcc gcttctgtgt ctgaggaatt cagagccgac catccttttc tgttctgcat   3180
caagcacatt gccaccaacg ccgtgctgtt cttcggcaga tgtgtgtccc cttgagcggc   3240
cgctcgagtc tagagggccc gtttaaaccc gctgatcagc ctcgactgtg ccttctagtt   3300
gccagccatc tgttgtttgc ccctcccccg tgccttcctt gaccctggaa ggtgccactc   3360
ccactgtcct ttcctaataa aatgaggaaa ttgcatcgca ttgtctgagt aggtgtcatt   3420
ctattctggg gggtggggtg gggcaggaca gcaaggggga ggattgggaa gacaatagca   3480
ggcatgctgg ggatgcggtg ggctctatgg cttctactgg gcggttttat ggacagcaag   3540
cgaaccggaa ttgccagctg gggcgccctc tggtaaggtt gggaagccct gcaaagtaaa   3600
ctggatggct ttctcgccgc caaggatctg atggcgcagg ggatcaagct ctgatcaaga   3660
gacaggatga ggatcgtttc gcatgattga acaagatgga ttgcacgcag gttctccggc   3720
cgcttgggtg gagaggctat tcggctatga ctgggcacaa cagacaatcg gctgctctga   3780
tgccgccgtg ttccggctgt cagcgcaggg gcgcccggtt ctttttgtca agaccgacct   3840
gtccggtgcc ctgaatgaac tgcaagacga ggcagcgcgg ctatcgtggc tggccacgac   3900
gggcgttcct tgcgcagctg tgctcgacgt tgtcactgaa gcgggaaggg actggctgct   3960
attgggcgaa gtgccggggc aggatctcct gtcatctcac cttgctcctg ccgagaaagt   4020
atccatcatg gctgatgcaa tgcggcggct gcatacgctt gatccggcta cctgcccatt   4080
cgaccaccaa gcgaaacatc gcatcgagcg agcacgtact cggatggaag ccggtcttgt   4140
cgatcaggat gatctggacg aagagcatca ggggctcgcg ccagccgaac tgttcgccag   4200
gctcaaggcg agcatgcccg acggcgagga tctcgtcgtg acccatggcg atgcctgctt   4260
gccgaatatc atggtggaaa atggccgctt ttctggattc atcgactgtg gccggctggg   4320
tgtggcggac cgctatcagg acatagcgtt ggctacccgt gatattgctg aagagcttgg   4380
cggcgaatgg gctgaccgct tcctcgtgct ttacggtatc gccgctcccg attcgcagcg   4440
catcgccttc tatcgccttc ttgacgagtt cttctgaatt attaacgctt acaatttcct   4500
gatgcggtat tttctcctta cgcatctgtg cggtatttca caccgcatac aggtggcact   4560
tttcggggaa atgtgcgcgg aacccctatt tgtttatttt tctaaataca ttcaaatatg   4620
tatccgctca tgagacaata accctgataa atgcttcaat aatagcacgt gctaaaactt   4680
catttttaat ttaaaaggat ctaggtgaag atcctttttg ataatctcat gaccaaaatc   4740
ccttaacgtg agttttcgtt ccactgagcg tcagaccccg tagaaaagat caaaggatct   4800
tcttgagatc cttttttttct gcgcgtaatc tgctgcttgc aaacaaaaaa accaccgcta   4860
ccagcggtgg tttgtttgcc ggatcaagag ctaccaactc tttttccgaa ggtaactggc   4920
ttcagcagag cgcagatacc aaatactgtc cttctagtgt agccgtagtt aggccaccac   4980
```

ttcaagaact ctgtagcacc gcctacatac ctcgctctgc taatcctgtt accagtggct 5040
gctgccagtg gcgataagtc gtgtcttacc gggttggact caagacgata gttaccggat 5100
aaggcgcagc ggtcgggctg aacggggggt tcgtgcacac agcccagctt ggagcgaacg 5160
acctacaccg aactgagata cctacagcgt gagctatgag aaagcgccac gcttcccgaa 5220
gggagaaagg cggacaggta tccggtaagc ggcagggtcg gaacaggaga gcgcacgagg 5280
gagcttccag ggggaaacgc ctggtatctt tatagtcctg tcgggtttcg ccacctctga 5340
cttgagcgtc gatttttgtg atgctcgtca ggggggcgga gcctatggaa aaacgccagc 5400
aacgcggcct ttttacggtt cctgggcttt tgctggcctt ttgctcacat gttctt 5456

<210> SEQ ID NO 10
<211> LENGTH: 4586
<212> TYPE: DNA
<213> ORGANISM: Homo sapiens

<400> SEQUENCE: 10
gactcttcgc gatgtacggg ccagatatac gcttgtcatg gcgactgtcc agctttgtgc 60
caggagcctc gcaggggttg atgggattgg ggttttcccc tcccatgtgc tcaagactgg 120
cgctaaaagt tttgagcttc tcaaaagtct agagccaccg tccagggagc aggtagctgc 180
tgggctccgg ggacactttg cgttcgggct gggagcgtgc tttccacgac ggtgacacgc 240
ttccctggat tggagaccca agctggctag cgccaccatg ctggaaggcg tgcaggtcga 300
gacaatttct cctggcgacg gcagaacatt ccccaagaga ggacagacct gcgtcgtgca 360
ctataccggc atgctcgagg atggcaagaa ggtggacagc agcagagaca gaaacaagcc 420
cttcaagttc atgctgggca agcaagaagt gatcagaggc tgggaagagg gcgtcgcaca 480
gatgtctgtg ggacagagag ccaagctgac aatcagccct gattacgcct acggcgccac 540
aggacatcct ggaatcatcc ctccacacgc cacactggtg ttcgacgtgg aactgctgaa 600
gctggaatct ggcggtggat ctggcgtgga cggctttgga gatgtgggag ccctggaatc 660
tctgagagga aacgccgatc tggcctacat cctgtccatg gaaccttgcg gccactgcct 720
gattatcaac aacgtgaact tctgcagaga gagcggcctg agaaccagaa ccggcagcaa 780
catcgactgc gagaagctga gaagaagatt cagcagcctg cacttcatgg tggaagtgaa 840
gggcgacctg accgccaaga aaatggtgct ggctctgctg gaactggccc agcaagatca 900
tggcgctctg gactgttgtg tggtggtcat cctgagtcac ggctgtcagg cctctcatct 960
gcaattccct ggcgccgtgt acggcacaga tggatgtcca gtgtccgtgg aaaagatcgt 1020
gaacatcttc aacggcacaa gctgccctag cctcggcgga aagcccaagc tgttctttat 1080
ccaagcctgt ggcggcgagc agaaggatca cggatttgag gtggccagca caagccctga 1140
ggatgagtct cctggaagca accctgagcc tgacgccaca cctttccaag agggactgag 1200
aaccttcgac cagctggacg ctatcagctc cctgcctaca cctagcgaca tcttcgtgtc 1260
ctacagcaca ttccccggct tcgtgtcttg gagagatccc aagtctggct cttggtacgt 1320
ggaaaccctg gacgatatct tcgagcagtg ggcccatagc gaggatctgc agtctctgct 1380
cctgagagtg gccaacgctg tgtccgtgaa gggcatctac aagcagatgc ccggctgctt 1440
caacttcctg aggaagaagc tgtttttcaa gaccagcgtg gactacccgt acgacgtgcc 1500
agattacgcc ctggatggct ctggcgaagg cagaggatct ctgctgacat gtggcgacgt 1560
ggaagagaac cctggaccta tgatcgagac atacaaccag acaagcccca gaagcgccgc 1620

-continued

```
cacaggactg cctatcagca tgaagatctt tatgtacctg ctgaccgtgt tcctgatcac   1680
ccagatgatc ggctctgccc tgtttgccgt gtacctgcac agaaggctgg acaagatcga   1740
ggacgagaga aacctgcacg aggacttcgt gttcatgaag accatccaga gatgcaacac   1800
cggcgagaga agcctgagcc tgctgaactg cgaggaaatc aagagccagt tcgagggctt   1860
cgtgaaggac atcatgctga acaaagagga aacgaagaaa gaaaactcct tcgagatgca   1920
gaagggcgat cagaaccctc agatcgccgc tcacgtgatc agcgaggcca gcagcaaaac   1980
aacatctgtg ctgcagtggg ccgagaaggg ctactacacc atgagcaaca acctggtcac   2040
cctggaaaac ggcaagcagc tgacagtgaa gagacagggc ctgtactaca tctacgccca   2100
agtgaccttc tgcagcaaca gagaggcttc ctctcaggcc ccttttatcg ccagcctgtg   2160
tctgaagtcc cctggcagat ttgagagaat cctgctgaga gccgccaaca cacacagctc   2220
tgctaagcct tgtggccagc agtctatcca cctcggcgga gtgtttgaac tgcagcctgg   2280
cgcctctgtg ttcgtgaacg tgacagatcc ttctcaggtg tcccacggca ccggcttcac   2340
atcttttgga ctgctgaagc tctgagcggc cgctcgagtc tagagggccc gtttaaaccc   2400
gctgatcagc ctcgactgtg ccttctagtt gccagccatc tgttgtttgc ccctcccccg   2460
tgccttcctt gaccctggaa ggtgccactc ccactgtcct ttcctaataa aatgaggaaa   2520
ttgcatcgca ttgtctgagt aggtgtcatt ctattctggg gggtggggtg gggcaggaca   2580
gcaaggggga ggattgggaa gacaatagca ggcatgctgg ggatgcggtg ggctctatgg   2640
cttctactgg gcggttttat ggacagcaag cgaaccggaa ttgccagctg gggcgccctc   2700
tggtaaggtt gggaagccct gcaaagtaaa ctggatggct ttctcgccgc caaggatctg   2760
atggcgcagg ggatcaagct ctgatcaaga gacaggatga ggatcgtttc gcatgattga   2820
acaagatgga ttgcacgcag gttctccggc cgcttgggtg gagaggctat tcggctatga   2880
ctgggcacaa cagacaatcg gctgctctga tgccgccgtg ttccggctgt cagcgcaggg   2940
gcgcccggtt ctttttgtca agaccgacct gtccggtgcc ctgaatgaac tgcaagacga   3000
ggcagcgcgg ctatcgtggc tggccacgac gggcgttcct tgcgcagctg tgctcgacgt   3060
tgtcactgaa gcgggaaggg actggctgct attgggcgaa gtgccggggc aggatctcct   3120
gtcatctcac cttgctcctg ccgagaaagt atccatcatg gctgatgcaa tgcggcggct   3180
gcatacgctt gatccggcta cctgcccatt cgaccaccaa gcgaaacatc gcatcgagcg   3240
agcacgtact cggatggaag ccggtcttgt cgatcaggat gatctggacg aagagcatca   3300
ggggctcgcg ccagccgaac tgttcgccag gctcaaggcg agcatgcccg acggcgagga   3360
tctcgtcgtg acccatggcg atgcctgctt gccgaatatc atggtggaaa atggccgctt   3420
ttctggattc atcgactgtg gccggctggg tgtggcggac cgctatcagg acatagcgtt   3480
ggctacccgt gatattgctg aagagcttgg cggcgaatgg gctgaccgct tcctcgtgct   3540
ttacggtatc gccgctcccg attcgcagcg catcgccttc tatcgccttc ttgacgagtt   3600
cttctgaatt attaacgctt acaatttcct gatgcggtat tttctcctta cgcatctgtg   3660
cggtatttca caccgcatac aggtggcact tttcggggaa atgtgcgcgg aacccctatt   3720
tgtttatttt tctaaataca ttcaaatatg tatccgctca tgagacaata accctgataa   3780
atgcttcaat aatagcacgt gctaaaactt catttttaat ttaaaaggat ctaggtgaag   3840
atcctttttg ataatctcat gaccaaaatc ccttaacgtg agttttcgtt ccactgagcg   3900
tcagaccccg tagaaaagat caaaggatct tcttgagatc ctttttttct gcgcgtaatc   3960
tgctgcttgc aaacaaaaaa accaccgcta ccagcggtgg tttgtttgcc ggatcaagag   4020
```

ctaccaactc tttttccgaa ggtaactggc ttcagcagag cgcagatacc aaatactgtc 4080
cttctagtgt agccgtagtt aggccaccac ttcaagaact ctgtagcacc gcctacatac 4140
ctcgctctgc taatcctgtt accagtggct gctgccagtg gcgataagtc gtgtcttacc 4200
gggttggact caagacgata gttaccggat aaggcgcagc ggtcgggctg aacggggggt 4260
tcgtgcacac agcccagctt ggagcgaacg acctacaccg aactgagata cctacagcgt 4320
gagctatgag aaagcgccac gcttcccgaa gggagaaagg cggacaggta tccggtaagc 4380
ggcagggtcg gaacaggaga gcgcacgagg gagcttccag ggggaaacgc ctggtatctt 4440
tatagtcctg tcgggtttcg ccacctctga cttgagcgtc gatttttgtg atgctcgtca 4500 gggggcgga gcctatggaa aaacgccagc aacgcggcct ttttacggtt cctgggcttt 4560
tgctggcctt ttgctcacat gttctt 4586

<210> SEQ ID NO 11
<211> LENGTH: 4961
<212> TYPE: DNA
<213> ORGANISM: Homo sapiens

<400> SEQUENCE: 11
gactcttcgc gatgtacggg ccagatatac gcttgtcatg gcgactgtcc agctttgtgc 60
caggagcctc gcaggggttg atgggattgg ggtttcccc tcccatgtgc tcaagactgg 120
cgctaaaagt tttgagcttc tcaaaagtct agagccaccg tccagggagc aggtagctgc 180
tgggctccgg ggacactttg cgttcgggct gggagcgtgc tttccacgac ggtgacacgc 240
ttccctggat tggagaccca agctggctag cgccaccatg ctggaaggcg tgcaggtcga 300
gacaatttct cctggcgacg gcagaacatt ccccaagaga ggacagacct gcgtcgtgca 360
ctataccggc atgctcgagg atggcaagaa ggtggacagc agcagagaca gaaacaagcc 420
cttcaagttc atgctgggca agcaagaagt gatcagaggc tgggaagagg gcgtcgcaca 480
gatgtctgtg ggacagagag ccaagctgac aatcagccct gattacgcct acggcgccac 540
aggacatcct ggaatcatcc ctccacacgc cacactggtg ttcgacgtgg aactgctgaa 600
gctggaatct ggcggtggat ctggcgtgga cggctttgga gatgtgggag ccctggaatc 660
tctgagagga aacgccgatc tggcctacat cctgtccatg gaaccttgcg gccactgcct 720
gattatcaac aacgtgaact tctgcagaga gagcggcctg agaaccagaa ccggcagcaa 780
catcgactgc gagaagctga gaagaagatt cagcagcctg cacttcatgg tggaagtgaa 840
gggcgacctg accgccaaga aaatggtgct ggctctgctg gaactggccc agcaagatca 900
tggcgctctg gactgttgtg tggtggtcat cctgagtcac ggctgtcagg cctctcatct 960
gcaattccct ggcgccgtgt acggcacaga tggatgtcca gtgtccgtgg aaaagatcgt 1020
gaacatcttc aacggcacaa gctgccctag cctcggcgga aagcccaagc tgttctttat 1080
ccaagcctgt ggcggcgagc agaaggatca cggatttgag gtggccagca caagccctga 1140
ggatgagtct cctggaagca accctgagcc tgacgccaca cctttccaag agggactgag 1200
aaccttcgac cagctggacg ctatcagctc cctgcctaca cctagcgaca tcttcgtgtc 1260
ctacagcaca ttccccggct tcgtgtcttg gagagatccc aagtctggct cttggtacgt 1320
ggaaaccctg gacgatatct tcgagcagtg ggcccatagc gaggatctgc agtctctgct 1380
cctgagagtg gccaacgctg tgtccgtgaa gggcatctac aagcagatgc ccggctgctt 1440
caacttcctg aggaagaagc tgtttttcaa gaccagcgtg gactacccgt acgacgtgcc 1500

-continued

```
agattacgcc ctggatggct ctggcgaagg cagaggatct ctgctgacat gtggcgacgt   1560
ggaagagaac cctggaccta tgggatctat cggagccgcc agcatggaat tctgcttcga   1620
cgtgttcaaa gagctgaagg tccaccacgc caacgagaac atcttctact gccctatcgc   1680
catcatgagc gccctggcca tggtgtatct gggcgccaag gatagcacca gaacacagat   1740
caacaaggtc gtcagattcg acaagctgcc cggcttcgga gatagcatcg aagcccagtg   1800
tggcaccagc gtgaacgtgc acagcagcct gagagacatc ctgaaccaga tcaccaagcc   1860
taacgacgtg tacagcttca gcctggccag cagactgtac gccgaggaaa gatacccccat  1920
cctgcctgag tacctgcagt gcgtgaaaga gctgtacaga ggcggcctgg aacctatcaa   1980
cttccagaca gccgccgatc aggccagaga gctgatcaac tcttgggtcg agagccagac   2040
caacggcatc atcagaaacg tgctgcagcc tagcagcgtg gactctcaga cagccatggt   2100
gctggtcaac gccatcgtgt ttaaaggcct gtgggaaaag accttcaagg acgaggatac   2160
ccaggccatg cctttcagag tgaccgagca agagtccaag cctgtgcaga tgatgtacca   2220
gatcggcctg tttagagtgg cctccatggc ctccgagaag atgaagatcc tggaactgcc   2280
tttcgcctcc ggcaccatgt ctatgctggt gctgctgcct gatgaggtgt ccggactgga   2340
acagctggaa tccatcatca acttcgagaa gctgaccgag tggaccagca gcaacgtgat   2400
ggaagaacgg aagatcaagg tgtacctgcc tcggatgaag atggaagaga agtacaacct   2460
gaccagcgtg ctgatggcca tgggaatcac cgatgtgttc agcagctctg ccaacctgag   2520
cggcatctct tctgccgaga gcctgaagat ttctcaggcc gtgcatgctg cccacgccga   2580
gattaacgaa gccggcagag aagttgtggg atctgctgaa gcaggcgtgg acgccgcttc   2640
tgtgtctgag gaattcagag ccgaccatcc ttttctgttc tgcatcaagc acattgccac   2700
caacgccgtg ctgttcttcg gcagatgtgt gtccccttga gcggccgctc gagtctagag   2760
ggcccgttta aacccgctga tcagcctcga ctgtgccttc tagttgccag ccatctgttg   2820
tttgcccctc ccccgtgcct tccttgaccc tggaaggtgc cactcccact gtcctttcct   2880
aataaaatga ggaaattgca tcgcattgtc tgagtaggtg tcattctatt ctggggggtg   2940
gggtggggca ggacagcaag ggggaggatt gggaagacaa tagcaggcat gctggggatg   3000
cggtgggctc tatggcttct actgggcggt tttatggaca gcaagcgaac cggaattgcc   3060
agctggggcg ccctctggta aggttgggaa gccctgcaaa gtaaactgga tggctttctc   3120
gccgccaagg atctgatggc gcaggggatc aagctctgat caagagacag gatgaggatc   3180
gtttcgcatg attgaacaag atggattgca cgcaggttct ccggccgctt gggtggagag   3240
gctattcggc tatgactggg cacaacagac aatcggctgc tctgatgccg ccgtgttccg   3300
gctgtcagcg caggggcgcc cggttctttt tgtcaagacc gacctgtccg gtgccctgaa   3360
tgaactgcaa gacgaggcag cgcggctatc gtggctggcc acgacgggcg ttccttgcgc   3420
agctgtgctc gacgttgtca ctgaagcggg aagggactgg ctgctattgg gcgaagtgcc   3480
ggggcaggat ctcctgtcat ctcaccttgc tcctgccgag aaagtatcca tcatggctga   3540
tgcaatgcgg cggctgcata cgcttgatcc ggctacctgc ccattcgacc accaagcgaa   3600
acatcgcatc gagcgagcac gtactcggat ggaagccggt cttgtcgatc aggatgatct   3660
ggacgaagag catcaggggc tcgcgccagc cgaactgttc gccaggctca aggcgagcat   3720
gcccgacggc gaggatctcg tcgtgaccca tggcgatgcc tgcttgccga atatcatggt   3780
ggaaaatggc cgcttttctg gattcatcga ctgtggccgg ctgggtgtgg cggaccgcta   3840
tcaggacata gcgttggcta cccgtgatat tgctgaagag cttggcggcg aatgggctga   3900
```

-continued

```
ccgcttcctc gtgctttacg gtatcgccgc tcccgattcg cagcgcatcg ccttctatcg   3960
ccttcttgac gagttcttct gaattattaa cgcttacaat ttcctgatgc ggtattttct   4020
ccttacgcat ctgtgcggta tttcacaccg catacaggtg gcacttttcg gggaaatgtg   4080
cgcggaaccc ctatttgttt atttttctaa atacattcaa atatgtatcc gctcatgaga   4140
caataaccct gataaatgct tcaataatag cacgtgctaa aacttcattt ttaatttaaa   4200
aggatctagg tgaagatcct ttttgataat ctcatgacca aaatccctta acgtgagttt   4260
tcgttccact gagcgtcaga ccccgtagaa aagatcaaag gatcttcttg agatcctttt   4320
tttctgcgcg taatctgctg cttgcaaaca aaaaaaccac cgctaccagc ggtggtttgt   4380
ttgccggatc aagagctacc aactcttttt ccgaaggtaa ctggcttcag cagagcgcag   4440
ataccaaata ctgtccttct agtgtagccg tagttaggcc accacttcaa gaactctgta   4500
gcaccgccta catacctcgc tctgctaatc ctgttaccag tggctgctgc cagtggcgat   4560
aagtcgtgtc ttaccgggtt ggactcaaga cgatagttac cggataaggc gcagcggtcg   4620
ggctgaacgg ggggttcgtg cacacagccc agcttggagc gaacgaccta caccgaactg   4680
agatacctac agcgtgagct atgagaaagc gccacgcttc ccgaagggag aaaggcggac   4740
aggtatccgg taagcggcag ggtcggaaca ggagagcgca cgagggagct tccaggggga   4800
aacgcctggt atctttatag tcctgtcggg tttcgccacc tctgacttga gcgtcgattt   4860
ttgtgatgct cgtcaggggg gcggagccta tggaaaaacg ccagcaacgc ggccttttta   4920
cggttcctgg gcttttgctg gccttttgct cacatgttct t                       4961
```

EXPRESSION CONSTRUCTS, FUSOGENIC LIPID-BASED NANOPARTICLES AND METHODS OF USE THEREOF

CROSS-REFERENCE TO RELATED APPLICATIONS

This application is a national phase entry of International Application No. PCT/US2018/013033, filed on Jan. 9, 2018, which claims the benefit of U.S. Provisional Patent Application No. 62/444,360, filed on Jan. 9, 2017, each of which is incorporated herein by reference in its entirety.

SEQUENCE LISTING

The present application includes a Sequence Listing in electronic format as a txt file entitled "OSIN-01-0202WO01_2018-01-09_SEQLIST_ST25," which was created on Jan. 9, 2018 and which has a size of 44,455 bytes. The contents of txt file "OSIN-01-0202WO01_2018-01-09_SEQLIST_ST25" are incorporated by reference herein.

BACKGROUND OF THE DISCLOSURE

Technical Field

The present disclosure relates, generally, to the field of medicine, including the treatment of disease, promotion of longevity, anti-aging, and health extension. More specifically, this disclosure concerns compositions and methods for reducing the growth and/or survival of cells that are associated with aging, disease, and other conditions. Provided are expression constructs for target cell specific expression of therapeutic proteins, which constructs exploit unique intracellular functionality, including transcription regulatory functionality, that is present within a target cell but is either absent from or substantially reduced in a normal, non-target cell. Such expression constructs are used in systems that include a vector for the delivery of a nucleic acid to a target cell, which vectors may comprise, but do not necessarily require, a fusogenic lipid nanoparticle and, optionally, a targeting moiety for enhancing the delivery of an expression construct to a target cell.

Description of the Related Art

Cancer cells, senescent cells, and other cells having an undesirable phenotype can accumulate over the course of a person's life and, without appropriate treatment, such cells can contribute to or even cause a person's morbidity and, ultimately, mortality.

The role of senescent cells in disease and the potential benefits of eliminating senescent cells has been discussed in scientific publications such as Baker et al. *Nature* 479:232-6 (2011). Systems and methods have been described that purport to address the problem of accumulating senescent cells. For example, Grigg, PCT Patent Publication No. WO 1992/009298, describes a system for preventing or reversing cell senescence with chemical compounds similar to carnosine and Gruber, U.S. Patent Publication No. 2012/0183534, describes systems for killing senescent cells with radiation, ultrasound, toxins, antibodies, and antibody-toxin conjugates, which systems include senescent cell-surface proteins for use in targeting of therapeutic molecules.

The selective killing of senescent cells has proven impractical in mammals other than genetically-modified laboratory research animals. Currently-available systems and methods exhibit substantial systemic toxicity, inadequate targeting of cells of interest, and a lack of adequate safety features. These shortcomings in the art have hampered the development of safe and effective therapies for the treatment of certain cancers and for slowing the effects of aging.

SUMMARY OF THE DISCLOSURE

The present disclosure is based upon the discovery that a cell, such as a cell that is associated with aging, a disease, and/or another condition (collectively, "a target cell"), can be selectively killed, in a target cell-specific manner, without the need for the targeted delivery of a therapeutic agent to the target cell. The expression constructs, systems, and methods described herein overcome safety and efficacy concerns that are associated with existing technologies that employ targeted delivery of therapeutic agents, which technologies have yielded limited therapeutic benefit to patients in need thereof.

As described herein, the present disclosure provides expression cassettes, systems, and methods for inducing, in a target cell-specific manner, the expression of a nucleic acid that encodes a protein that, when produced in a cell, reduces or eliminates the growth and/or survival of a cell, such as a cell that is associated with aging, disease, and/or other condition.

The expression cassettes, systems, and methods described herein exploit the unique transcription regulatory machinery that is intrinsic to certain cells that are associated with age (such as senescent cells), disease (such as cancers, infectious diseases, and bacterial diseases), as well as other conditions, which transcription regulatory machinery is not operative, or exhibits substantially reduced activity, in a normal cell (i.e., "a non-target cell") that is not associated with aging, disease, or other condition.

The presently-disclosed expression cassettes, systems, and methods achieve a high degree of target cell specificity as a consequence of intracellular functionality that is provided by, and unique to, the target cell, which intracellular functionality is not provided by, or is substantially reduced in, a normal, non-target cell. Thus, the presently disclosed systems and methods employ nucleic acid delivery vectors that are non-specific with respect to the cell type to which the nucleic acid is delivered and, indeed, the vectors described herein need not be configured for target cell-specific delivery of a nucleic acid (e.g., an expression cassette) to achieve target cell specificity and, consequently, the therapeutically effective reduction, prevention, and/or elimination in the growth and/or survival of a target cell.

Within certain embodiments, the present disclosure provides expression constructs for the targeted production of therapeutic proteins within a target cell, such as a cell that is associated with aging, disease, and/or another condition. The expression constructs disclosed herein comprise: (1) a transcriptional promoter that is activated in response to one or more factors each of which is produced within a target cell and (2) a nucleic acid that is operably linked to and under regulatory control of the transcriptional promoter, wherein the nucleic acid encodes a therapeutic protein that can reduce, prevent, and/or eliminate the growth and/or survival of a cell, including the target cell.

Within certain aspects of these embodiments, the transcriptional promoter is activated in a target cell that is associated with a disease, condition, or age but is not activated in a normal mammalian cell that is not associated with the disease, condition, or aging. Target cell-specific transcriptional activation is achieved by the action of one or more factors that are produced in the target cell but not produced in a normal mammalian cell, including a normal human cell, such as normal skeletal myoblasts, normal adipose cells, normal cells of the eye, normal brain cells, normal liver cells, normal colon cells, normal lung cells, normal pancreas cells, and/or normal heart cells, which normal cells are not associated with the disease, condition, or aging.

Within other aspects of these embodiments, the target cell can be a mammalian cell or a bacterial cell. Target mammalian cells can include human cells such as senescent cells, cancer cells, precancerous cells, dysplastic cells, and cells that are infected with an infectious agent.

In certain aspects of these embodiments wherein the human target cell is a senescent cell, the transcriptional promoter can include the p16INK4a/CDKN2A transcriptional promoter, which is responsive to activation by transcription factors such as SP1, ETS1, and/or ETS2. In other aspects of these embodiments wherein the human target cell is a senescent cell, the transcriptional promoter can include the p21/CDKN1A transcriptional promoter, which is responsive to p53/TP53. In a target cell, such as a senescent cell, transcriptional promoters induce the expression of a nucleic acid that encodes a therapeutic protein such as, for example, CASP3, CASP8, CASP9, BAX, DFF40, HSV-TK, and cytosine deaminase as well as inducible variants of CASP3, CASP8, CASP9, BAX, DFF40, HSV-TK, and cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

In other aspects of these embodiments wherein the human target cell is a cancer cell, such as a brain cancer cell, a prostate cancer cell, a lung cancer cell, a colorectal cancer cell, a breast cancer cell, a liver cancer cell, a hematologic cancer cell, and a bone cancer cell, the transcriptional promoter can include the $p21^{cip1/waf1}$ promoter, the $p27^{kip1}$ promoter, the $p57^{kip2}$ promoter, the TdT promoter, the Rag-1 promoter, the B29 promoter, the Blk promoter, the CD19 promoter, the BLNK promoter, and/or the λ5 promoter, which transcriptional promoter is responsive to activation by one or more transcription factors such as an EBF3, O/E-1, Pax-5, E2A, p53, VP16, MLL, HSF1, NF-IL6, NFAT1, AP-1, AP-2, HOX, E2F3, and/or NF-κB transcription factor, and which transcriptional activation induces the expression of a nucleic acid that encodes a therapeutic protein such as, for example, CASP3, CASP8, CASP9, BAX, DFF40, HSV-TK, or cytosine deaminase as well as inducible variants of CASP3, CASP8, CASP9, BAX, DFF40, HSV-TK, and cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

In still further aspects of these embodiments wherein the target cell is a human cell that is infected with an infectious agent, such as a virus, including, for example, a herpes virus, a polio virus, a hepatitis virus, a retrovirus virus, an influenza virus, and a rhino virus, or the target cell is a bacterial cell, the transcriptional promoter can be activated by a factor that is expressed by the infectious agent or bacterial cell, which transcriptional activation induces the expression of a nucleic acid that encodes a therapeutic protein such as, for example, CASP3, CASP8, CASP9, BAX, DFF40, HSV-TK, and cytosine deaminase as well as inducible variants of CASP3, CASP8, CASP9, BAX, DFF40, HSV-TK, and cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

Within other embodiments, the present disclosure provides systems for the targeted production of a therapeutic protein within a target cell. These systems comprise a vector that is capable of delivering a nucleic acid to a cell, including a target cell as well as a non-target cell, wherein the vector comprises an expression construct for the targeted production of a therapeutic protein within a target cell (e.g., a cell that is associated with age, disease, or other condition) but not within a non-target cell, wherein the expression construct comprises a transcriptional promoter that is activated in response to one or more factors each of which is produced within said target cell; and a nucleic acid that is operably linked to and under regulatory control of the transcriptional promoter, wherein the nucleic acid encodes a therapeutic protein that can reduce, prevent, and/or eliminate the growth and/or survival of a cell in which it is produced, including a target cell.

Within certain aspects of these embodiments, formulations and systems include lipid nanoparticle (LNP) formulations and systems wherein an LPN encapsulates a polynucleotide construct (e.g., a plasmid DNA) comprising a coding region for a pro-apoptotic protein, such as a caspase protein, and wherein the coding region is under the regulatory control of a target cell-specific transcriptional promoter, such as a senescent cell-specific transcriptional promoter or a cancer cell-specific transcriptional promoter. Exemplary cell-specific transcriptional promoters include p16, p22, p53. Exemplary coding regions for pro-apoptotic proteins include coding regions for CASP3, CASP8, CASP9, BAX, DFF40, HSV-TK, and cytosine deaminase proteins. Pro-apoptotic proteins include inducible CASP3, CASP8, CASP9, BAX, DFF40, HSV-TK, and cytosine deaminase proteins and self-activating CASP3, CASP8, CASP9, BAX, DFF40, HSV-TK, and cytosine deaminase proteins, which are exemplified herein by an inducible Caspase 9 (iCasp9) or a self-activating Caspase 9 (saCASP9).

Inducible pro-apoptotic proteins, including iCasp9 proteins, include a dimerization domain, such as an FKBP or FK506 binding protein domain, that binds to a chemical inducer of dimerization (CID), such as AP1903 or AP20187. Clackson, *Proc Natl Acad Sci USA.* 95:10437-10442 (1998). Inducible Caspase 9 (iCasp9; Ariad, Erie, Pa.) may be activated in the presence of AP1903. U.S. Pat. No. 5,869,337 and Straathof, *Blood* 105:4247-4354 (2005). Exemplary such human genes encoding FKBP domains include A1P, A1PL1, FKBP1A, FKBP1B, FKBP2, FKBP3, FHBP5, FKBP6, FKBP7, FKBP8, FKBP8, FKBP9L, FKBP10, FKBP11, FKBP14, FKBP15, FKBP52, and LOC541473.

Within other aspects of these embodiments, lipid nanoparticles (LNP) are fusogenic lipid nanoparticles, such as fusogenic lipid nanoparticles comprising a fusogenic protein, such as a fusogenic p14 FAST fusion protein from reptilian reovirus to catalyze lipid mixing between the LNP and target cell plasma membrane.

Contacting a cell expressing an iCasp9 protein with a CID facilitates the dimerization of the iCasp9 protein, which triggers apoptosis in a target cell. AP1903 has been used in humans multiple times, its intravenous safety has been confirmed, and its pharmacokinetics determined. Iuliucci, *J Clin Pharmacol* 41(8):870-9 (2001) and Di Stasi, *N Engl J Med* 365:1673-83 (2011). iCasp9+AP1903 were used successfully in humans to treat GvHD after allogeneic T cell transplant. Di Stasi, *N Engl J Med* 365:1673-83 (2011).

Within certain embodiments, a polynucleotide encoding a self-activating caspase, such as a self-activating Caspase 9 (saCasp9), may be employed wherein expression of the caspase polynucleotide is under the regulatory control of a factor that is active in a target cell population, such as a senescent cell population or a cancer cell population. Self-activating caspases activate in the absence of a chemical inducer of dimerization (CID). Cells expressing self-activating caspases, such as saCasp9, apoptose almost immediately. It will be appreciated by those of skill in the art that such self-activating caspases may be advantageously employed for the induction of apoptosis in a rapidly dividing cell, such as a rapidly dividing tumor cell, where an inducible caspase protein would be diluted out before administration of a CID. Moreover, because cell death with a self-activating caspase occurs over a longer period of time as compared to an inducible caspase, the risk of tumor lysis syndrome is reduced with a self-activating caspase.

Formulations comprising a plasmid DNA encapsulated with a LNP formulation are non-toxic and non-immunogenic in animals at doses of >15 mg/kg and exhibit an efficiency in excess of 80× greater than that achievable with neutral lipid formulations and 2-5× greater than that achievable with cationic lipid formulations. LNP cargo is deposited directly into the cytoplasm thereby bypassing the endocytic pathway.

Within further aspect of these embodiments, the system further comprises one or more safety features that permit additional control over the expression of the nucleic acid within the expression construct or the functionality of a therapeutic protein encoded by the nucleic acid such as, for example, by requiring the contacting of a target cell with a chemical or biological compound that, in addition to the intracellular factor that promotes transcriptional activation of the promoter within the expression construct or promotes the functionality of the therapeutic protein, such as by promoting the dimerization of as well as inducible variants of CASP3, CASP8, CASP9, BAX, DFF40, HSV-TK, and cytosine deaminase.

A further safety element that may be employed in the expression constructs and systems of the present disclosure includes a tamoxifen-inducible Cre construct using Life Technologies Gateway Cloning Vector System employing a pDEST26 plasmid for mammalian expression. For example, a fusion protein of Cre and estrogen receptor can be constitutively expressed and induced upon the addition of tamoxifen, which permits activated Cre to re-orient the transcriptional promoter, thereby expressing the therapeutic protein.

Within yet other aspects of these embodiments, the system may further comprise a nucleic acid that encodes a detectable marker, such as a bioluminescent marker, thereby allowing the identification of cells that express the therapeutic protein and, in the case of an inducible therapeutic protein such as an inducible CASP3, CASP8, or CASP9, will be killed by the administration of a compound that promotes activity of the therapeutic protein, such as by inducing the dimerization of an inducible CASP3, CASP8, or CASP9.

Within further embodiments, the present disclosure provides methods for reducing, preventing, and/or eliminating the growth of a target cell, which methods comprise contacting a target cell with a system for the targeted production of a therapeutic protein within a target cell, wherein the system comprises a vector that is capable of delivering a nucleic acid to a cell, wherein the vector comprises an expression construct for the targeted production of a therapeutic protein within a target cell (e.g., a cell that is associated with age, disease, or other condition) but not within a non-target cell, wherein the expression construct comprises: (a) a transcriptional promoter that is activated in response to one or more factors each of which factors is produced within a target cell and (b) a nucleic acid that is operably linked to and under regulatory control of the transcriptional promoter, wherein the nucleic acid encodes a therapeutic protein that is produced upon expression of the nucleic acid and wherein production of the therapeutic protein in the target cell (i.e., the cell that is associated with age, disease, or other condition) reduces, prevents, and/or eliminates growth and/or survival of the target cell.

Within still further embodiments, the present disclosure provides methods for the treatment of an aging human or a human that is afflicted with a disease or another condition, wherein the aging, disease, or other condition is associated with a target cell within the human, the methods comprising administering to the human a system for the targeted production of a therapeutic protein within a target cell, wherein the system comprises a vector that is capable of delivering a nucleic acid to a cell, wherein the vector comprises an expression construct for the targeted production of a therapeutic protein within a target cell (e.g., a cell that is associated with age, disease, or other condition) but not within a non-target cell, wherein the expression construct comprises: (a) a transcriptional promoter that is activated in response to one or more factors each of which factors is produced within a target cell and (b) a nucleic acid that is operably linked to and under regulatory control of the transcriptional promoter, wherein the nucleic acid encodes a therapeutic protein that is produced upon expression of the nucleic acid and wherein production of the therapeutic protein in the target cell (i.e., the cell that is associated with age, disease, or other condition) reduces, prevents, and/or eliminates growth and/or survival of the target cell thereby slowing aging in the human and/or slowing, reversing, and/or eliminating the disease or condition in the human.

These and other related aspects of the present disclosure will be better understood in light of the following drawings and detailed description, which exemplify certain aspects of the various embodiments.

BRIEF DESCRIPTION OF THE DRAWINGS

FIG. 3 is a table comparing the reported maximum tolerated dose (MTD) for clinical stage lipid-based in vivo delivery technologies. The MTD of >15 m/kg for fusogenic lipid nanoparticles of the present disclosure was estimated from rat toxicity data.

FIG. 7 presents data obtained in mice that were administered intravenously Fusogenix lipid nanoparticles labeled with $^{64}$Cu-NOTA [1,4,7-triazacyclononane-1,4,7-triacetic acid]. See, Fournier, *FJNMMI Research* 2:8 (2012). $^{64}$Cu was detected via positron emission tomography (PET).

FIG. 10) and of anti-p14 and anti-LNP antibody responses (FIG. 11), which demonstrate the safety and tolerability of exemplary fusogenic lipid nanoparticles utilizing a reptilian reovirus p14 FAST fusion protein (Fusogenix™). As shown, virtually no antibody response was observed in immune competent mice (with and without adjuvant).

DETAILED DESCRIPTION

Figure 1:
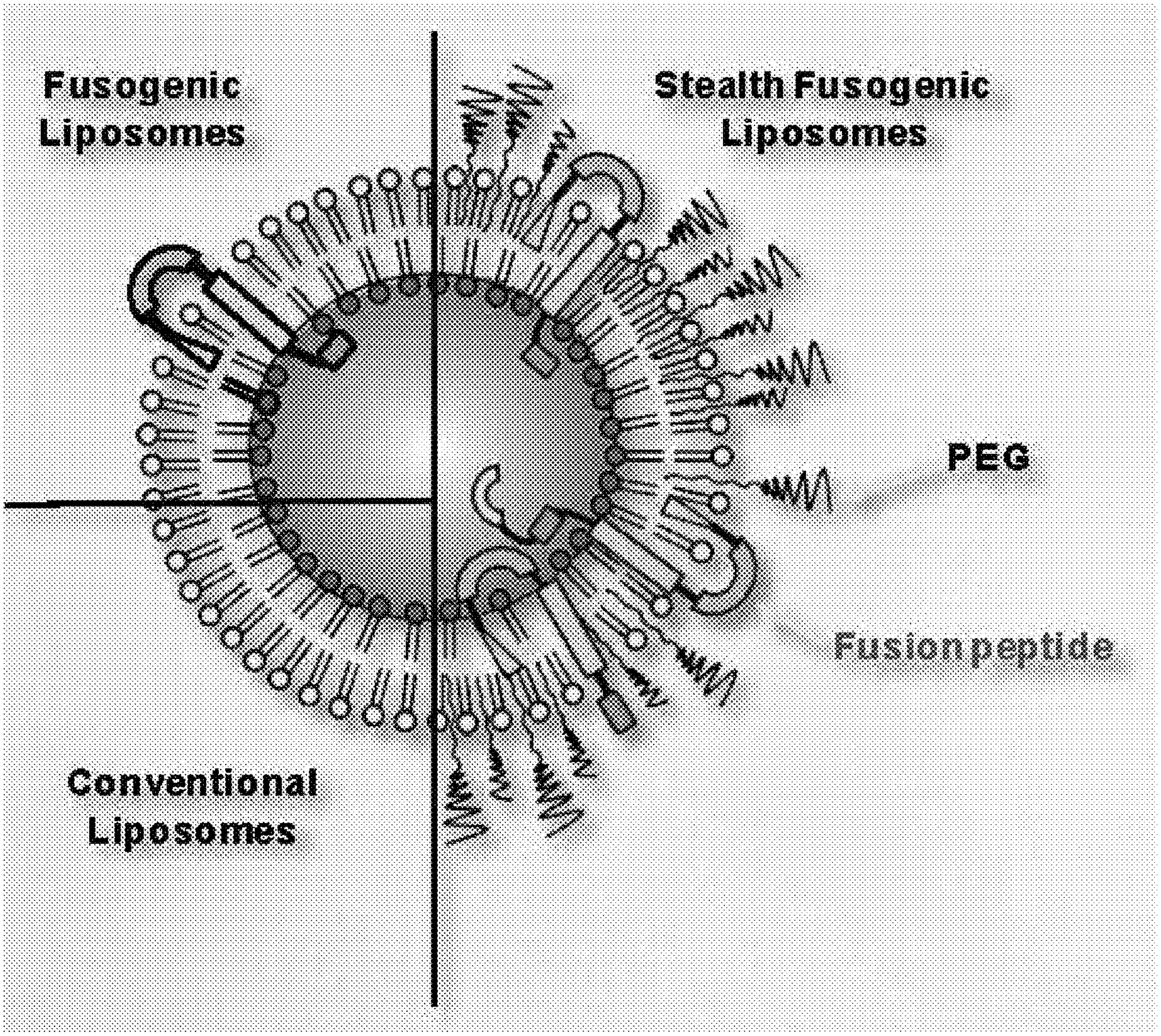
FIG. 1 is a diagrammatic representation of conventional and fusogenic liposomes, including stealth fusogenic liposomes, including lipid nanoparticles employing Innovascreen's Fusogenix™ Platform according to certain aspects of the present disclosure. Shown are Fusogenix™ lipid nanoparticles utilizing a p14 FAST fusion protein from reptilian reovirus and including a plasmid vector encoding an inducible Caspase 9 (iCasp9) under a promoter that is active in a target cell population, such as a senescent target cell population or a cancer target cell population. Exemplified in this diagram are Casp9 fusion peptides that are activated via a small molecule dimerizer such as AP1903.
Figure 2:
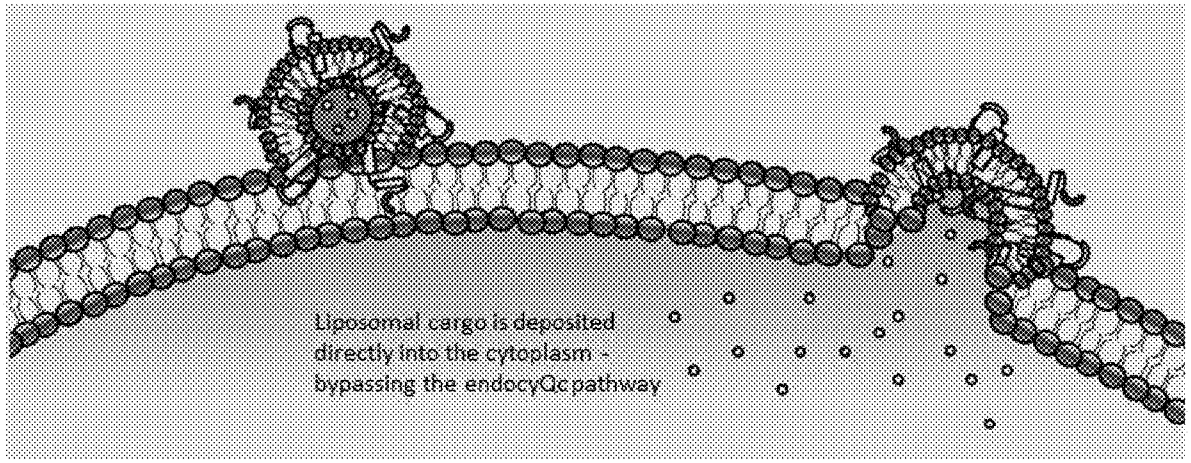
FIG. 2 is a diagrammatic representation of the liposomal delivery to the cytoplasm of a target cell, according to certain aspects of the present disclosure. Shown are Fusogenix™ lipid nanoparticles (LNPs) that are configured for the delivery of nucleic acids, such as those encoding a pro-apoptotic protein, such as Caspase 9, under the regulatory control of a target cell-specific transcriptional promoter, such as a target senescent cell encoding p16 or a target cancer cell encoding p53. Exemplified are Fusogenix™ lipid nanoparticles comprising a p14 FAST protein to catalyze the rapid lipid mixing between the lipid nanoparticle (LNP) and the target cell plasma membrane. Such Fusogenix™ lipid nanoparticles (i) deliver the cargo nucleic acids directly into the cytoplasm thereby bypassing the endocytic pathway, (ii) are non-toxic (i.e., non-immunogenic) in animals at doses of ≥15 mg/kg, (iii) are 80× more efficient than neutral lipid formulations, (iv) are 2-5× more efficient than cationic lipid formulations, and (iv) are manufacturable at scale.
Figure 4:
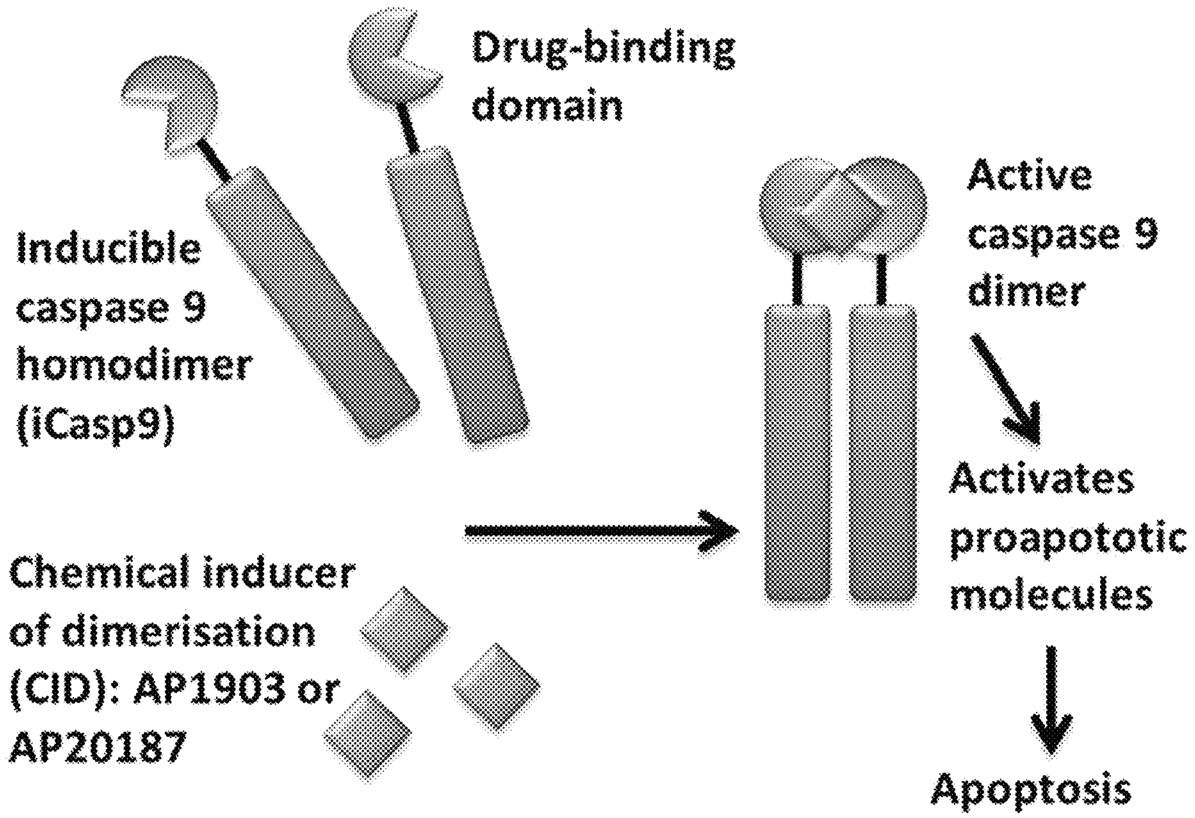
FIG. 4 is a diagrammatic representation of the induction of an inducible Caspase 9 homodimer (iCasp9), which iCasp9 is a fusion protein comprising a drug-binding domain for binding to a chemical inducer of dimerization (CID) and an active portion of Caspase 9. A CID, as exemplified by CIDs designated AP1903 and AP20187, binds to the drug-binding domain of the iCasp9 fusion protein to dimerize and, thereby, activate iCasp9, which results in the intracellular activation of pro-apoptotic molecules and the induction of apoptosis within a target cell.
Figure 5:
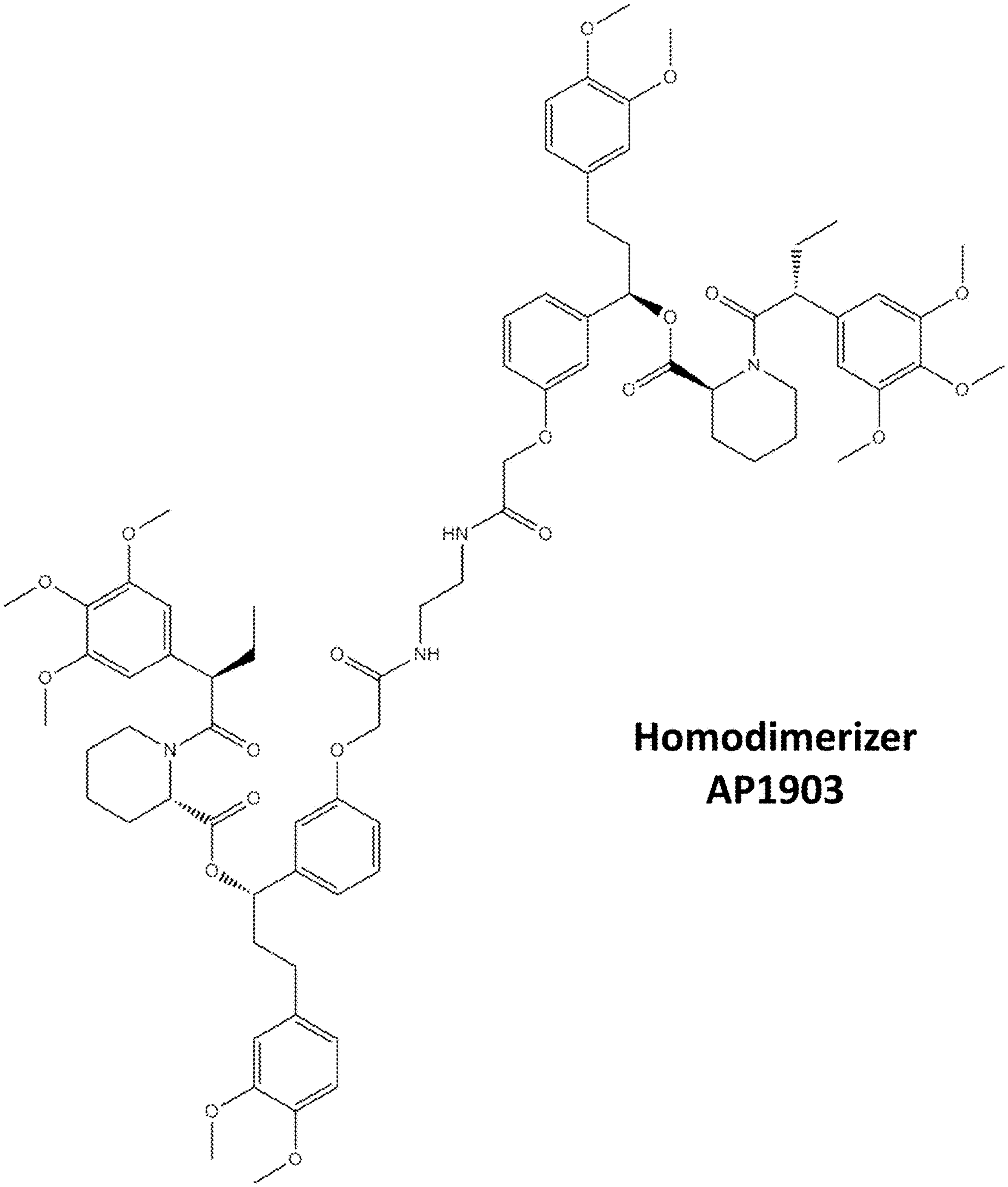
FIG. 5 depicts the chemical structure of an exemplary chemical inducer of dimerization (CID), which is a homodimerizer designated herein as AP1903 (APExBIO, Houston, Tex.) that may be employed in various embodiments of the present disclosure for inducing the activity of an inducible pro-apoptotic protein, such as an inducible caspase protein (e.g., iCasp9).
Figure 6:
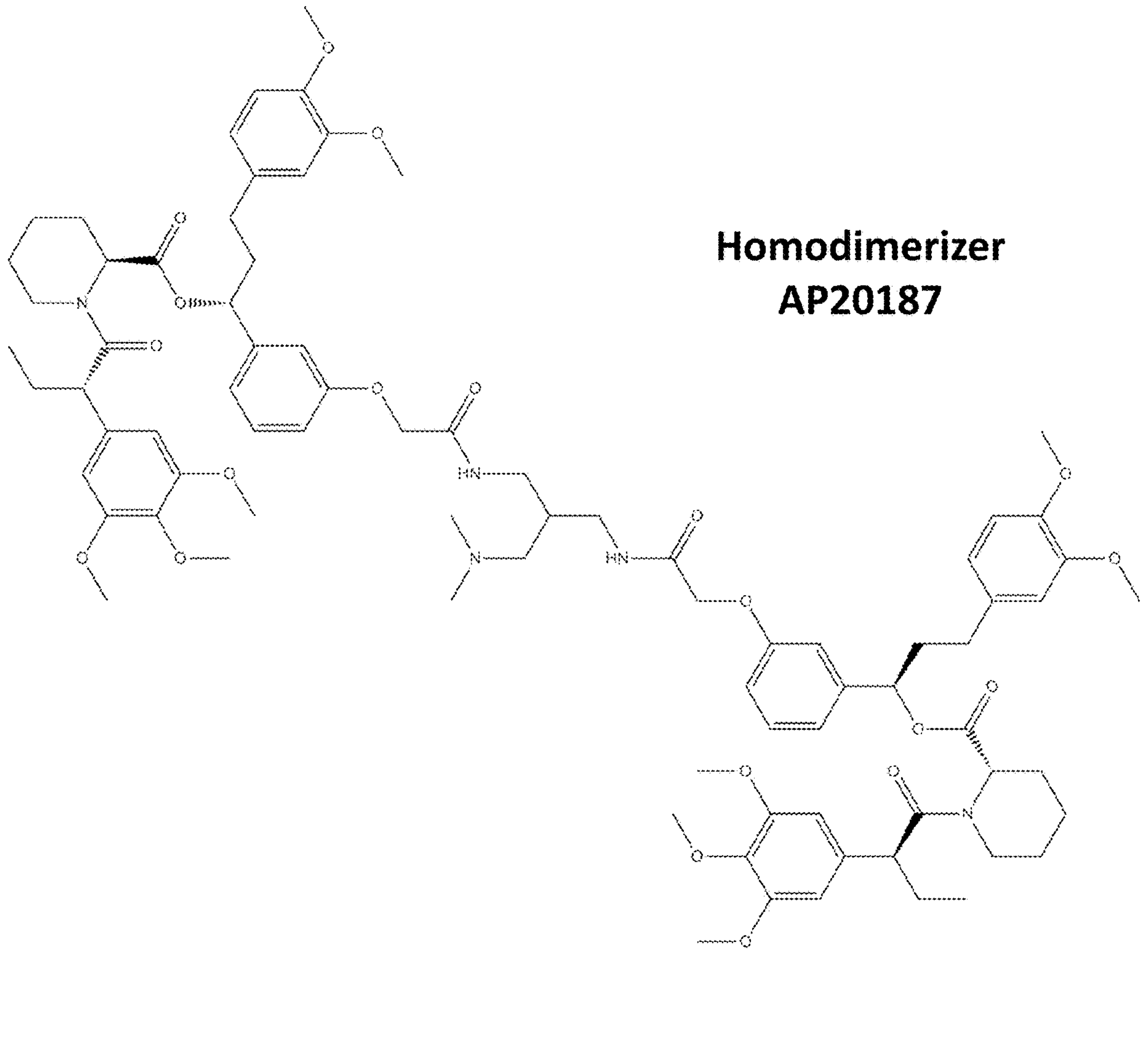
FIG. 6 depicts the chemical structure of an exemplary chemical inducer of dimerization (CID), which is a homodimerizer designated herein as AP20187 (APExBIO, Houston, Tex.) that may be employed in various embodiments of the present disclosure for inducing the activity of an inducible pro-apoptotic protein, such as an inducible caspase protein (e.g., iCasp9).

The present disclosure provides expression cassettes, systems, and methods for the selective reduction, prevention, and/or elimination in the growth and/or survival of a cell that is associated with aging, disease, or another condition (collectively "a target cell"), which expression cassettes, systems, and methods overcome the safety and efficacy concerns that are associated with existing technologies that rely on targeted delivery of a therapeutic compound and, as a result of, for example, inefficient target cell delivery and/or off-target effects, have limited therapeutic benefit.

More specifically, the expression cassettes, systems, and methods disclosed herein exploit the cell-specific transcription regulatory machinery that is intrinsic to a target cell and, thereby, achieve a target cell-specific therapeutic benefit without the need for targeted-delivery of a therapeutic compound. These expression cassettes, systems, and methods permit the target cell-specific induction of expression of a nucleic acid that encodes a therapeutic protein, which protein can reduce, prevent, and/or eliminate the growth and/or survival of a cell in which it is produced.

Thus, the various embodiments that are provided by the present disclosure include:

1. Expression constructs for the targeted production of therapeutic proteins within a target cell, such as a cell that is associated with aging, disease, and/or another condition, the expression construct comprising:
   a. transcriptional promoter that is activated in response to one or more factors each of which is produced within a target cell and
   b. a nucleic acid that is operably linked to and under regulatory control of the transcriptional promoter, wherein the nucleic acid encodes a therapeutic protein that can reduce, prevent, and/or eliminate the growth and/or survival of a cell, including the target cell.
2. Systems for the targeted production of a therapeutic protein within a target cell, the systems comprising a vector for delivering a nucleic acid to a cell, including a target cell as well as a non-target cell, wherein the vector comprises an expression construct for the targeted production of a therapeutic protein within a target cell (e.g., a cell that is associated with aging, cancer, and/or other disease and/or condition) but not within a non-target cell, wherein the expression construct comprises (i) a transcriptional promoter that is activated in response to one or more factors each of which is produced within a target cell and (ii) a nucleic acid that is operably linked to and under regulatory control of the transcriptional promoter, wherein the nucleic acid encodes a therapeutic protein that can reduce, prevent, and/or eliminate the growth and/or survival of a cell in which it is produced, including a target cell.

3. Methods for reducing, preventing, and/or eliminating the growth of a target cell, the methods comprising contacting a target cell with a system for the targeted production of a therapeutic protein within a target cell, wherein the system comprises a vector for delivery of a nucleic acid to a cell, wherein the vector comprises an expression construct for the targeted production of a therapeutic protein within a target cell (e.g., a cell that is associated with age, disease, or other condition) but not within a non-target cell, wherein the expression construct comprises (i) a transcriptional promoter that is activated in response to one or more factors each of which factors is produced within a target cell and (ii) a nucleic acid that is operably linked to and under regulatory control of the transcriptional promoter, wherein the nucleic acid encodes a therapeutic protein that is produced upon expression of the nucleic acid and wherein production of the therapeutic protein in the target cell (i.e., the cell that is associated with age, disease, or other condition) reduces, prevents, and/or eliminates growth and/or survival of the target cell.

4. Methods for the treatment of aging, disease, or other condition in a human, wherein aging, disease, or other condition is associated with a target cell, the methods comprising administering to the human a system for the targeted production of a therapeutic protein within a target cell, wherein the system comprises a vector that is capable of delivering a nucleic acid to a cell, wherein the vector comprises an expression construct for the targeted production of a therapeutic protein within a target cell (e.g., a cell that is associated with age, disease, or other condition) but not within a non-target cell, wherein the expression construct comprises (i) a transcriptional promoter that is activated in response to one or more factors each of which factors is produced within a target cell and (ii) a nucleic acid that is operably linked to and under regulatory control of the transcriptional promoter, wherein the nucleic acid encodes a therapeutic protein that is produced upon expression of the nucleic acid and wherein production of the therapeutic protein in the target cell (i.e., the cell that is associated with age, disease, or other condition) reduces, prevents, and/or eliminates growth and/or survival of the target cell thereby slowing aging in the human and/or slowing, reversing, and/or eliminating the disease or condition in the human.

Definitions

These and other aspects of the present disclosure can be better understood by reference to the following non-limiting definitions.

As used herein, the term "transcriptional promoter" refers to a region of DNA that initiates transcription of a particular gene. Promoters are located near transcription start sites of genes, on the same strand and upstream on the DNA (towards the 3' region of the anti-sense strand, also called template strand and non-coding strand). Promoters can be about 100-1000 base pairs long. For the transcription to take place, the enzyme that synthesizes RNA, known as RNA polymerase, must attach to the DNA near a gene. Promoters contain specific DNA sequences and response elements that provide a secure initial binding site for RNA polymerase and for proteins called transcription factors that recruit RNA polymerase. These transcription factors have specific activator or repressor sequences of corresponding nucleotides that attach to specific promoters and regulate gene expressions. The process is more complicated, and at least seven different factors are necessary for the binding of an RNA polymerase II to the promoter. Promoters represent critical elements that can work in concert with other regulatory regions (enhancers, silencers, boundary elements/insulators) to direct the level of transcription of a given gene.

Eucaryotic transcriptional promoters comprise a number of essential elements, which collectively constitute a core promoter (i.e., the minimal portion of a promoter that is required to initiate transcription). Those elements include (1) a transcription start site (TSS), (2) an RNA polymerase binding site (in particular an RNA polymerase II binding site in a promoter for a gene encoding a messenger RNA), (3) a general transcription factor binding site (e.g., a TATA box having a consensus sequence TATAAA, which is a binding site for a TATA-binding protein (TBP)), (4) a B recognition element (BRE), (5) a proximal promoter of approximately 250 bp that contains regulatory elements, (6) transcription factor binding sites (e.g., an E-box having the sequence CACGTF, which is a binding site for basic helix-loop-helix (bHLH) transcription factors including BMAL11-Clock nad cMyc), and (7) a distal promoter containing additional regulatory elements. As used herein, the term "transcriptional promoter" is distinct from the term "enhancer," which refers to a regulatory element that is distant from the transcriptional start site.

Eucaryotic promoters are often categorized according to the following classes: (1) AT-based class, (2) CG-based class, (3) ATCG-compact class, (4) ATCG-balanced class, (5) ATCG-middle class, (6) ATCG-less class, (7) AT-less class, (8) CG-spike class, (9) CG-less class, and (10) ATspike class. Sec, Gagniuc and Ionescu-Tirgoviste, *BMC Genomics* 13:512 (2012). Eucaryotic promoters can be "unidirectional" or "bidirectional." Unidirectional promoters regulate the transcription of a single gene and are characterized by the presence of a TATA box. Bidirectional promoters are short (<1 kbp), intergenic regions of DNA between the 5' ends of genes in a bidirectional gene pair (i.e., two adjacent genes coded on opposite strands having 5' ends oriented toward one another. Bidirectional genes are often functionally related and because they share a single promoter, can be co-regulated and co-expressed. Unlike unidirectional promoters, bidirectional promoters do not contain a TATA box but do contain GpC islands and exhibit symmetry around a midpoint of dominant Cs and As on one side and Gs and Ts on the other. CCAAT boxes are common in bidirectional promoters as are NRF-1, GABPA, YY1, and ACTACAnnTCCC motifs.

Transcriptional promoters often contain two or more transcription factor binding sites. Thus, the efficient expression of a nucleic acid that is downstream of a promoter having multiple transcription factor binding sites typically requires the cooperative action of multiple transcription factors. Accordingly, the specificity of transcriptional regulation, and hence expression of an associated nucleic acid, can be increased by employing transcriptional promoters having two or more transcription factor binding sites.

As used herein, the term "transcription factor" refers to sequence-specific DNA-binding factors that bind to specific sequences within a transcriptional promoter thereby regulating the transcription of a nucleic acid that is in operable proximity to and downstream of the promoter. Transcription factors include activators, which promote transcription, and repressors, which block transcription by preventing the recruitment or binding of an RNA polymerase. Transcription factors typically contain (1) one of more DNA-binding domains (DBDs), which facilitate sequence specific binding to a cognate transcription factor binding site (a/k/a response element) within a transcriptional promoter; (2) one or more signal-sensing domains (SSDs), which includes ligand binding domains that are responsive to external signals; and (3) one or more transactivation domains (TADs), which contain binding sites for other proteins, including transcription coregulators.

As used herein, the term "transcription factor" refers exclusively to those factors having one or more DBDs and is not intended to include other regulatory proteins such as coactivators, chromatin remodelers, histone acetylases, deacetylases, kinases, and methylases, which no not contain DBDs.

Of the approximately 2,600 human proteins that contain DNA-binding domains, the majority are believed to be transcription factors. Transcription factors are categorized according to structural features of the DNA-binding domain, which include basic helix-loop-helix domains, basic-leucine zipper (bZIP domains), C-terminal effector domains of bipartite response regulators, GCC box domains, helix-turn-helix domains, homeodomains, lambda repressor-like domains, serum response factor-like (srf-like) domains, paired box domains, winged helix domains, zinc finger domains, multi-$Cys_2His_2$ zinc finger domains, $Zn_2Cys_6$ domains, and $Zn_2Cys_8$ nuclear receptor zinc finger domains.

Many transcription factors are either tumor suppressors or oncogenes, and, thus, mutations within and the aberrant expression of such transcription factors is associated with some cancers and other diseases and conditions. For example, transcription factors within (1) the NF-kappaB family, (2) the AP-1 family, (3) the STAT family, and (4) the steroid receptor family have been implicated in the neurodevelopmental disorder Rett syndrome (the MECP2 transcription factor), diabetes (hepatocyte nuclear factors (HNFs) and insulin promoter factor-1 (IPF1/Pdx1)), developmental verbal dyspraxia (the FOXP2 transcription factor), autoimmune diseases (the FOXP3 transcription factor), Li-Raumeni syndrome (the p53 tumor suppressor), and multiple cancers (the STAT and HOX family of transcription factors). Clevenger, *Am. J. Pathol.* 165(5):1449-60 (2004); Carrithers et al., *Am J Pathol* 166(1): 185-196 (2005); Herreros-Villanueve et al., *World J Gastroenterology* 20(9):2247-2254 (2014); and Campbell et al., *Am J Pathol* 158(1):25-32 (2001). Olsson et al., *Oncogene* 26(7): 1028-37 (2007) describe the upregulation of the transcription factor E2F3, which is a key regulator of the cell cycle, in human bladder and prostate cancers. Cantile et al., *Curr Med Chem* 18(32):4872-84 (2011) describe the upregulation of HOX genes in urogenital cancers; Cillo et al., *Int J. Cancer* 129(11):2577-87 (2011) describe the upregulation of HOX genes in hepatocellular carcinoma; Cantile et al., *Int J. Cancer* 125(7):1532-41 (2009) describe HOX D13 expression across 79 rumor tissue types; Cantile et al., *J Cell Physiol* 205(2):202-10 (2005) describe upregulation of HOX D expression in prostate cancers; Cantile et al., *Oncogene* 22(41):6462-8 (2003) describe the hyperexpression of locus C genes in the HOX network in human bladder transitional cell carcinomas; Morgan et al., *BioMed Central* 14:15 (2014), describe HOX transcription factors as targets for prostate cancer; and Alharbi et al. *Leukemia* 27(5):1000-8 (2013) describe the role of HOXC genes in hematopoiesis and acute leukemia.

The AP-2 family includes five transcription factors that can act as both repressors and activators. AP-2γ regulates cancer cell survival by blocking p53 activation of the p21CIP gene. High levels of AP-2γ are associated with poor prognosis in breast cancer. Gee et al., *J Pathol* 217(1):32-41 (2009) and Williams et al., *EMBO J* 28(22):3591-601 (2009). A further transcription factor that promotes cell survival are the forkhead transcription factors (FOX), which can promote the expression of proteins involved in drug resistance and also block programmed cell death and may therefore protect cancer cells from chemotherapeutic drugs. Gomes et al., *Chin J. Cancer* 32(7):365-70 (2013) describe the role of FOXO3a and FOXM1 in carcinogenesis and drug resistance.

Transcription factors can bind to promoters as well as to enhancers. As used in the present disclosure, the term transcription factor refers to the subset of transcription factors that bind to transcription factor binding sites within a promoter and excludes those factors that bind to enhancer sequences. Transcription factors can also upregulate or downregulate the expression of an associated nucleic acid. The present disclosure employs transcriptional promoters having transcription factor binding sites for transcription factors that promote rather than inhibit expression and therefore cause the upregulation in the expression of an associated nucleic acid. Such transcription factors that upregulate nucleic acid expression include, for example and not limitation, transcription factors that (1) stabilize RNA polymerase binding to its cognate binding site, (2) recruit coactivator or corepressor proteins to a transcription factor DNA complex, and/or (3) catalyze the acetylation of histone proteins (or recruit one or more other proteins that catalyze the acetylation of histone proteins). Such histone acetyltransferase (HAT) activity reduces the affinity of histone binding to DNA thereby making the DNA more accessible for transcription.

As used herein, the term “necrosis” refers to a process leading to cell death that occurs when a cell is damaged by an external force, such as poison, a bodily injury, an infection, or loss of blood supply. Cell death from necrosis causes inflammation that can result in further distress or injury within the body. As used herein, the term “apoptosis” refers to a process leading to cell death in which a programmed sequence of events leads to the elimination of cells without releasing harmful substances. Apoptosis plays a crucial role in developing and maintaining the health of the body by eliminating old cells, unnecessary cells, and unhealthy cells. Apoptosis is mediated by proteins produced by suicide genes, including the caspase proteins, which break down cellular components needed for survival and induce the production of DNAses, which destroy nuclear DNA.

As used herein, the term “suicide gene” refers to a class of genes that produce proteins that induce p53-mediated apoptotic cell killing. Suicide genes that can be employed in the expression constructs and systems of the present disclosure include the caspases, CASP3, CASP8, CASP9, BAX, DFF40, Herpes Simplex Virus Thymidine Kinase (HSV-TK), and cytosine deaminase and inducible variants of CASP3, CASP8, CASP9, BAX, DFF40, Herpes HSV-TK, and cytosine deaminase.

The presently disclosed expression constructs and systems are used in methods for the treatment of aging, cancer infectious disease, bacterial infections, and/or other conditions as well as in methods for the killing of cells that are associated with aging, cancer, infectious disease, bacterial infections, and/or other conditions and employ a therapeutic protein that reduces the growth and/or proliferation of a target cell. In certain embodiments, the therapeutic protein can be expressed by a suicide gene, which encodes CASP3, CASP8, CASP9, BAX, DFF40, HSV-TK, or cytosine deaminase as well as a inducible variants of CASP3, CASP8, CASP9, BAX, DFF40, HSV-TK, or cytosine deaminase. The expression cassettes and systems can also be used in conjunction with conventional chemotherapeutics to enhance the effectiveness of therapeutic regimen for the treatment of aging, cancers, infectious diseases, bacterial infections, and other diseases and conditions.

Figure 14:
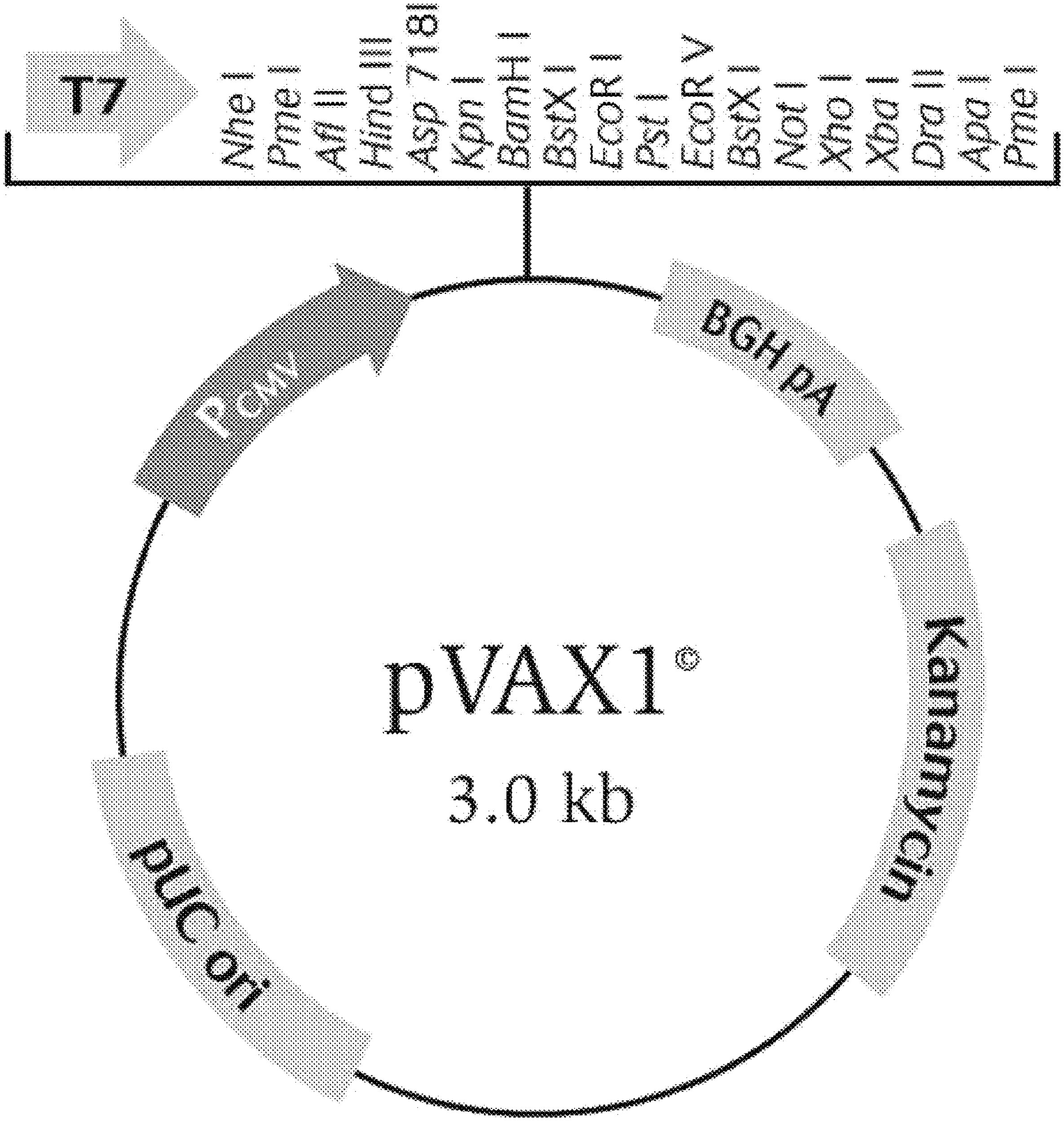
FIG. 14 is a restriction map of the plasmid vector pVAX1™ which is employed in certain aspects of the expression constructs, systems, formulations, and methods of the present disclosure for the target cell-specific production of a therapeutic protein, such as a pro-apoptotic protein, including a caspase protein, such as Caspase 9, as well as inducible and self-activating variants of a pro-apoptotic protein, including inducible and self-activating variants of caspase proteins, such as inducible Caspase 9 (iCasp9) and self-activating Caspase 9 (saCasp9). In certain embodiments, expression constructs and formulations may additionally include a safety element, such as a tamoxifen-inducible Cre construct (e.g., Life Technologies Gateway Cloning Vector System). A fusion protein of Cre and estrogen receptor is constitutively expressed and induced upon the addition of tamoxifen, which permits activated Cre to re-orient the p16-promoter, thereby expressing caspase 9 or inducible/self-activating variant thereof, pVAX1 is commercially available from ThermoFisher Scientific (Waltham, Mass.).
Figure 15:
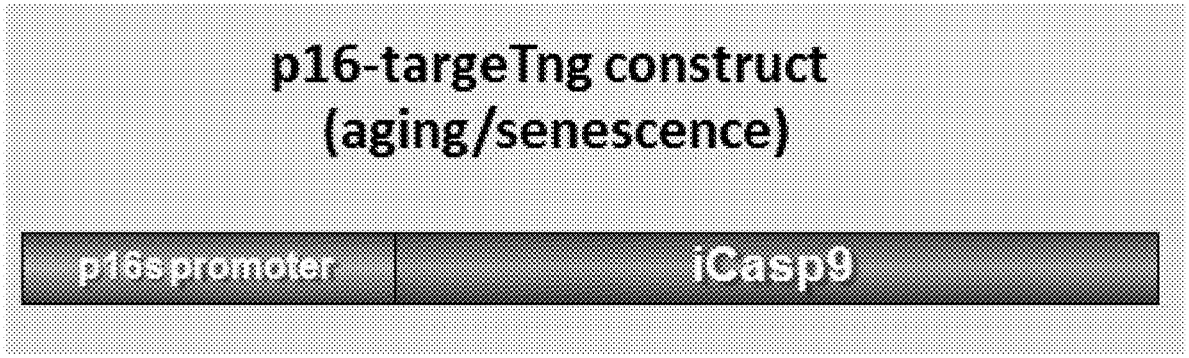
FIG. 15 is a diagrammatic representation of an exemplary p16-targeting construct for the target cell-specific expression of an inducible Caspase 9 (iCasp9) protein in target cells expressing p16, such as target cells that are associated with aging and/or senescence, which p16-targeting construct comprises a p16s transcriptional promoter in operable connection to iCasp9. An exemplary p16 transcriptional promoter is described in Baker et al., *Nature* 479(7372):232-67 (2011)).

Within certain aspects of the present disclosure, expression constructs are pVAX1 (FIG. 14) plasmid expression constructs comprising a polynucleotide encoding a pro-apoptotic protein under the regulatory control of a target cell-specific promoter, such as a senescent cell-specific promoter or a cancer cell-specific promoter.

Figure 16:
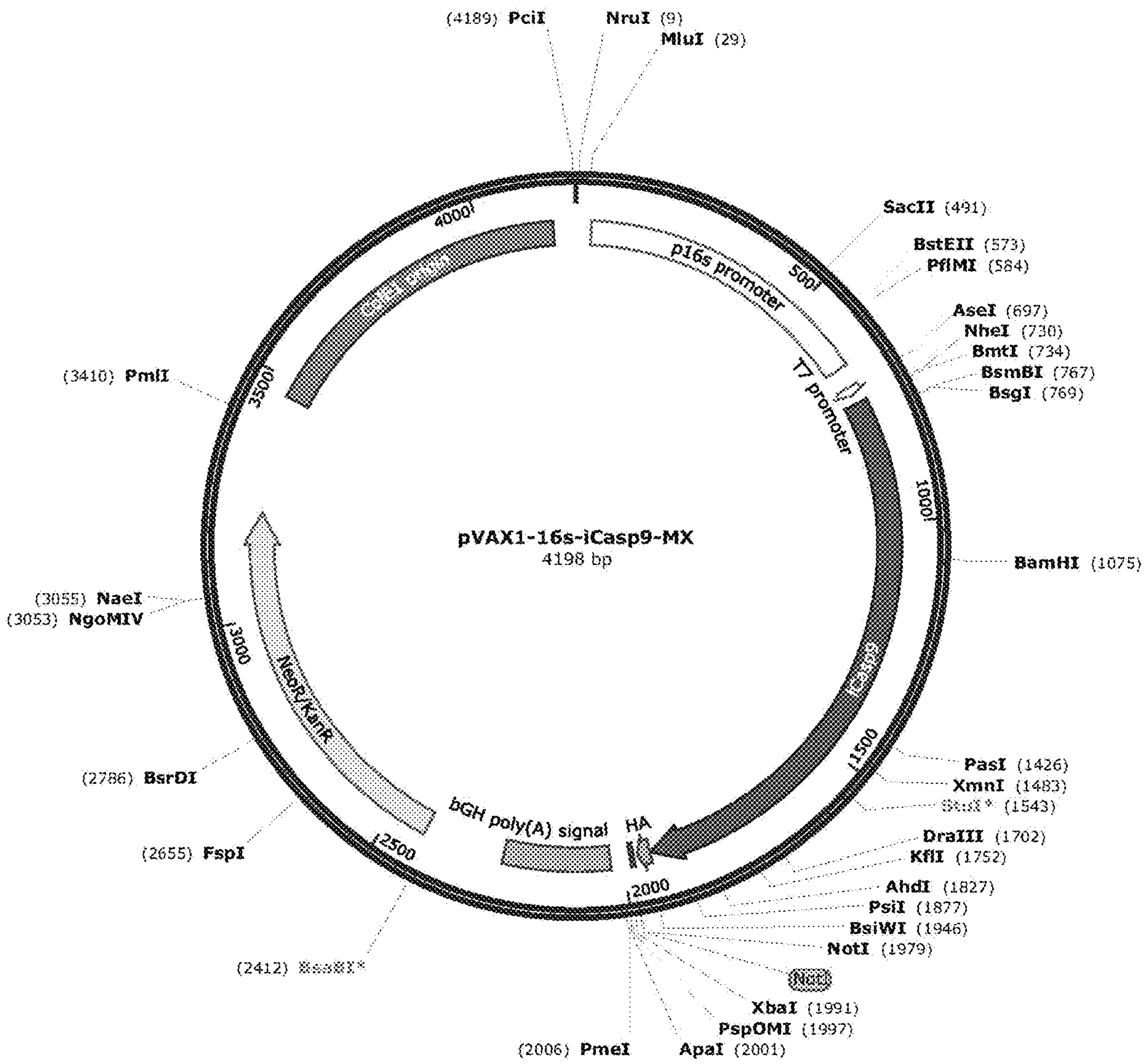
FIG. 16 is a restriction map of the plasmid vector pVAX1-16s-iCasp9-MX (SEQ ID NO: 6), which comprises an exemplary p16-targeting construct for the target cell-specific expression of an inducible Caspase 9 (iCasp9) protein in target cells expressing p16, such as target cells that are associated with aging and/or senescence, which p16-targeting construct comprises a p16s transcriptional promoter in operable connection to iCasp9.
Figure 26:
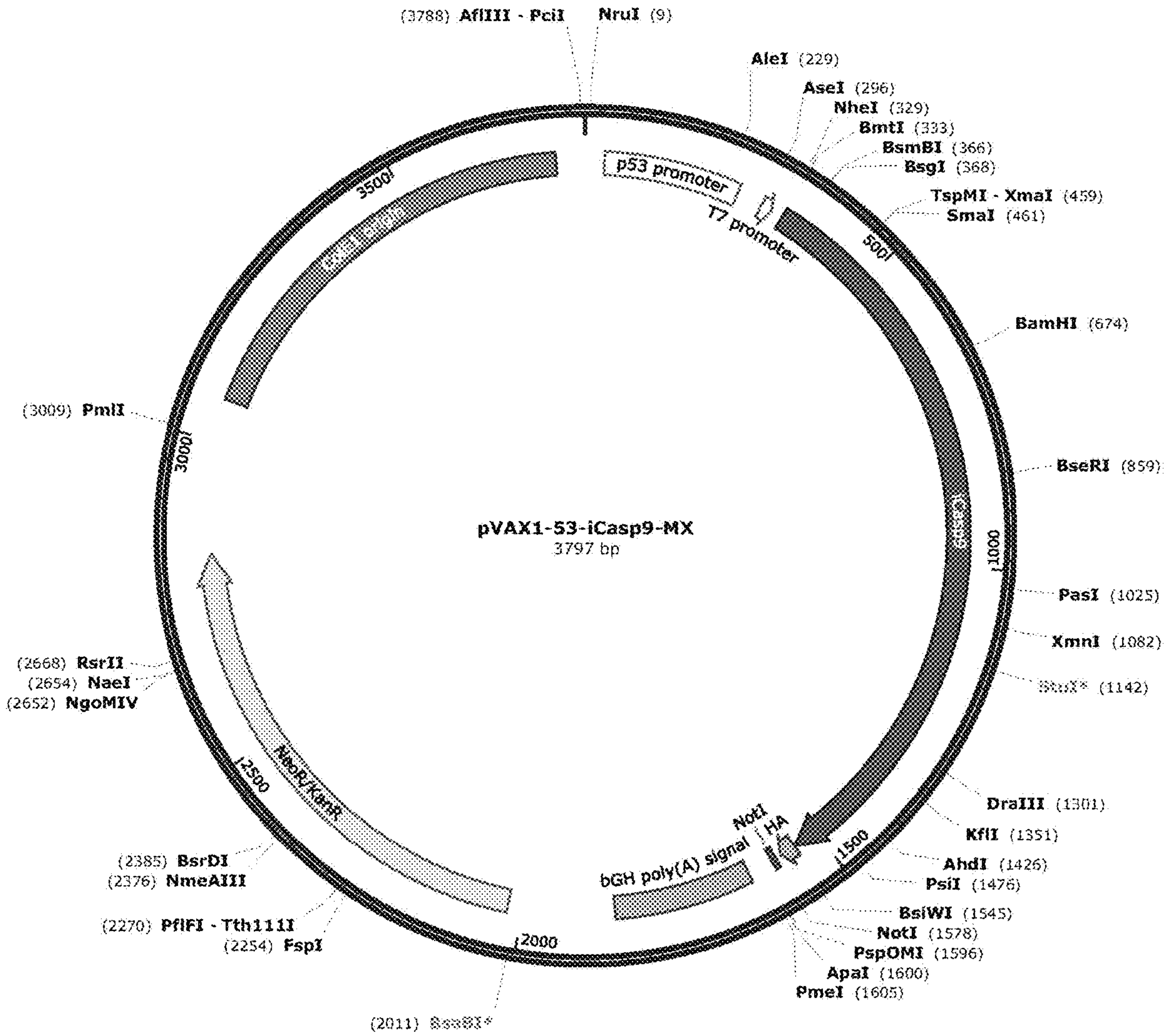
FIG. 26 is a restriction map of a plasmid (pVAX1-p53-iCasp9-MX; SEQ ID NO: 7) comprising a p53-targeting cassette as depicted in FIG. 25. Expression of an iCasp9 nucleic acid encoding an inducible Casp9 protein is regulated by the p53 transcriptional promoter.
Figure 27:
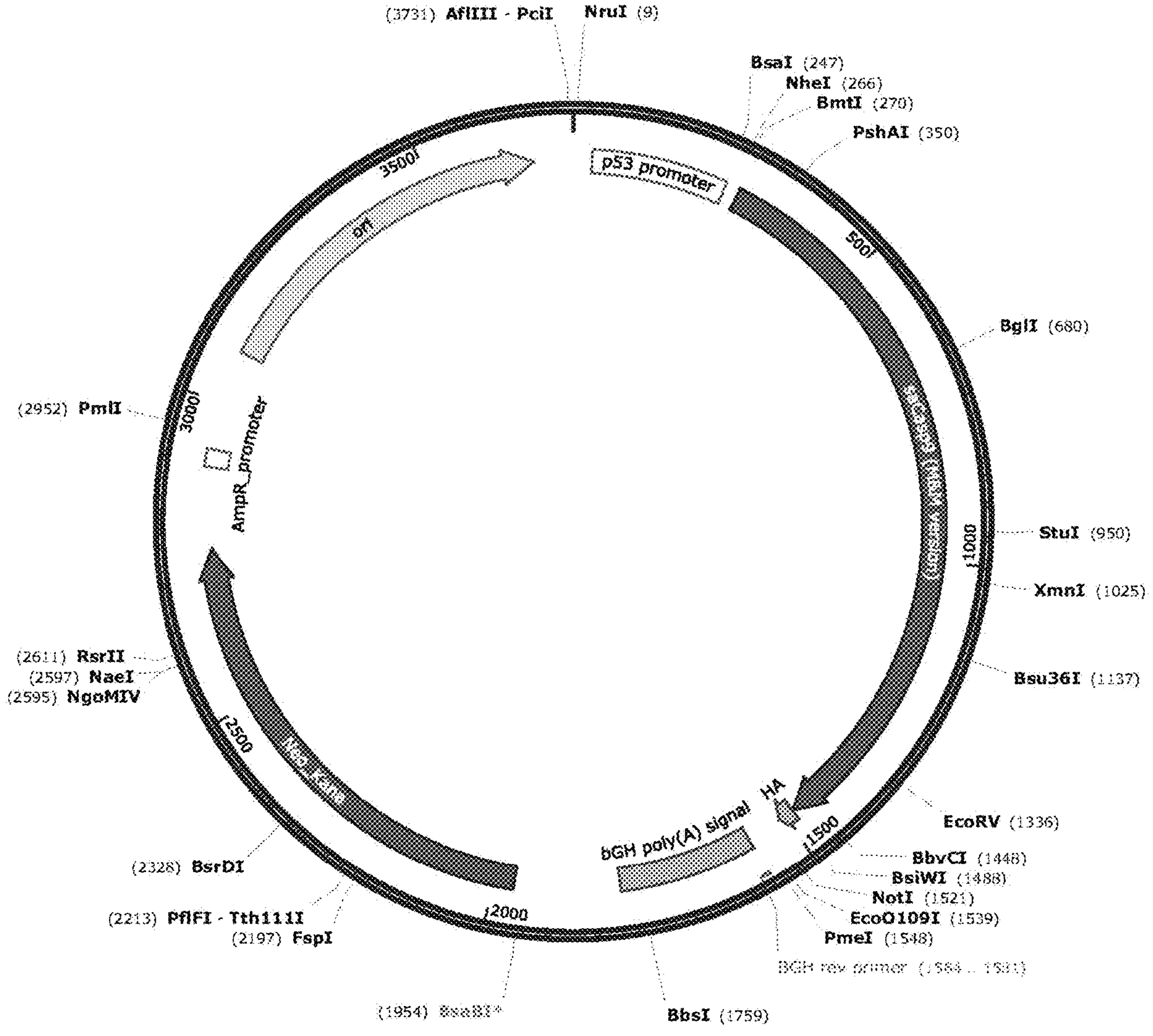
FIG. 27 is a restriction map of a plasmid (pVAX1-p53-saCasp9; SEQ ID NO: 8) comprising a p53-targeting cassette. Expression of a nucleic acid encoding a self-activating Caspase 9 (saCasp9) protein is regulated by the p53 transcriptional promoter.
Figure 28:
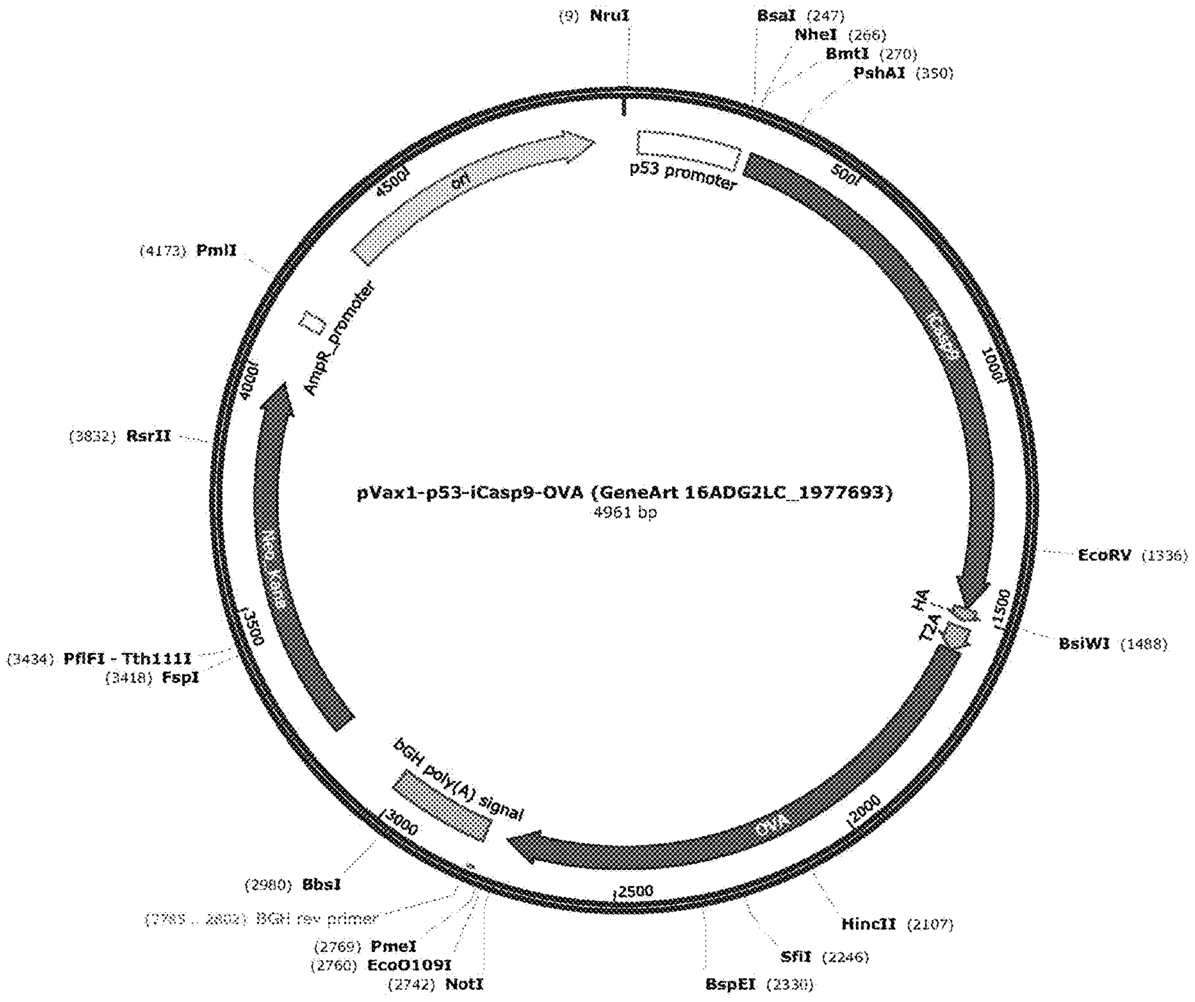
FIG. 28 is a restriction map of a plasmid (pVAX1-p53-iCasp9-OVA; SEQ ID NO: 11) comprising a p53-targeting cassette as depicted in FIG. 25. Expression of a nucleic acid encoding an inducible Casp9 protein is regulated by the p53 transcriptional promoter.
Figure 29:
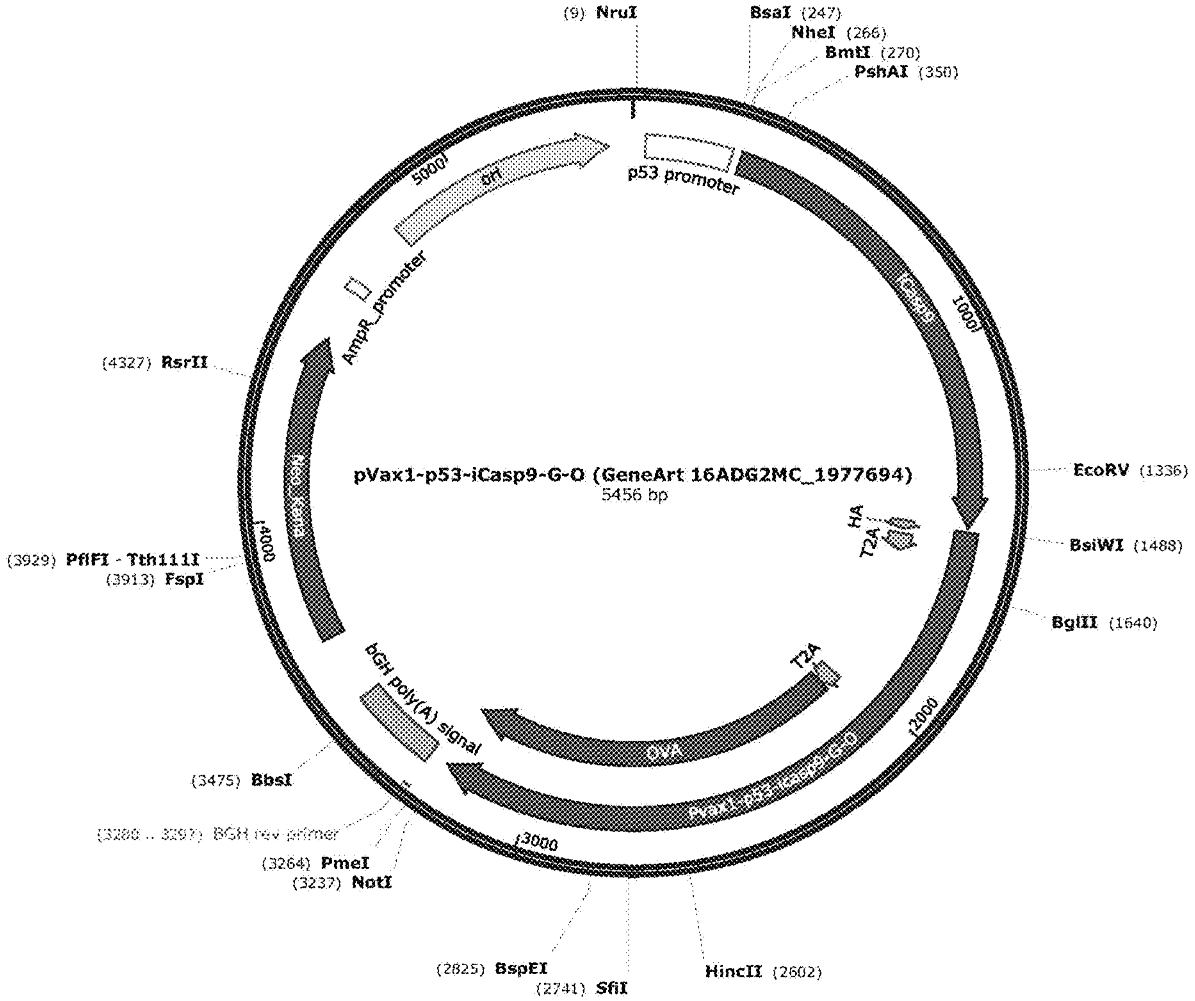
FIG. 29 is a restriction map of a plasmid (pVAX1-p53-iCasp9-G-O; SEQ ID NO: 9) comprising a p53-targeting cassette as depicted in FIG. 25. Expression of an iCasp9 nucleic acid encoding an inducible Casp9 protein is regulated by the p53 transcriptional promoter.
Figure 30:
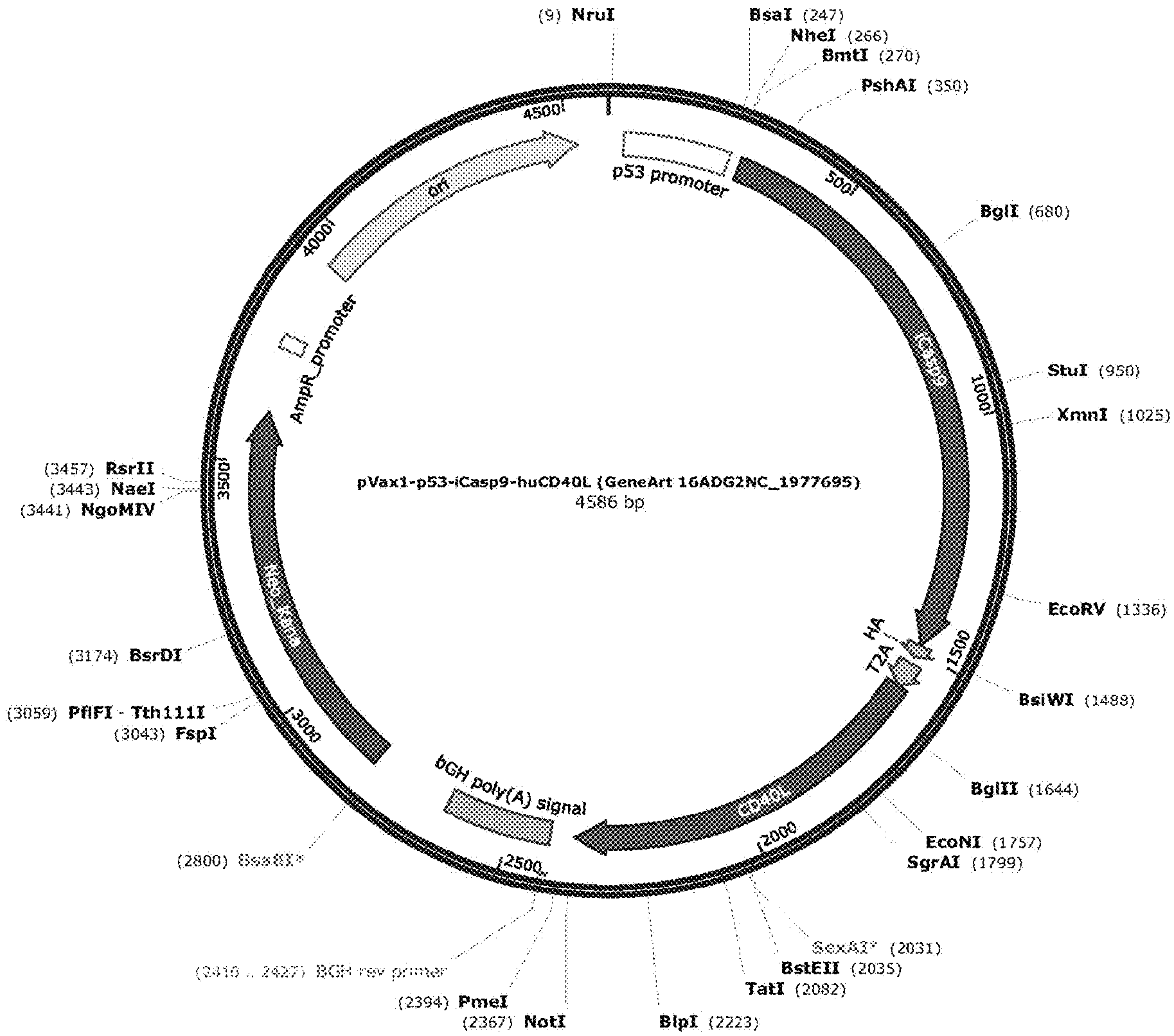
FIG. 30 is a restriction map of a plasmid (pVAX1-p53-iCasp9-huCD40L; SEQ ID NO: 10) comprising a p53-targeting cassette as depicted in FIG. 25. Expression of an iCasp9 nucleic acid encoding an inducible Casp9 protein is regulated by the p53 transcriptional promoter. Additional targeting cassettes and plasmid constructs have been developed for advanced oncology applications, as disclosed herein, which constructs employ nucleic acids encoding, for example, one or more immunostimulatory cytokines (such as huCD40L, as shown in FIG. 30, as well as GMCSF and IL12) and/or one or more antigens (such as chicken ovalbumin (OVA), as shown in FIG. 28, as well as Nt1, tetanus antigens, and influenza antigens).
Figure 31:
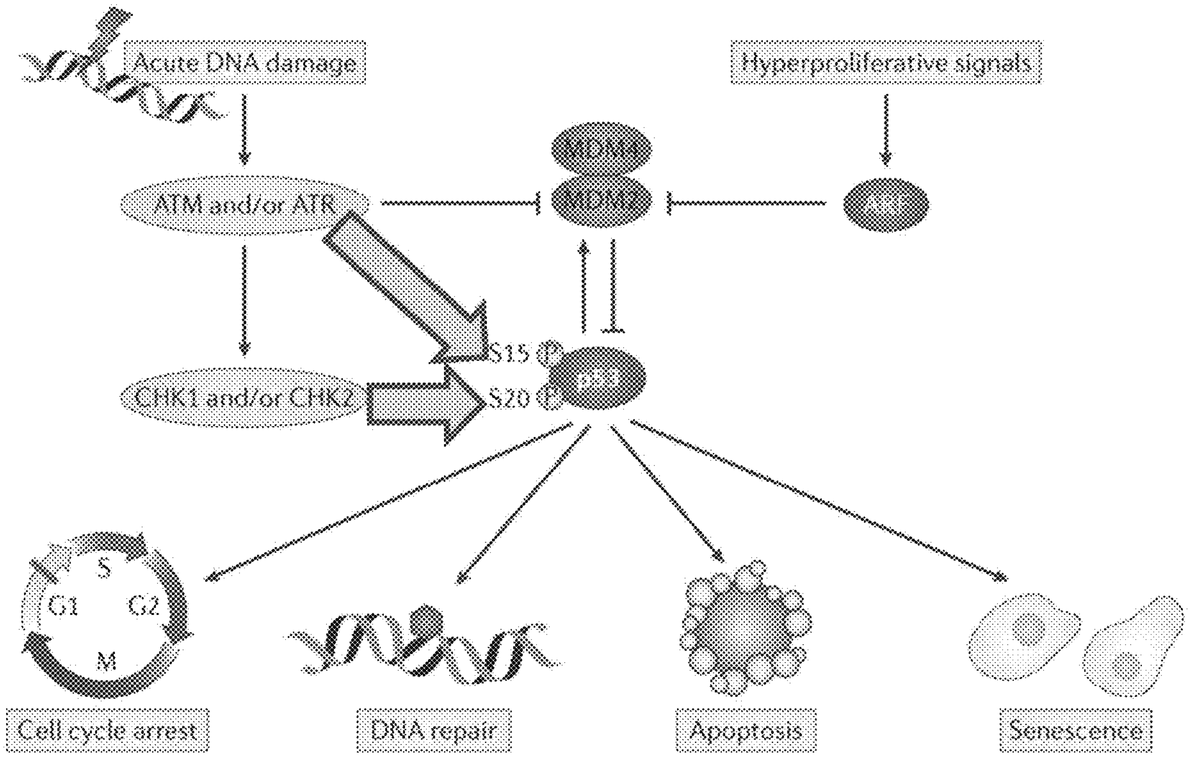
FIG. 31 is a diagram showing the rationale for targeting p53+ tumors with expression constructs comprising a p53 promoter in operable combination with a pro-apoptotic protein, such as a caspase protein, e.g., a Caspase 9 protein. Cancer cells often mutate or delete it so they can grow uncontrollably. However, even when the p53 gene is mutated, the transcription factors that bind to it are almost always still active.

Exemplary pVAX1™ plasmid expression constructs include pVAX-16s-iCasp9-MX (FIG. 16; SEQ ID NO; 6) for the target cell-specific expression of an inducible Caspase 9 protein (iCasp9) under the regulatory control of a p16s promoter, pVAX1-53-iCasp9-MX (FIG. 26; SEQ ID NO: 7) for the target cell-specific expression of an inducible Caspase 9 protein (iCasp9) under the regulatory control of a p53 promoter, pVax1-p53-saCasp9-5 (FIG. 27; SEQ ID NO: 8) for the target cell-specific expression of a self-activating Caspase 9 protein (saCASP9) under under the regulatory control of a p53 promoter, pVax1-p53-iCasp9-OVA (FIG. 28; SEQ ID NO: 11) for the target cell-specific expression of an inducible Caspase 9 protein (iCasp9) and an ovalbumin protein under the regulatory control of a p53 promoter, pVax1-p53-iCasp9-G-O (FIG. 29; SEQ ID NO: 9) for the target cell-specific expression of an inducible Caspase 9 protein (iCasp9) and an ovalbumin protein under the regulatory control of a p53 promoter, pVax1-p53-iCasp9-huCD40L (FIG. 30; SEQ ID NO: 10) for the target cell-specific expression of an inducible Caspase 9 protein (iCasp9) and a CD40 ligand protein (CD40L) under the regulatory control of a p53 promoter.

Within other aspects of the present disclosure, expression constructs are NTC-based plasmid expression constructs, including NTC8385, NTC8685, and NTC9385 plasmid expression constructs, comprising a polynucleotide encoding a pro-apoptotic protein under the regulatory control of a target cell-specific promoter, such as a senescent cell-specific promoter or a cancer cell-specific promoter.

Within further aspects of the present disclosure, expression constructs are gWiz-based plasmid expression constructs comprising a polynucleotide encoding a pro-apoptotic protein under the regulatory control of a target cell-specific promoter, such as a senescent cell-specific promoter or a cancer cell-specific promoter.

The practice of the present disclosure will employ, unless indicated specifically to the contrary, conventional methodology and techniques that are in common use in the fields of virology, oncology, immunology, microbiology, molecular biology, and recombinant DNA, which methodology and techniques are well known by and readily available to those having skill of the art. Such methodology and techniques are explained fully in laboratory manuals as well as the scientific and patent literature. See, e.g., Sambrook, et al., “Molecular Cloning: A Laboratory Manual” (2nd Edition, Cold Spring Harbor Laboratory Press, Cold Spring Harbor, N.Y., 1989); Maniatis et al., “Molecular Cloning: A Laboratory Manual” (1982); “DNA Cloning: A Practical Approach, vol. I & II” (Glover, ed.); “Oligonucleotide Synthesis” (Gait, ed., 1984); Ausubel et al. (eds.), “Current Protocols in Molecular Biology” (John Wiley & Sons, 1994); “Nucleic Acid Hybridization” (Hames & Higgins, eds., 1985); “Transcription and Translation” (Hames & Higgins, eds., 1984); “Animal Cell Culture” (Freshney, ed., 1986); and Perbal, “A Practical Guide to Molecular Cloning” (1984). All publications, patents and patent applications cited herein, whether supra or infra, are hereby incorporated by reference in their entirety.

Systems and Expression Constructs for Reducing, Preventing, and/or Eliminating the Growth and/or Survival of a Target Cell Within certain embodiments, the present disclosure provides expression constructs and systems comprising a delivery vector and an expression construct for achieving a target cell specific reduction, prevention, and/or elimination in the growth and/or survival of the target cell.

Systems

Systems of the present disclosure comprise (1) a vector that is capable of non-specific delivery of a nucleic acid to a cell, whether that cell is a target cell or a non-target cell, and (b) an expression construct comprising a target cell specific transcriptional promoter and a nucleic acid that encodes a therapeutic protein, which expression constructs achieve the target cell specific production of a therapeutic protein. The systems disclosed herein will find utility in abroad range of therapeutic applications in which it is desirable to effectuate the growth or survival characteristics of a target cell, such as a cell that is associated with aging, disease, or another condition, but, at the same time, to not effectuate the growth or survival characteristics of a normal, a non-target cell that is not associated with aging, disease, or another condition.

The present disclosure provides systems for effectuating the growth and/or survival of a broad range of cells that are associated with aging, disease, or other conditions that similarly comprises (1) a non-specific nucleic acid delivery vector and (2) an expression construct comprising (a) a target cell specific transcriptional promoter and (b) a nucleic acid that encodes a therapeutic protein. Each of these aspects of the presently disclosed systems are described in further detail herein.

Within certain embodiments, provided herein are systems for effectuating the growth and/or survival of target cells, which systems comprise: (1) a non-specific nucleic acid delivery vector and (2) an expression construct comprising: (a) a transcriptional promoter, which transcriptional promoter is activated in target cells but not in normal, non-target cells, and (b) a nucleic acid that is under the control of the transcriptional promoter, which nucleic acid encodes a therapeutic protein that can reduce, prevent, and/or eliminate the growth and/or survival of a target cell, for example by inducing a mechanism of programmed cell death in a cell in which it is produced. Thus, these systems achieve the selective killing of target cells by exploiting transcriptional machinery that is produced in, and intrinsic to, target cells, without the use of toxins and in the absence of target cell specific delivery of the expression construct.

In certain aspects of these embodiments wherein the human target cell is a senescent cell, the transcriptional promoter can include at least a transcription factor binding site (i.e., a response element) of p16INK4a/CDKN2A as described in Wang et al., *J. Biol. Chem.* 276(52):48655-61 (2001), which transcriptional promoter is responsive to activation by a factor such as SP1, ETS1, and ETS2. The transcriptional promoter can also include at least a transcription factor binding site (i.e., a response element) of p21/CDKN1A, which transcriptional promoter is responsive to activation by a factor such as p53/TP53. Transcriptional activation induces the expression of a nucleic acid that encodes a therapeutic protein such as CASP3, CASP8, CASP9, DFF40, BAX, HSV-TK, or carbonic anhydrase or an inducible variant of CASP3, CASP8, CASP9, BAX, DFF40, HSV-TK, or cytosine deaminase.

In other aspects of these embodiments wherein the human target cell is a cancer cell, such as a brain cancer cell, a prostate cancer cell, a lung cancer cell, a colorectal cancer cell, a breast cancer cell, a liver cancer cell, a hematologic cancer cell, and a bone cancer cell, the transcriptional promoter can include at least a transcription factor binding site (i.e., a response element) of the $p21^{cip1/waf1}$ promoter, the $p27^{kip1}$ promoter, the $p57^{kip2}$ promoter, the TdT promoter, the Rag-1 promoter, the B29 promoter, the Blk promoter, the CD19 promoter, the BLNK promoter, and/or the λ5 promoter, which transcriptional promoter is responsive to activation by one or more transcription factors such as an EBF3, O/E-1, Pax-5, E2A, p53, VP16, MLL, HSF1, NF-IL6, NFAT1, AP-1, AP-2, HOX, E2F3, and/or NF-κB transcription factor, and which transcriptional activation induces the expression of a nucleic acid that encodes a therapeutic protein such as, for example, CASP3, CASP8, CASP9, BAX, DFF40, HSV-TK, or cytosine deaminase or an inducible variant of CASP3, CASP8, CASP9, BAX, DFF40, HSV-TK, or cytosine deaminase which therapeutic protein reduces, prevents, and/or eliminates the growth and/or survival of the cancer cell, such as, for example, by inducing cell death in the senescent cell via a cellular process including apoptosis. Other therapeutic proteins may be employed that reduce, prevent, and/or eliminate the growth and/or survival of a cancer cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs. In still further aspects of these embodiments wherein the target cell is a human cell that is infected with an infectious agent such as a virus, including, for example, a herpes virus, a polio virus, a hepatitis virus, a retrovirus, an influenza virus, and a rhino virus, or the target cell is a bacterial cell, the transcriptional promoter can be activated by a factor that is expressed by the infectious agent or bacterial cell, which transcriptional activation induces the expression of a nucleic acid that encodes a therapeutic protein such as, for example, CASP3, CASP8, CASP9, BAX, DFF40, HSV-TK, or cytosine deaminase or an inducible variant of CASP3, CASP8, CASP9, BAX, DFF40, HSV-TK, or cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

Each of these aspects of the presently disclosed systems are described in further detail herein.

1. Non-specific Nucleic Acid Delivery Vectors

The systems of the present disclosure achieve target cell specificity by exploiting transcriptional machinery that is unique to a target cell. Thus, the systems described herein employ nucleic acid delivery vectors that can be readily adapted for the non-specific delivery of expression constructs to a cell, including but not limited to a target cell.

A wide variety of both non-viral and viral nucleic acid delivery vectors are well known and readily available in the art and may be adapted for use for the non-specific cellular delivery of the expression constructs disclosed herein. See, for example, Elsabahy et al., *Current Drug Delivery* 8(3): 235-244 (2011) for a general description of viral and non-viral nucleic acid delivery methodologies. The successful delivery of a nucleic acid into mammalian cells relies on the use of efficient delivery vectors. Viral vectors exhibit desirable levels of delivery efficiency, but often also exhibit undesirable immunogenicity, inflammatory reactions, and problems associated with scale-up, all of which can limit their clinical use. The ideal vectors for the delivery of a nucleic acid are safe, yet ensure nucleic acid stability and the efficient transfer of the nucleic acid to the appropriate cellular compartments.

Non-limiting examples of non-viral and viral nuclic acid delivery vectors are described herein and disclosed in scientific and patent literature. More specifically, the presently disclosed systems may employ one or more liposomal vectors, viral vectors, nanoparticles, polyplexesm dendrimers, each of which has been developed for the non-specific delivery of nucleic acids, can be adapted for the non-specific delivery of the expression constructs described herein, and can be modified to incorporate one or more agents for promoting the targeted delivery of a system to a target cell of interest thereby enhancing the target cell specificity of the presently disclosed systems.

2. Liposomal Vectors and Nanoparticles

An expression cassette may be incorporated within and/or associated with a lipid membrane, a lipid bi-layer, and/or a lipid complex such as, for example, a liposome, a vesicle, a micelle and/or a microsphere. Suitable methodology for preparing lipid-based delivery systems that may be employed with the expression constructs of the present disclosure are described in Metselaar et al., *Mini Rev. Med. Chem.* 2(4):319-29 (2002); O'Hagen et al. *Expert Rev. Vaccines* 2(2):269-83 (2003); O'Hagan, *Curr. Drug Targets Infect. Disord.* 1(3):273-86 (2001); Zho et al., *Biosci Rep.* 22(2):355-69 (2002); Chikh et al., *Biosci Rep.* 22(2):339-53 (2002); Bungener et al., *Biosci. Rep.* 22(2):323-38 (2002); Park, *Biosci Rep.* 22(2):267-81 (2002); Ulrich, *Biosci. Rep.* 22(2):129-50; Lofthouse, *Adv. Drug Deliv. Rev.* 54(6):863-70 (2002); Zhou et al., *J. Immunother.* 25(4):289-303 (2002); Singh et al., *Pharm Res.* 19(6):715-28 (2002); Wong et al., *Curr. Med. Chem.* 8(9):1123-36 (2001); and Zhou et al., *Immunomethods* 4(3):229-35 (1994). Midoux et al., *British J. Pharmacol* 157:166-178 (2009) describe chemical vectors for the delivery of nucleic acids including polymers, peptides and lipids. Sioud and Sorensen, *Biochem Biophys Res Commun* 312(4):1220-5 (2003) describe cationic liposomes for the delivery of nucleic acids.

Due to their positive charge, cationic lipids have been employed for condensing negatively charged DNA molecules and to facilitate the encapsulation of DNA into liposomes. Cationic lipids also provide a high degree of stability to liposomes. Cationic liposomes interact with a cell membrane and are taken up by a cell through the process of endocytosis. Endosomes formed as the results of endocytosis, are broken down in the cytoplasm thereby releasing the cargo nucleic acid. Because of the inherent stability of cationic liposomes, however, transfection efficiencies can be low as a result of lysosomal degradation of the cargo nucleic acid.

Helper lipids (such as the electroneutral lipid DOPE and L-a-dioleoyl phosphatidyl choline (DOPC)) can be employed in combination with cationic lipids to form liposomes having decreased stability and, therefore, that exhibit improved transfection efficiencies. These electroneutral lipids are referred to as Fusogenix lipids. See, Gruner et al., *Biochemistry* 27(8):2853-66 (1988) and Farhood et al., *Biochim Biophys Acta* 1235(2):289-95 (1995). DOPE forms an HII phase structure that induces supramolecular arrangements leading to the fusion of a lipid bilayer at a temperature greater than 5° C. to 10° C. The incorporation of DOPE into liposomes also helps the formation of HII phases that destabilize endosomal membranes.

Cholesterol can be employed in combination with DOPE liposomes for applications in which a liposomal vector is administered intravenously. Sakurai et al., *Eur J Pharm Biopharm* 52(2):165-72 (2001). The presence of one unsaturation in the acyl chain of DOPE is a crucial factor for membrane fusion activity. Talbot et al., *Biochemistry* 36(19):5827-36 (1997).

Fluorinated helper lipids having saturated chains, such as DF4C11PE (rac-2,3-Di[11-(F-butyl)undecanoyl) glycero-1-phosphoethanolamine) also enhance the transfection efficiency of lipopolyamine liposomes. Boussif et al., *J Gene Med* 3(2):109-14 (2001); Gaucheron et al., *Bioconj Chem* 12(6):949-63 (2001); and Gaucheron et al., *J Gene Med* 3(4):338-44 (2001).

The helper lipid 1,2-dioleoyl-3-trimethylammonium-propane (DOTAP) enhances efficient of in vitro cell transfection as compared to DOPE lipoplexes. Prata et al., *Chem Commun* 13:1566-8 (2008). Replacement of the double bond of the oleic chains of DOPE with a triple bond as in Distear-4-ynoyl L-a-phosphatidylethanolamine [DS(9-yne)PE] has also been shown to produce more stable lipoplexes. Fletcher et al., *Org Biomol Chem* 4(2):196-9 (2006).

Amphiphilic anionic peptides that are derived from the N-terminal segment of the HA-2 subunit of influenza virus haemagglutinin, such as the IFN7 (GLFEAIEGFIE NGWEGMIDGW YG) and E5CA (GLFEAI-AEFIEGGWEGLEG CA) peptides, can be used to increase the transfection efficiency of liposomes by several orders of magnitude. Wagner et al., *Proc Natl Acad Sci U.S.A.* 89(17):7934-8 (1992); Midoux et al., *Nucl Acids Res.* 21(4):871-8 (1993); Kichler et al., Bioconjug Chem 8(2):213-21 (1997); Wagner, Adv Drug Deliv Rev 38(3):279-289 (1999); Zhang et al., *J Gene Med* 3(6):560-8 (2001). Some artificial peptides such as GALA have been also used as fusogenic peptides. See, for example, Li et al., *Adv Drug Deliv Rev* 56(7):967-85 (2004) and Sasaki et al., *Anal Bioanal Chem* 391(8)2717-27 (2008). The fusogenic peptide of the glycoprotein H from herpes simplex virus improves the endosomal release of DNA/Lipofectamine lipoplexes and transgene expression in human cell (Tu and Kim, *J Gene Med* 10(6):646-54 (2008).

PCT Patent Publication Nos. WO 1999024582A1 and WO 2002/044206 describe a class of proteins derived from the family Reoviridae that promote membrane fusion. These proteins are exemplified by the p14 protein from reptilian reovirus and the p16 protein from aquareovirus. PCT Patent Publication No. WO 2012/040825 describes recombinant polypeptides for facilitating membrane fusion, which polypeptides have at least 80% sequence identity with the ectodomain of p14 fusion-associated small transmembrane (FAST) protein and having a functional myristoylation motif, a transmembrane domain from a FAST protein and a sequence with at least 80% sequence identity with the endodomain of p15 FAST protein. The '825 PCT further describes the addition of a targeting ligand to the recombinant polypeptide for selective fusion. The recombinant polypeptides presented in the '825 PCT can be incorporated within the membrane of a liposome to facilitate the delivery of nucleic acids. Fusogenix liposomes for delivering therapeutic compounds, including nucleic acids, to the cytoplasm of a mammalian cell, which reduce liposome disruption and consequent systemic dispersion of the cargo nucleic acid and/or uptake into endosomes and resulting nucleic acid destruction are available commercially from Innovascreen Inc. (Halifax, Nova Scotia, CA).

A wide variety of inorganic nanoparticles, including gold, silica, iron oxide, titanium, hydrogels, and calcium phosphates have been described for the delivery of nucleic acids and can be adapted for the delivery of the expression constructs described herein. See, for example Wagner and Bhaduri, *Tissue Engineering* 18(1):1-14 (2012) (describing inorganic nanoparticles for delivery of nucleic acid sequences); Ding et al., *Mol Ther* e-pub (2014) (describing gold nanoparticles for nucleic acid delivery); Zhang et al., *Langmuir* 30(3):839-45 (2014) (describing titanium dioxide nanoparticles for delivery of DNA oligonucleotides); Xie et al., *Curr Pharm Biotechnol* 14(10):918-25 (2014) (describing biodegradable calcium phosphate nanoparticles fro gene delivery); Sizovs et al., *J Am Chem Soc* 136(1):234-40 (2014) (describing sub-30 monodisperse oligonucleotide nanoparticles).

Among the advantages of inorganic vectors are their storage stability, low immunogenicity, and resistance to microbial attack. Nanoparticles of less than 100 nm can efficiently trap nucleic acids and allows its escape from endosomes without degradation. Inorganic nanoparticles exhibit improved in vitro transfection for attached cell lines due to their high density and preferential location on the base of the culture dish. Quantum dots have been described that permit the coupling of nucleic acid delivery with stable fluorescence markers.

Hydrogel nanoparticles of defined dimensions and compositions, can be prepared via a particle molding process referred to as PRINT (Particle Replication in Non-wetting Templates), and can be used as delivery vectors for the expression constructs disclosed herein. Nucleic acids can be encapsulated in particles through electrostatic association and physical entrapment. To prevent the disassociation of cargo nucleic acids from nanoparticles following systemic administration, a polymerizable conjugate with a degradable, disulfide linkage can be employed.

The PRINT technique permits the generation of engineered nanoparticles having precisely controlled properties including size, shape, modulus, chemical composition and surface functionality for enhancing the targeting of the expression cassette to a target cell. See, e.g., Wang et al., *J Am Chem Soc* 132:11306-11313 (2010); Enlow et al., *Nano Lett* 11; 808-813 (2011); Gratton et al., Proc Natl Acad Sci USA 105:11613-11618 (2008); Kelly, J Am Chem Soc 130:5438-5439(2008); Merkel et al. Proc Natl Acad Sci USA 108:586-591 (2011). PRINT is also amenable to continuous roll-to-roll fabrication techniques that permit the scale-up of particle fabrication under good manufacturing practice (GMP) conditions.

Nanoparticles can be encapsulated with a lipid coating to improve oral bioavailability, minimize enzymatic degradation and cross blood brain barrier. The nanoparticle surface can also be PEGylated to improve water solubility, circulation in vivo, and stealth properties.

3. Viral Vectors

A wide variety of viral vectors are well known by and readily available to those of skill in the art, including, for example, herpes simplex viral vectors lentiviral vectors, adenoviral vectors, and adeno-associated viral vectors, which viral vectors can be adapted for use in the systems disclosed herein for the delivery of nucleic acids, in particular nucleic acids comprising an expression cassette for the target cell specific expression of a therapeutic protein.

The tropisms of natural or engineered viruses towards specific receptors are the foundations for constructing viral vectors for delivery of nucleic acids. The attachment of these vectors to a target cell is contingent upon the recognition of specific receptors on a cell surface by a ligand on the viral vector. Viruses presenting very specific ligands on their surfaces anchor onto the specific receptors on a cell. Viruses can be engineered to display ligands for receptors presented on the surface of a target cell of interest. The interactions between cell receptors and viral ligands are modulated in vivo by toll like receptors.

The entry of a viral vector into a cell, whether via receptor mediated endocytosis or membrane fusion, requires a specific set of domains that permit the escape of the viral vector from endosomal and/or lysosomal pathways. Other domains facilitate entry into nuclei. Replication, assembly, and latency determine the dynamics of interactions between the vector and the cell and are important considerations in the choice of a viral vector, as well as in engineering therapeutic cargo carrying cells, in designing cancer suicide gene therapies.

Herpes simplex virus (HSV) belongs to a family of herpesviridae, which are enveloped DNA viruses. HSV binds to cell receptors through orthologs of their three main ligand glycoproteins: gB, gH, and gL, and sometimes employ accessory proteins. These ligands play decisive roles in the primary routes of virus entry into oral, ocular, and genital forms of the disease. HSV possesses high tropism towards cell receptors of the nervous system, which can be utilized for engineering recombinant viruses for the delivery of expression cassettes to target cells, including senescent cells, cancer cells, and cells infected with an infectious agent. Therapeutic bystander effects are enhanced by inclusion of connexin coding sequences into the constructs. Herpes Simplex Virus vectors for the delivery of nucleic acids to target cells have been reviewed in Anesti and Coffin, *Expert Opin Biol Ther* 10(1):89-103 (2010); Marconi et al., Adv Exp Med Biol 655:118-44 (2009); and Kasai and Saeki, *Curr Gene Ther* 6(3):303-14 (2006).

Lentivirus belongs to a family of retroviridae, which are enveloped, single stranded RNA retroviruses and include the Human immunodeficiency virus (HIV). HIV envelope protein binds CD4, which is present on the cells of the human immune system such as CD4+ T cells, macrophages, and dendritic cells. Upon entry into a cell, the viral RNA genome is reverse transcribed into double-stranded DNA, which is imported into the cell nucleus and integrated into the cellular DNA. HIV vectors have been used to deliver the therapeutic genes to leukemia cells. Recombinant lentiviruses have been described for mucin-mediated delivery of nucleic acids into pancreatic cancer cells, to epithelial ovarian carcinoma cells, and to glioma cells, without substantial non-specific delivery to normal cells. Lentiviral vectors for the delivery of nucleic acids to target cells have been reviewed in Primo et al., *Exp Dermatol* 21(3):162-70 (2012); Staunstrup and Mikkelsen, *Curr Gene Ther* 11(5):350-62 (2011); and Dreyer, *Mol Biotechnol* 47(2):169-87 (2011).

Adenovirus is a non-enveloped virus consisting of a double-stranded, linear DNA genome and a capsid. Naturally, adenovirus resides in adenoids and may be a cause of upper respiratory tract infections. Adenovirus utilizes a cell's coxsackie virus and adenovirus receptor (CAR) for the adenoviral fiber protein for entry into nasal, tracheal, and pulmonary epithelia. CARs are expressed at low levels on senescent and cancer cells. Recombinant adenovirus can be generated that are capable of nucleic acid deliver to target cells. Replication-competent adenovirus-mediated suicide gene therapy (ReCAP) is in the clinical trials for newly-diagnosed prostate cancer. Adenoviral vectors for the delivery of nucleic acids to target cells have been reviewed in Huang and Kamihira, *Biotechnol Adv.* 31(2):208-23 (2013); Alemany, *Adv Cancer Res* 115:93-114 (2012); Kaufmann and Nettelbeck, *Trends Mol Med* 18(7):365-76(2012); and Mowa et al., *Expert Opin Drug Deliv* 7(12):1373-85 (2010).

Adeno-associated virus (AAV) is a small virus that infects humans and some other primate species. AAV is not currently known to cause disease and consequently the virus causes a very mild immune response. Vectors using AAV can infect both dividing and quiescent cells and persist in an extrachromosomal state without integrating into the genome of the host cell. These features make AAV a very attractive candidate for creating viral vectors for use in the systems of the present disclosure. Adeno-associated virus (AAV) vectors for the delivery of nucleic acids to target cells have been reviewed in Li et al., *J. Control Release* 172(2):589-600

(2013); Hajitou, *Adv Genet* 69:65-82 (2010); McCarty, *Mol Ther* 16(10):1648-56 (2008); and Grimm et al., *Methods Enzymol* 392:381-405 (2005).

4. Polyplexes

Polyplexes are complexes of polymers with DNA. Polyplexes consist of cationic polymers and their fabrication is based on self-assembly by ionic interactions. One important difference between the methods of action of polyplexes and liposomes and lipoplexes is that polyplexes cannot directly release their nucleic acid cargo into the cytoplasm of a target cell. As a result co-transfection with endosome-lytic agents such as inactivated adenovirus is required to facilitate escape from the endocytic vesicle made during particle uptake, better understanding of the mechanisms by which DNA can escape from endolysosomal pathway (i.e., the proton sponge effect) has triggered new polymer synthesis strategies such as the incorporation of protonable residues in polymer backbone and has revitalized research on poly cation-based systems. See, e.g., Parhamifar et al., *Methods* e-pub (2014); Rychgak and Kilbanov, *Adv Drug Deliv Rev* e-pub (2014); Jafari et al., *Curr Med Chem* 19(2):197-208 (2012).

Due to their low toxicity, high loading capacity, and ease of fabrication, polycationic nanocarriers exhibit substantial advantages over viral vectors, which show high immunogenicity and potential carcinogenicity and lipid-based vectors which cause dose dependent toxicity. Polyethyleneimine, chitosan, poly(beta-amino esters), and polyphosphoramidate have been described for the delivery of nucleic acids. See, e.g., Buschmann et al., *Adv Drug Deliv Rev* 65(9):1234-70 (2013). The size, shape, and surface chemistry of these polymeric nano-carriers can be easily manipulated.

5. Dendrimers

Dendrimers are highly branched macromolecules having a spherical shape. The surface of dendrimer particles may be functionalized such as, for example, with positive surface charges (cationic dendrimers), which may be employed for the delivery of nucleic acids. Dendrimer-nucleic acid complexes are taken into a cell via endocytosis. Dendrimers offer robust covalent construction and extreme control over molecule structure and size. Dendrimers are available commercially from Dendritic Nanotechnologies Inc. (Priostar; Mt Pleasant, Mich.), who produce dendrimers using kinetically driven chemistry, which can be adapted fro the delivery of nucleic acids and can transfect cells at a high efficiency with low toxicity.

It will be understood that, while targeted delivery of an expression construct is not required by the systems of the present disclosure and that the targeted reduction, prevention, and/or elimination in the growth and/or survival of a target cell may be achieved by exploiting the intracellular transcriptional machinery of a target cell that is unique to the target cell, it may be desirable, depending upon the precise application contemplated, the incorporate into an otherwise non-specific delivery vector one or more components that facilitate the targeted delivery to a subset of cells at least some of which include a target cell that is susceptible to the growth and/or survival inhibition by the expression constructs of the present disclosure.

The targeted delivery of nucleic acids by liposome, nanoparticle, viral and other vectors described herein has been described in the scientific and patent literature and is well known by and readily available to those of skill in the art. Such targeted delivery technologies may, therefore, be suitably adapted for targeting the delivery of expression constructs of the present disclosure to enhance the specificity of the growth and/or survival reduction, prevention, and/or elimination that is achieved within a target cell. The following examples of targeted delivery technologies are provided herein to exemplify, not to limit, the targeted delivery vectors that may be adapted to achieve the systems of the present disclosure.

Expression Constructs

Expression constructs of the present disclosure comprise: (a) a transcriptional promoter that is responsive to a factor or factors that are produced in a target cell, one or more of which factors is not produced, is produced at a substantially reduced level, is inactive, and/or exhibits a substantially reduced activity in a non-target cell; and (b) a nucleic acid that is operably linked to and under the regulatory control of the transcriptional promoter, wherein the nucleic acid encodes a protein that is capable of reducing, preventing, and/or eliminating the growth and/or survival of a cell in which it is produced, including a target cell.

1. Target Cell Specific Transcriptional Promoters

The present disclosure provides systems comprising a vector for delivering a nucleic acid to a cell wherein the nucleic acid is under the transcriptional control of a promoter that is derepressed or activated in a target cell, but is reprepressed or inactivated in a normal cell, non-target cell.

It will be understood the specificity of the presently disclosed systems toward a target cell is achieved, therefore, through the target cell-specific transcriptional activation of a nucleic acid that encodes a protein that reduces, prevents, and/or eliminates the growth and/or survival of a cell without regard to whether that cell is a target cell. Thus, the target cell specificity of the presently-disclosed systems derives from the transcriptional promoter that regulates the expression of the nucleic acid within the expression cassette in conjunction with transcription-regulatory machinery that is provided by, and unique to, the target cell.

Thus, transcriptional promoters that may be suitably employed in the expression constructs, systems, and methods of the present disclosure include those transcriptional promoters that are capable of promoting the expression of a nucleic acid in a target cell (i.e., a cell that is associated with aging, disease, or other condition), but incapable of, or exhibit a substantially reduced capability of, promoting expression of that nucleic acid in a non-target cell.

Exemplified herein are expression constructs and systems comprising expression constructs wherein the transcriptional promoter is activated in a target cell that is associated with aging, disease, or another condition.

In some embodiments, the present disclosure provides expression constructs and systems that may be employed in methods for the treatment of aging reducing, preventing, and/or eliminating the growth and/or survival of a cell, such as a senescent cell, which is associated with aging. In certain aspects of those embodiments, expression constructs employ a transcriptional promoter that is responsive to one or more factors that are produced within a target cell, such as a senescent cell, but are not produced in a non-target cell wherein those one or more factors derepress and/or activate the transcriptional promoter and, as a consequence, promote the expression of a nucleic acid encoding a therapeutic protein that reduces, prevents, and/or eliminates the growth and/or survival of a cell that is associated with aging, including a senescent cell.

The transcriptional promoter itself is the primary mechanism by which senescent cells are preferentially targeted by the systems described in this disclosure. A prototypic example of a target specific transcriptional promoter for use with the systems in this disclosure is a promoter that is only active or mostly active in senescent cells. A number of promoters known by artisans to be active in senescent cells may be used with this system.

In certain aspects of these embodiments wherein the human target cell is a senescent cell, the transcriptional promoter can include the promoter region of p16INK4a/CDKN2A as described in Wang et al., *J. Biol. Chem.* 276(52)48655-61 (2001), which transcriptional promoter is responsive to activation by a factor such as SP1, ETS1, and ETS2. The transcriptional promoter can also include the promoter region of p21/CDKN1A, which transcriptional promoter is responsive to activation by a factor such as p53/TP53.

In other aspects of these embodiments wherein the human target cell is a cancer cell, such as a brain cancer cell, a prostate cancer cell, a lung cancer cell, a colorectal cancer cell, a breast cancer cell, a liver cancer cell, a hematologic cancer cell, and a bone cancer cell, the transcriptional promoter can include the $p21^{cip1/waf1}$ promoter, the $p27^{kip1}$ promoter, the $p57^{kip2}$ promoter, the TdT promoter, the Rag-1 promoter, the B29 promoter, the Blk promoter, the CD19 promoter, the BLNK promoter, and/or the λ5 promoter, which transcriptional promoter is responsive to activation by one or more transcription factors such as an EBF3, O/E-1, Pax-5, E2A, p53, VP16, MLL, HSF1, NF-IL6, NFAT1, AP-1, AP-2, HOX, E2F3, and/or NF-κB transcription factor, and which transcriptional activation induces the expression of a nucleic acid that encodes a therapeutic protein.

In still further aspects of these embodiments wherein the target cell is a human cell that is infected with an infectious agent, such as a virus, including, for example, a herpes virus, a polio virus, a hepatitis virus, a retrovirus virus, an influenza virus, and a rhino virus, or the target cell is a bacterial cell, the transcriptional promoter can be activated by a factor that is expressed by the infectious agent or bacterial cell, which transcriptional activation induces the expression of a nucleic acid that encodes a therapeutic protein.

2. The p16 Transcriptional Promoter

In one embodiment, the suicide gene could be placed under control of a p16 promoter, such as a p16Ink4a gene promoter, which is transcriptionally active in senescent, but not in non-senescent cells.

In humans, p16 is encoded by the CDKN2A gene, which gene is frequently mutated or deleted in a wide variety of tumors. p16 is an inhibitor of cyclin dependent kinases such as CDK4 and CDK6, which phosphorylate retinoblastoma protein (pRB) thereby causing the progression from G1 phase to S phase. p16 plays an important role in cell cycle regulation by decelerating cell progression from G1 phase to S phase, and therefore acts as a tumor suppressor that is implicated in the prevention of cancers, including, for example, melanomas, oropharyngeal squamous cell carcinomas, and esophageal cancers. The designation p16Ink4A refers to the molecular weight (15,845) of the protein encoded by one of the splice variants of the CDKN2A gene and to its role in inhibiting CDK4.

In humans, p16 is encoded by CDKN2A gene, located on chromosome 9 (9p21.3). This gene generates several transcript variants that differ in their first exons. At least three alternatively spliced variants encoding distinct proteins have been reported, two of which encode structurally related isoforms known to function as inhibitors of CDK4. The remaining transcript includes an alternate exon 1 located 20 kb upstream of the remainder of the gene; this transcript contains an alternate open reading frame (ARF) that specifies a protein that is structurally unrelated to the products of the other variants. The ARF product functions as a stabilizer of the tumor suppressor protein p53, as it can interact with and sequester MDM2, a protein responsible for the degradation of p53. In spite of their structural and functional differences, the CDK inhibitor isoforms and the ARF product encoded by this gene, through the regulatory roles of CDK4 and p53 in cell cycle G1 progression, share a common functionality in control of the G1 phase of the cell cycle. This gene is frequently mutated or deleted in a wide variety of tumors and is known to be an important tumor suppressor gene.

Concentrations of p16INK4a increase dramatically as tissue ages. Liu et al., *Aging Cell* 8(4):439-48 (2009) and Krishnamurthy et al., *Nature* 443(7110):453-7 (2006). The increased expression of the p16 gene with age reduces the proliferation of stem cells thereby increasing the cellular senescence-associated health risks in a human.

p16 is a cyclin-dependent kinase (CDK) inhibitor that slows down the cell cycle by prohibiting progression from G1 phase to S phase. Normally, CDK4/6 binds cyclin D and forms an active protein complex that phosphorylates retinoblastoma protein (pRB). Once phosphorylated, pRB disassociates from the transcription factor E2F1, liberating E2F1 from its cytoplasm bound state allowing it to enter the nucleus. Once in the nucleus, E2F1 promotes the transcription of target genes that are essential for transition from G1 to S phase.

p16 acts as a tumor suppressor by binding to CDK4/6 and preventing its interaction with cyclin D. This interaction ultimately inhibits the downstream activities of transcription factors, such as E2F1, and arrests cell proliferation. This pathway connects the processes of tumor oncogenesis and senescence, fixing them on opposite ends of a spectrum.

On one end, the hypermethylation, mutation, or deletion of p16 leads to downregulation of the gene and can lead to cancer through the dysregulation of cell cycle progression. Conversely, activation of p16 through the ROS pathway, DNA damage, or senescence leads to the build up of p16 in tissues and is implicated in aging of cells.

Regulation of p16 is complex and involves the interaction of several transcription factors, as well as several proteins involved in epigenetic modification through methylation and repression of the promoter region. PRC1 and PRC2 are two protein complexes that modify the expression of p16 through the interaction of various transcription factors that execute methylation patterns that can repress transcription of p16. These pathways are activated in cellular response to reduce senescence.

3. The p21 Transcriptional Promoter

A nucleic acid encoding a therapeutic protein could be placed under the control of the p21/CDKN1A transcriptional promoter that is often transcriptionally active in senescent, and cancerous or pre-cancerous cells. p53/TP53 plays a central role in the regulation of p21 and, therefore, in the growth arrest of cells when damaged. p21 protein binds directly to cyclin-CDK complexes that drive the cell cycle and inhibits their kinase activity thereby causing cell cycle arrest to allow repair to take place. p21 also mediates growth arrest associated with differentiation and a more permanent growth arrest associated with cellular senescence. The p21 gene contains several p53 response elements that mediate direct binding of the p53 protein, resulting in transcriptional activation of the gene encoding the p21 protein. The role of p53 gene regulation in cellular senescence is described in Kelley et al., *Cancer Research* 70(9):3566-75. (2010).

Nucleic Acids and Therapeutic Proteins Encoded Thereby

Nucleic acids that may be suitably employed in the expression constructs, systems, and methods of the present disclosure encode a protein that is capable of reducing, preventing, and/or eliminating the growth and/or survival of a cell in which it is produced, including a target cell. Thus, the target cell specificity of the presently disclosed expression constructs and systems is achieved by the expression within a target cell, but not within a non-target cell, of a nucleic acid that encodes a therapeutic protein.

Nucleic acids encoding therapeutic proteins that may be employed in the expression constructs and systems of the present disclosure include nucleic acids encoding one or more protein that induces apoptosis in a cell in which it is produced. Exemplified herein are expression constructs and systems comprising one or more "suicide genes," such as a nucleic acid encoding Herpes Simplex Virus Thymidine Kinase (HSV-TK), cytosine deaminase, CASP3, CASP8, CASP9, BAX, DFF40, cytosine deaminase, or other nucleic acid that encodes a protein that is capable of inducing apoptosis is a cell.

Apoptosis, or programmed cell death (PCD), is a common and evolutionary conserved property of all metazoans. In many biological processes, apoptosis is required to eliminate supernumerary or dangerous (such as pre-cancerous) cells and to promote normal development. Dysregulation of apoptosis can, therefore, contribute to the development of many major diseases including cancer, autoimmunity and neurodegenerative disorders. In most cases, proteins of the caspase family execute the genetic programme that leads to cell death.

Apoptosis is triggered in a mammalian cell, in particular in a human cell, through the activation of caspase proteins, in particular the caspase proteins CASP3, CASP8, and CASP9. See, for example, Xie et al., *Cancer Res* 61(18): 186-91 (2001); Carlotti et al., *Cancer Gene Ther* 12(7):627-39 (2005); Lowe et al., *Gene Ther* 8(18):1363-71 (2001); and Shariat et al., *Cancer Res* 61(6):2562-71 (2001).

DNA fragmentation factor (DFF) is a complex of the DNase DFF40 (CAD) and its chaperone/inhibitor DFF45 (ICAD-L). In its inactive form, DFF is a heterodimer composed of a 45 kDa chaperone inhibitor subunit (DFF45 or ICAD), and a 40 kDa latent endonuclease subunit (DFF40 or CAD). Upon caspase-3 cleavage of DFF45, DFF40 forms active endonuclease homo-oligomers. It is activated during apoptosis to induce DNA fragmentation. DNA binding by DFF is mediated by the nuclease subunit, which can also form stable DNA complexes after release from DFF. The nuclease subunit is inhibited in DNA cleavage but not in DNA binding. DFF45 can also be cleaved and inactivated by caspase-7 but not by caspase-6 and caspase-8. The cleaved DFF45 fragments dissociate from DFF40, allowing DFF40 to oligomerise, forming a large complex that cleaves DNA by introducing double strand breaks. Histone H1 confers DNA binding ability to DFF and stimulates the nuclease activity of DFF40. Activation of the apoptotic endonuclease DFF-40 is described in Liu et al., *J Biol Chem* 274(20): 13836-40(1999).

Thymidine kinase (TK) is an ATP-thymidine 5'-phosphotransferase that is present in all living cells as well as in certain viruses including herpes simplex virus (HSV), varicella zoster virus (VZV), and Epstein-Barr virus (EBV). Thymidine kinase converts deoxythymidine into deoxythymidine 5'-monophosphate (TMP), which is phosphorylated to deoxythymidine diphosphate and to deoxythymidine triphosphate by thymidylate kinase and nucleoside diphosphate kinase, respectively. Deoxythymidine triphosphase is incorporated into cellular DNA by DNA polymerases and viral reverse transcriptases.

When incorporated into DNA, certain dNTP analogs, such as synthetic analogues of 2'-deoxy-guanosine (e.g., Ganciclovir), cause the premature termination of DNA synthesis, which triggers cellular apoptosis.

Within certain embodiments, the expression cassettes and systems of the present disclosure employ a nucleic acid that encodes HSV-TK. Following the administration to a human of a system employing a nucleic acid encoding HSV-TK, an analogue of a 2'-deoxy-nucleotide, such as 2'-deoxy-guanosine, is administered to the human. The HSV-TK efficiently converts the 2'-deoxy-nucleotide analogue into a dNTP analogue, which when incorporated into the DNA induces apoptosis in the target cell.

Cytosine deaminase (CD) catalyzes the hydrolytic conversion in DNA of cytosine to uracil and ammonia. If a CD-modified site is recognized by an endonuclease, the phosphodiester bond is cleaved and, in a normal cell, is repaired by incorporating a new cytosine. In the presence of 5-fluorocytosine (5-FC), cytosine deaminase converts 5-FC into 5-fluorouracil (5-FU), which can inhibit target cell growth. Transgenic expression of CD in a target cell, therefore, reduces the growth and/or survival of the target cell.

The present disclosure provides expression constructs and systems that further comprise one or more safety features to ensure that the expression of a nucleic acid encoding a therapeutic protein is upregulated in appropriate cells, over a desired time period, and/or to a specified level.

Within one such embodiments, expression constructs and systems of the present disclosure employ nucleic acids that encode inducible variants of therapeutic proteins, including, for example, inducible variants of CASP3, CASP8, and CASP9, which require the further contacting of a cell with or administration to a human of a chemical or biological compound that activates the therapeutic protein.

Inducible suicide gene systems are well known and readily available in the art and have been described, for example, in Miller et al., PCT Patent Publication No. WO 2008/154644 and Brenner, U.S. Patent Publication No. 2011/0286980. In addition, Shah et al., *Genesis* 45(4):104-199 (2007) describe a double-inducible system for Caspase 3 and 9 that employs RU486 and chemical inducers of dimerization (CID). Straathof et al., *Blood* 105(11):4247-4254 (2005) describe an inducible caspase 9 system in which caspase 9 is fused to a human FK506 binding protein (FKBP) to allow the conditional dimerization using the small molecule AP20187 (ARIAD Pharmaceuticals, Cambridge, Mass.), which is a non-toxic synthetic analog of FK506. Carlotti et al., *Cancer Gene Ther* 12(7):627-39 (2005) describe an inducible caspase 8 system by employing the ARIAD™ homodimerization system (FKC8; ARIAD Pharmaceuticals).

Full-length inducible caspase 9 (FF-C-Casp9.I.GFP) comprises a full-length caspase 9, including its caspase recruitment domain (CARD; GenBank NM001 229) linked to two 12 kDa human FK506 binding proteins (FKBP12; GenBank AH002 818) that contain an F36V mutation as described in Clackson et al., *Proc. Natl. Acad. Sci. U.S.A.* 95:10437-10442 (1998) and are connected by a Ser-Gly-Gly-Gly-Ser linker that connects the FKBPs and caspase 9 to enhance flexibility.

In a further embodiment, the inducible suicide gene could be linked to the nucleic acid sequence for a detectable biomarker such as luciferasc or green fluorescent protein to permit the detection of the targeted cells prior to administering a compound to activate an inducible therapeutic protein.

Compositions and Formulations of Systems Comprising Vectors and Expression Cassettes The present disclosure provides systems comprising a vector and an expression cassette wherein the expression cassette comprises a transcriptional promoter that is responsive to one or more transcription factors that are expressed in a target cell and a nucleic acid encoding a therapeutic protein. Systems can be administered to a human patient by themselves or in pharmaceutical compositions where they are mixed with suitable carriers or excipient(s) at doses to treat or ameliorate a disease or condition as described herein. Mixtures of these systems can also be administered to the patient as a simple mixture or in pharmaceutical compositions.

Compositions within the scope of this disclosure include compositions wherein the therapeutic agent is a system comprising a vector and an expression cassette in an amount effective to reduce or eliminate the growth and/or survival of a target cell such as a senescent cell, a cancer cell, a cell infected with an infectious agent, a bacterial cell, or a cell that is associated with another disease or condition. Determination of optimal ranges of effective amounts of each component is within the skill of the art. The effective dose is a function of a number of factors, including the specific system, the presence of one or more additional therapeutic agent within the composition or given concurrently with the system, the frequency of treatment, and the patient's clinical status, age, health, and weight.

Compositions comprising a system may be administered parenterally. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion. Alternatively, or concurrently, administration may be orally.

Compositions comprising a system may, for example, be administered intravenously via an intravenous push or bolus. Alternatively, compositions comprising a system may be administered via an intravenous infusion.

Compositions include a therapeutically effective amount of a system, and a pharmaceutically acceptable carrier. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the inhibitor, preferably in purified form, together with a suitable amount of carrier so as to provide the form for proper administration to the patient. The formulation should suit the mode of administration.

Compositions can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The systems disclosed herein can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

Methods for Treatment of a Disease or Condition Associated with, and for Reducing, Inhibiting, and/or Preventing the Growth and/or Survival of, a Cell that is Associated with Aging, Cancer, Infectious Disease, Bacterial Infection, and/or Other Disease or Condition The present disclosure provides methods for reducing, inhibiting, and/or preventing the growth and or survival of a cell that is associated with aging, cancer, infectious disease, bacterial infection, and/or other disease or condition, which methods comprise contacting a target cell or a population of cell comprising a target cell with a system as described herein, which system comprises a vector and an expression construct, which expression construct comprises a transcriptional promoter and a nucleic acid.

The present disclosure also provides methods for the treatment of aging, cancer, infectious disease, bacterial infection, and/or other disease or condition in a patient, which methods comprise the administration of a system as described herein, which system comprises a vector and an expression construct, which expression construct comprises a transcriptional promoter and a nucleic acid.

The present therapeutic methods involve contacting a target cell with, or administering to a human patient, a composition comprising one or more system comprising a vector and an expression cassette to a human patient for reducing and/or eliminating the growth and/or survival of a cell that is associated with senescence, cancer, an infectious disease, a bacterial infection or another disease or condition.

The amount of the system that will be effective in the treatment, inhibition, and/or prevention of aging, cancer, infectious disease, bacterial infection, or other disease or condition that is associated with the elevated expression of one or more transcription factors can be determined by standard clinical techniques. In vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

The systems or pharmaceutical compositions of the present disclosure can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a system on a cell line or a patient tissue sample. The effect of the system or pharmaceutical composition thereof on the cell line and/or tissue sample can be determined utilizing techniques known to those of skill in the art including, but not limited to proliferation and apoptosis assays. In accordance with the present disclosure, in vitro assays that can be used to determine whether administration of a specific compound is indicated, include in vitro cell culture assays in which a patient tissue sample is grown in culture, and exposed to or otherwise administered a compound, and the effect of such compound upon the tissue sample is observed.

The present disclosure provides methods for the treatment and growth and/or survival inhibition by administration to a subject of an effective amount of a system or pharmaceutical composition thereof as described herein. In one aspect, the system is substantially purified such that it is substantially free from substances that limit its effect or produce undesired side-effects.

Methods of administration include, but are not limited to, intradermal, intramuscular, intraperitoneal, intravenous, subcutaneous, intranasal, epidural, and oral routes. The systems or compositions thereof may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the inhibitors or compositions into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

It may be desirable to administer the systems or compositions thereof locally to the area in need of treatment; this may be achieved by, for example, local infusion during surgery, topical application, by injection, by means of a catheter, by means of a suppository, or by means of an implant, said implant being of a porous, non-porous, or gelatinous material, including membranes, such as sialastic membranes, or fibers.

The system can be delivered in a controlled release system placed in proximity of the therapeutic target, thus requiring only a fraction of the systemic dose (see, e.g., Goodson, in Medical Applications of Controlled Release 2:115-138 (1984)).

Intravenous infusion of a compositions comprising a system may be continuous for a duration of at least about one day, or at least about three days, or at least about seven days, or at least about 14 days, or at least about 21 days, or at least about 28 days, or at least about 42 days, or at least about 56 days, or at least about 84 days, or at least about 112 days.

Continuous intravenous infusion of a composition comprising a system may be for a specified duration, followed by a rest period of another duration. For example, a continuous infusion duration may be from about 1 day, to about 7 days, to about 14 days, to about 21 days, to about 28 days, to about 42 days, to about 56 days, to about 84 days, or to about 112 days. The continuous infusion may then be followed by a rest period of from about 1 day, to about 2 days to about 3 days, to about 7 days, to about 14 days, or to about 28 days. Continuous infusion may then be repeated, as above, and followed by another rest period.

Regardless of the precise infusion protocol adopted, it will be understood that continuous infusion of a composition comprising a system will continue until either desired efficacy is achieved or an unacceptable level of toxicity becomes evident.

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

All references cited herein, whether supra or infra, including, but not limited to, patents, patent applications, and patent publications, whether U.S., PCT, or non-U.S. foreign, and all technical and/or scientific publications are hereby incorporated by reference in their entirety.

EXAMPLES

While various embodiments have been disclosed herein, other embodiments will be apparent to those skilled in the art. The various embodiments disclosed herein are for purposes of illustration and are not intended to be limiting, with the true scope and spirit being indicated by the claims. The present disclosure is further described with reference to the following examples, which are provided to illustrate certain embodiments and are not intended to limit the scope of the present disclosure or the subject matter claimed.

Example 1 p14 FAST Fusogenic Lipid Nanoparticles (LNP) Enhance Gene Delivery to Tumors

This Example demonstrates that Fusogenix™ (Innovascreen, Halifax, Nova Scotia, Canada) lipid nanoparticles utilizing a p14 FAST fusion from reptilian reovirus are effective at delivering a plasmid DNA construct to a target rumor.

Figure 7A:
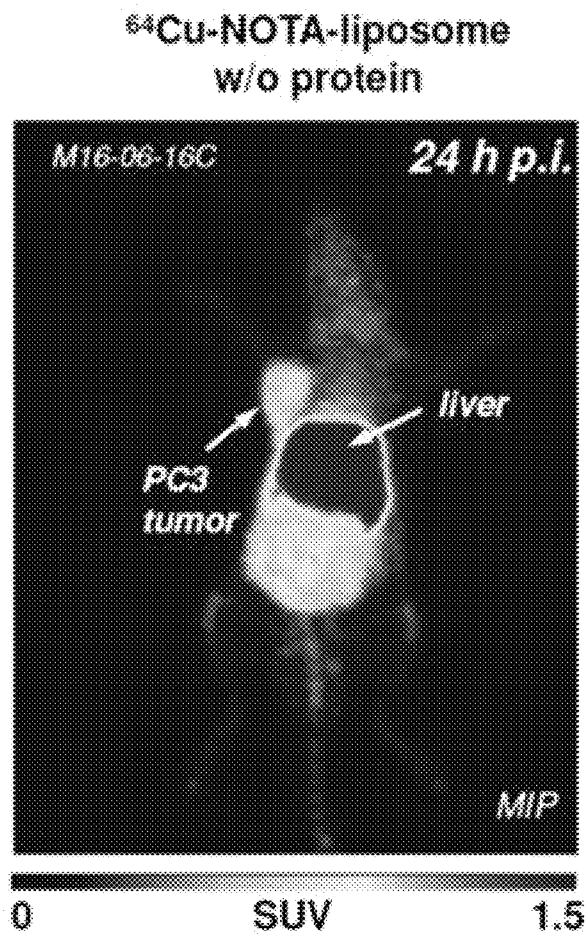
FIG. 7A presents PET data obtained from a mouse to which $^{64}$Cu-NOTA-liposomes without protein were administered.
Figure 7B:
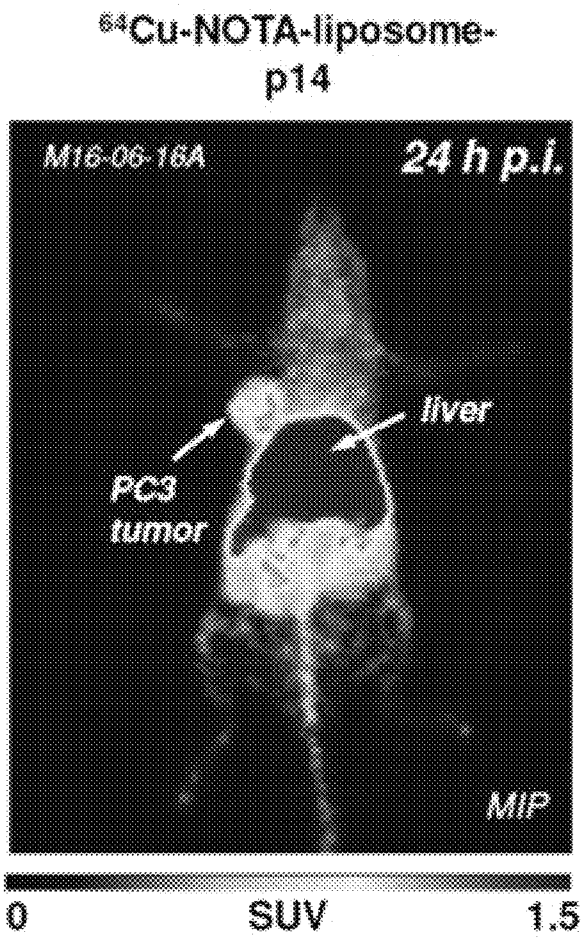
FIG. 7B presents PET data obtained from a mouse to which $^{64}$Cu-NOTA-liposome-p14 were administered.

Fusogenix lipid nanoparticles labeled with $^{64}$Cu ($^{64}$Cu NOTA-liposomes) either with or without a p14 FAST fusion protein (described in PCT Patent Publication Nos. WO2002044206A2 and WO2012040825A1) were administered intravenously to a M16 mouse model system for prostate cancer (PC3 cells). Seo, *Bioconjug Chem* 19(12): 2577-2585 (2009) and Reeves, *Cancer Therapy* 136(7): 1731-1740 (2014). 24 hours post-immunization, PC3 tumors were visualize using positron emission tomography (PET). FIGS. 7A and 7B.

Figure 8:
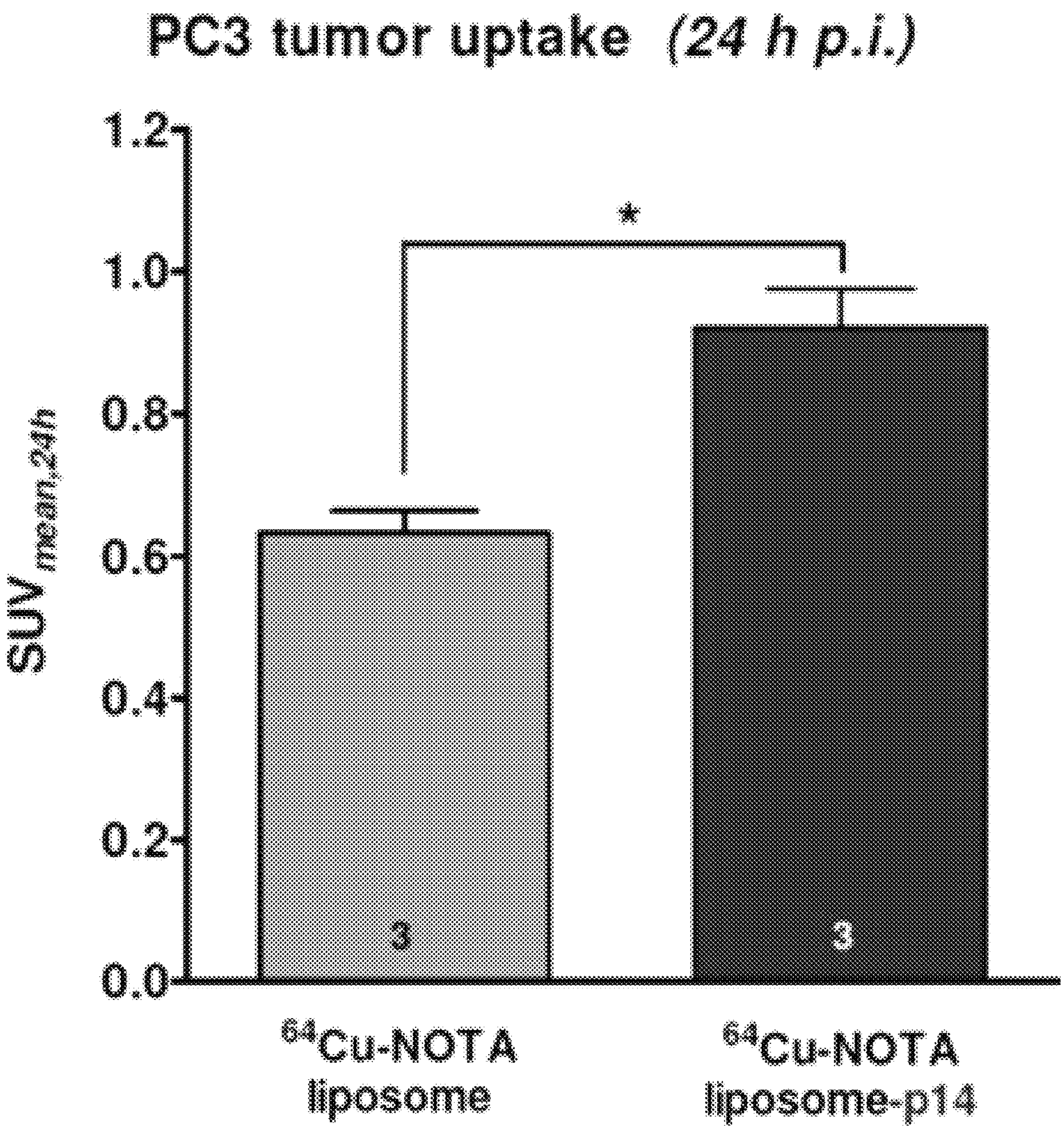
FIG. 8 is a bar graph of data obtained with Fusogenix lipid nanoparticles comparing $SUV_{mean,\ 24h}$ for $^{64}$Cu-NOTA-liposomes without protein and $^{64}$Cu-NOTA-liposome-p14. The data presented in FIGS. 7 and 8 demonstrate a 50% increase in gene/siRNA delivery to prostate tumors as compared to a competing formulation.
Figure 9:
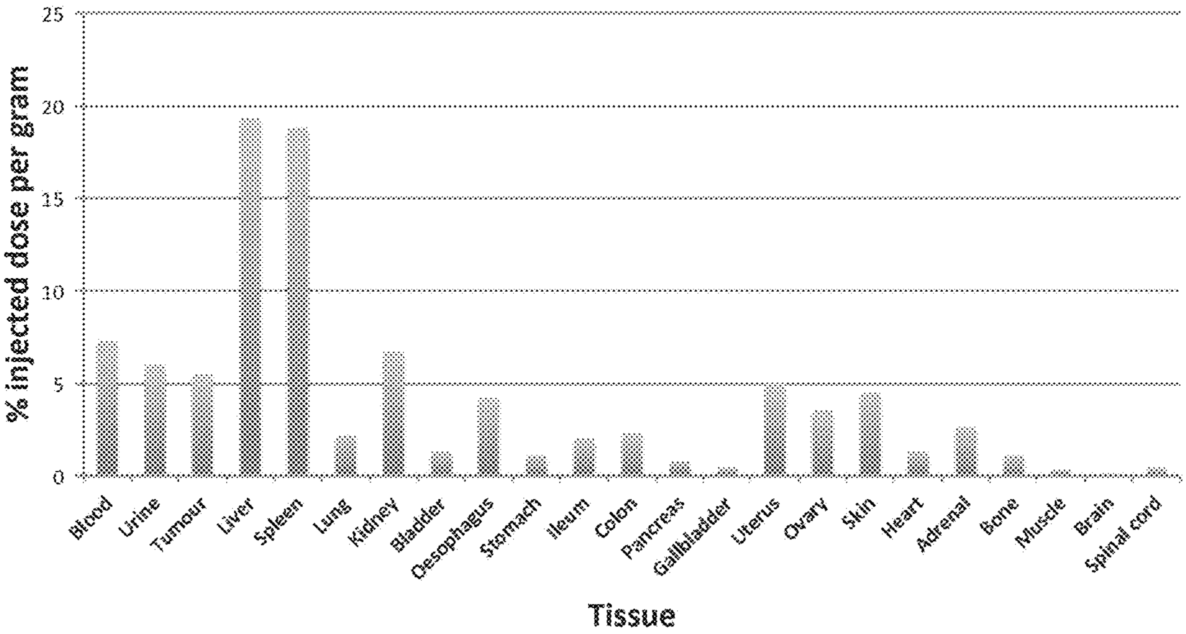
FIG. 9 is a bar graph of the biodistribution of labelled pegylated liposomes in nude mice expressed after 24 hours as discussed in Example 1.

The data presented in FIG. 8 demonstrate a 50% increase in PC3 prostate tumor uptake of $^{64}$Cu NOTA-liposomes with p14 FAST fusion protein as compared to $^{64}$Cu NOTA-liposomes without p14 FAST fusion protein. The biodistribution of labelled pegylated liposomes in nude mice expressed after 24 hours is presented in FIG. 9.

Example 2

In Vivo Administered p14 FAST Fusogenix™ Lipid Nanoparticles are Non-Toxic and Well Tolerated This Example demonstrates that Fusogenix™ (Innovascreen, Halifax, Nova Scotia, Canada) lipid nanoparticles utilizing a p14 FAST fusion from reptilian reovirus do not exhibit adverse side-effects in any of the major mammalian organ systems examined when administered in vivo to Sprague-Dawley rats, are effective at delivering a plasmid DNA construct to a target tumor.

Presented herein are comparative studies that were performed with N=20 male rats treated with either (i) no LNPs (PBS), (ii) LNPs without p14, or (iii) p14 containing Fusogenix lipid nanoparticles (LNPs). Each animal received a total of three injections of 15 mg/kg in their tail, over a 4 day period. Treatment of the animals with p14 containing LNPs did not result in any acute changes in animal behavior and animal growth was not affected by treatment with p14 containing LNPs. Animals treated with p14 containing LNPs had similar organ weights as compared to all other animal groups studied.

Treatment with p14 containing LNPs did not affect the microscopic appearance of tissues from major organ systems. Tissues from the lungs, brain, heart, kidney, liver, reproductive organs, gut, endocrine system, lymph nodes, spleen, pancreas, bladder and tail were all independently examined and p14 did not elicit any visible signs of toxicity. Importantly, the liver appeared to be unaffected by exposure to p14. Moreover, no differences were identified between the tissues of p14 treated animals versus control groups.

A number of blood chemistry values were measured to determine the impact of p14 on physiological function and inflammation. Parameters such as ALT and AST that denote acute liver function were all within normal ranges. Fusogenix LNPs containing p14 do not show any adverse side-effects in any of the major mammalian organ systems examined. Histological appearance of tissues was also normal.

Figure 10:
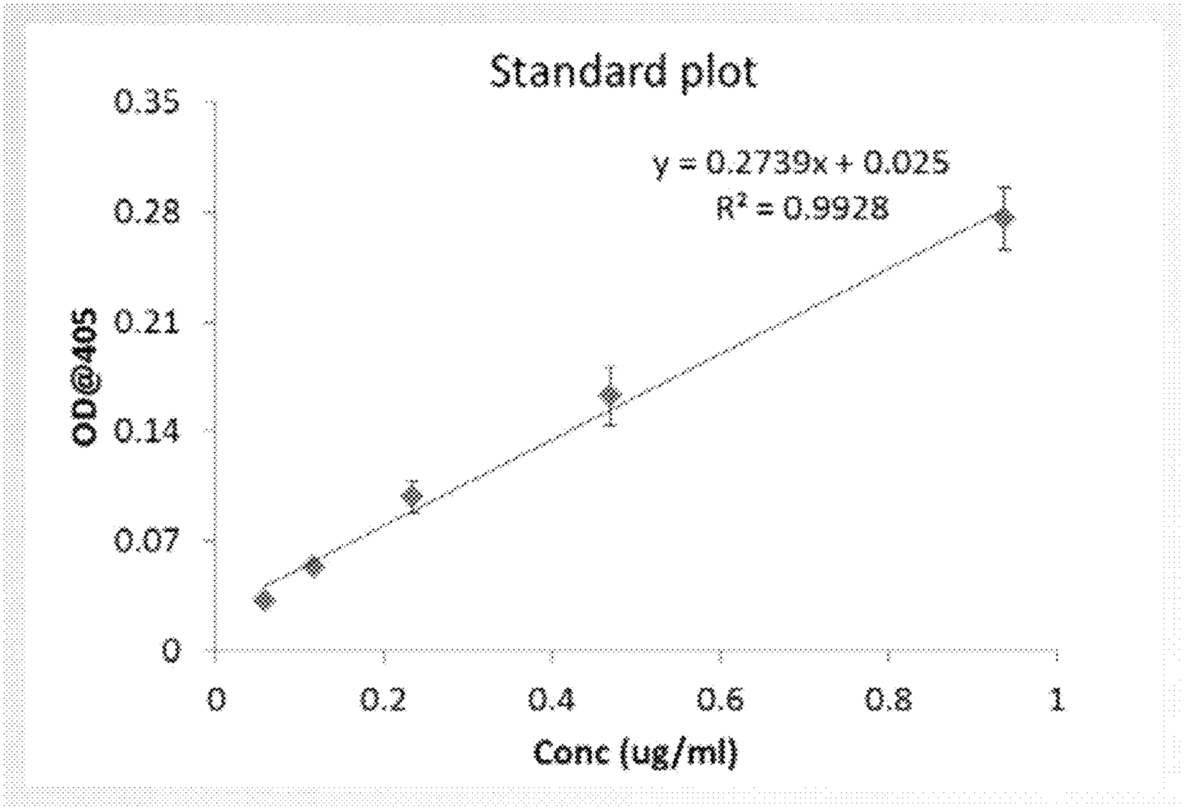
FIGS. 10 and 11 are graphs of optical density at 405 nm as a function of concentration (μg/ml.
Figure 11:
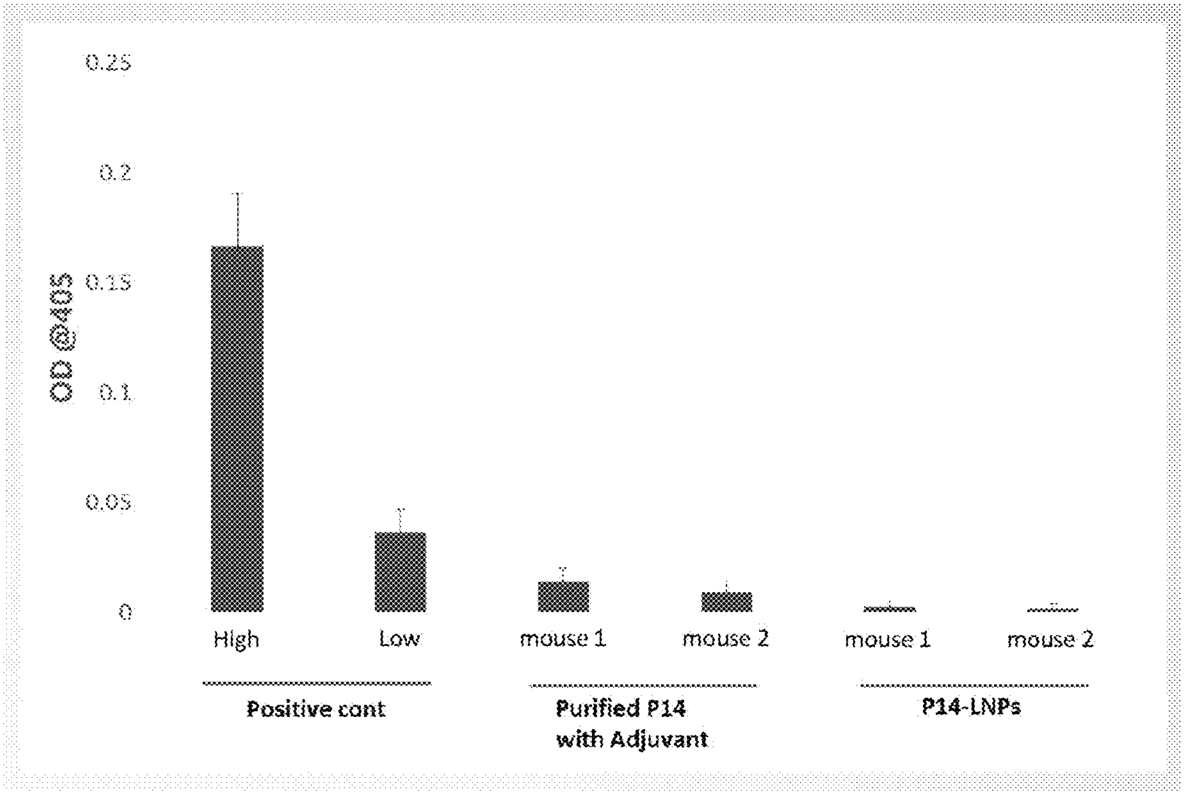

Mice were injected three (3) times at 10 day intervals with purified p14 mixed with Freund's adjuvant. A first dose contained CFA (complete Freund's adjuvant) while second and third doses contained IFA (incomplete Freund's adjuvant). Each injection was with 50 μg of p14. Mice were sacrificed after 30 days and sera was analyzed for anti-p14 antibodies. p14 lipid nanoparticles were also tested in two (2) mice via intravenous injection of 400 μg of p53-iCasp9 Fusogenix lipid nanoparticles containing 240 μg of p14. Mice were sacrificed after 30 days of injection and serum was analyzed for anti-p14 antibodies. A positive control included purified antibodies spiked in serum at a high dose of 250 ng/ml and a low dose of 50 ng/ml. The data presented in FIGS. 10 and 11 demonstrate the safety and tolerability of Fusogenix™ lipid nanoparticles utilizing a reptilian reovirus p14 FAST fusion protein. Anti-p14 and anti-LNP antibody assays demonstrated that virtually no antibody response was observed in immune competent mice (with and without adjuvant).

Figure 12:
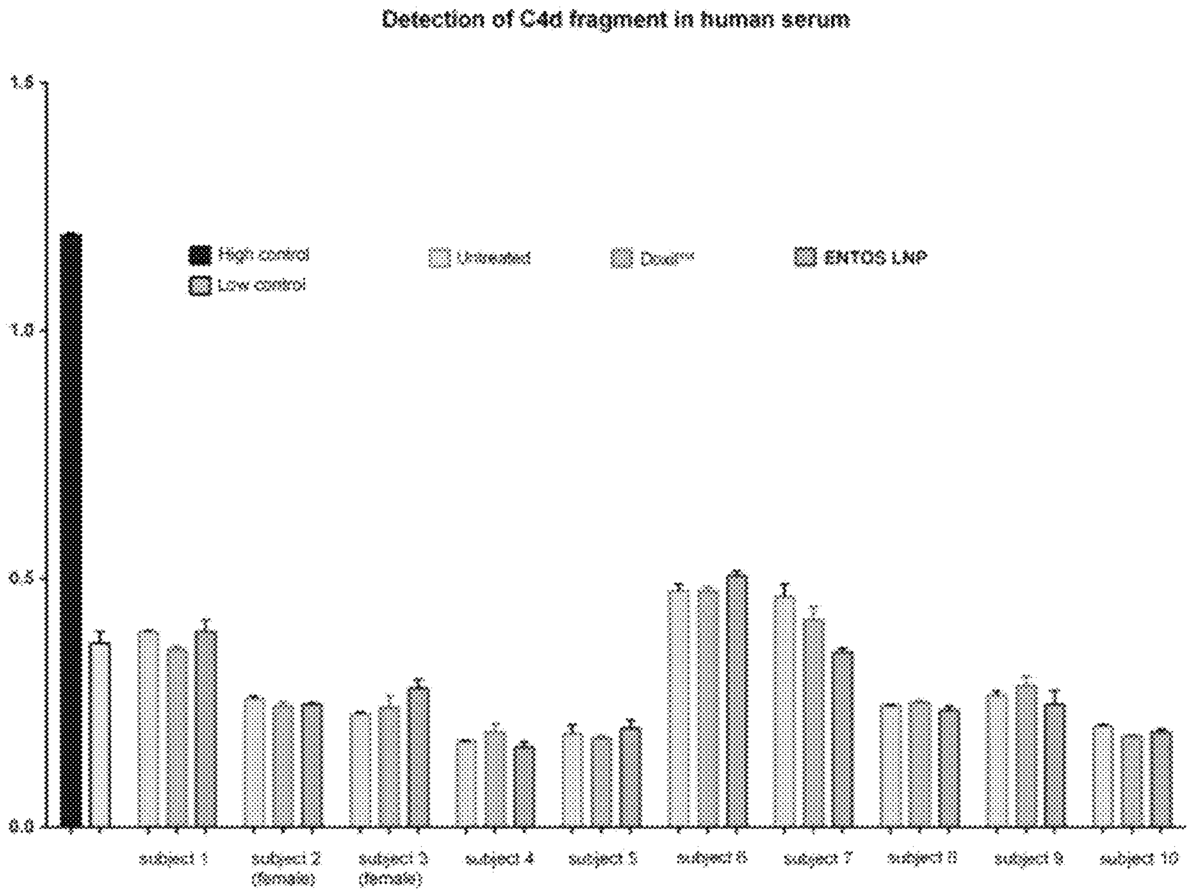
FIGS. 12 and 13 are bar graphs of data from in vitro anti-p14 and anti-LNP antibody neutralization assays showing that lipid nanoparticle formulations according to the present disclosure are non-reactive with C4d (FIG. 12) and less reactive with iC3b (FIG. 13) as compared to Doxil in 8 out of 10 human samples tested for Complement activation-related psuedoallergy (CARPA) using C4d and iC3b complement ELISA assays as described in Szebeni, *Mol Immunol* 61(2):163-73 (2014).
Figure 13:
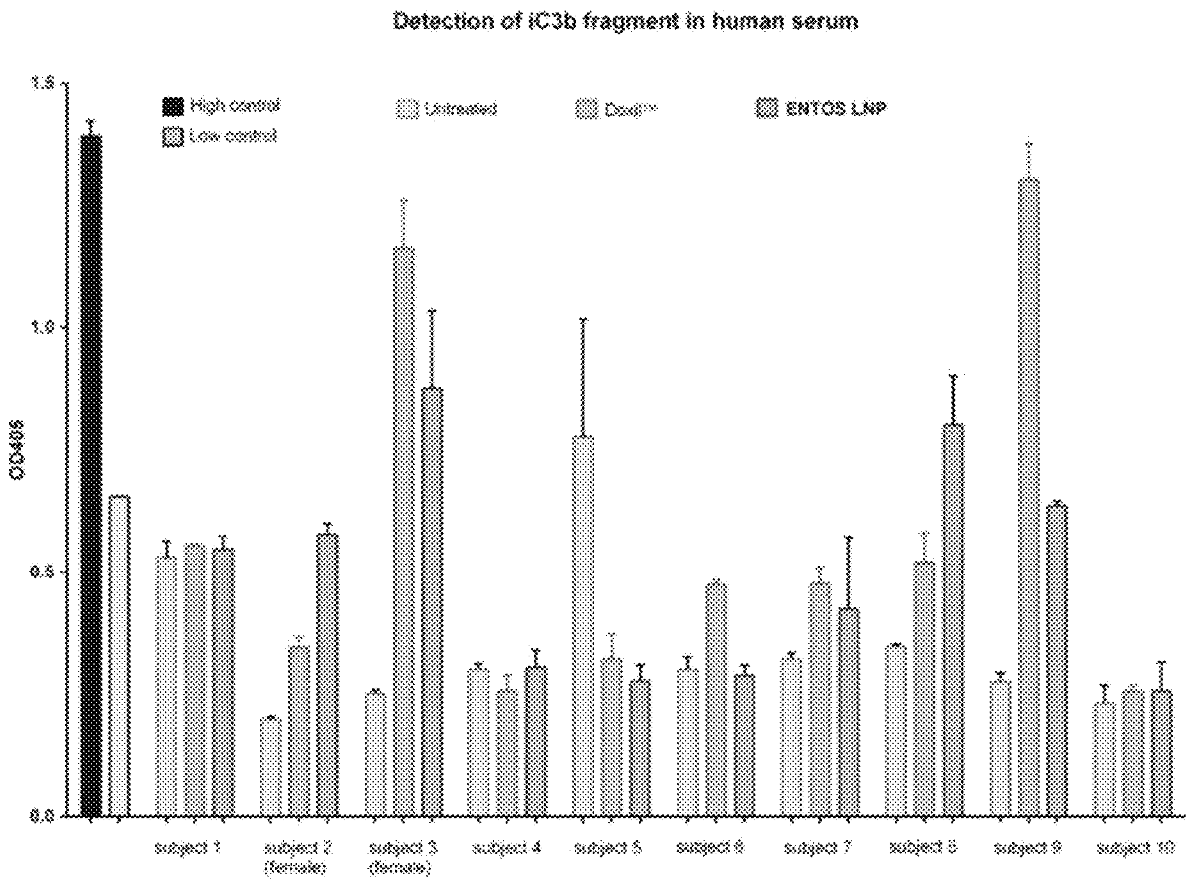

Ten (10) human serum samples were tested for Complement activation-related psuedoallergy (CARPA) using C4d and iC3b complement ELISA assays as described in Szebeni, *Mol Immunol* 61(2):163-73 (2014). The data presented in FIGS. 12 and 13 demonstrate that LNP formulations according to the present disclosure were non-reactive with C4d (FIG. 12) and less reactive with iC3b (FIG. 13) as compared to Doxil in 8 out of 10 human samples (approximately 5-10% of humans exhibit a CARPA reaction to nanomedicines such as Doxil).

In vitro anti-p14 and anti-LNP antibody neutralization assays revealed that vector neutralization required very high antibody concentrations. Moreover, vaccination or pretreatment with p14-LNPs did not result in a decrease in therapeutic efficacy and repeated in vivo dosing was effective and well tolerated. CARPA assays with Fusogenix™ p14 FAST lipid nanoparticles elicit less complement activity as compared to a control pegylated liposomal doxorubicin (Doxil).

Example 3

In Vivo Suppression of p16-Positive Senescent Cell Burden in Aged Mice

This Example demonstrates the target-cell specific suppression in p16-positive senescent cell burden following the in vivo administration of an exemplary p16-targeting construct in an mouse model system for aging.

The aging mouse model exhibits a senescent cell burden (as defined by the presence of p16$^+$ cells) and secretion of factors associated with a senescence-associated secretory phenotype (SASP; van Deursen, *Nature* 509(7501):439-446 (2014)).

Figure 17:
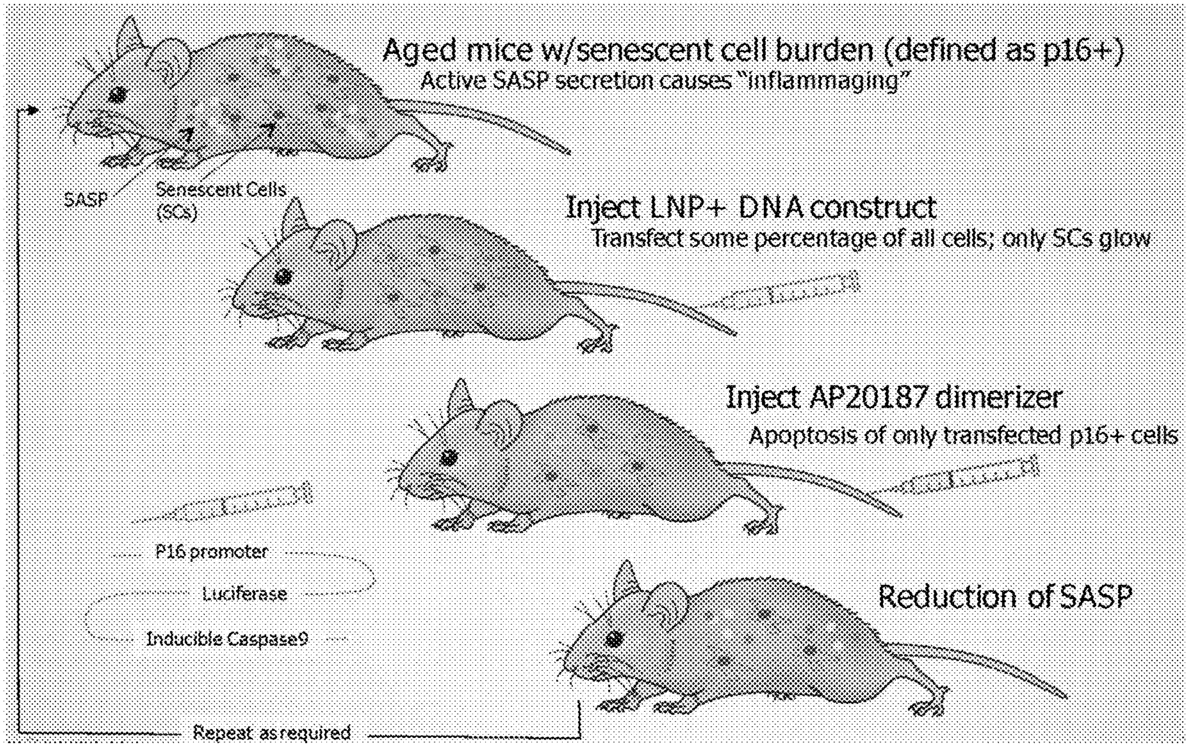
FIG. 17 is a diagrammatic representation of the in vivo administration of an exemplary p16-targeting construct in an mouse model system for aging, wherein the aging mouse model exhibits a senescent cell burden (as defined by the presence of $p16^+$ cells) and secretion of factors associated with a senescence-associated secretory phenotype (SASP; van Deursen, *Nature* 509(7501):439-446 (2014)). A formulation comprising a vector and an expression construct, such as a lipid nanoparticle (LNP) vector, e.g., a fusogenic LNP comprising a fusogenic protein such as p14 FAST, encompassing a p16-iCasp9 expression construct, e.g., pVAX1-16s-iCasp9 or variant thereof expressing luciferase (for visualization), is administered in vivo to an aged mouse via injection into a tail vein and the LNP+expression construct transfects target and non-target cells without specificity. Upon subsequent in vivo administration of a chemical inducer of dimerization (CID), such as AP20187, p16+ target cells (e.g., senescent cells) undergo apoptosis, resulting in a reduction is SASP levels, while p16− cells remain viable.

A formulation comprising a vector and an expression construct, such as a lipid nanoparticle (LNP) vector, e.g., a fusogenic LNP comprising a fusogenic protein such as p14 FAST, encompassing a p16-iCasp9 expression construct (pVAX1-16s-iCasp9; SEQ ID NO: 06; FIG. 16) which comprises an exemplary p16-targeting construct for the target cell-specific expression of an inducible Caspase 9 (iCasp9) protein in target cells expressing p16, such as target cells that are associated with aging and/or senescence, which p16-targeting construct comprises a p16s transcriptional promoter in operable connection to iCasp9. or variant thereof expressing luciferase (for visualization), was administered in vivo to an aged mouse via injection into a tail vein and the LNP+expression construct transfects target and non-target cells without specificity. FIG. 17. Upon subsequent in vivo administration of the chemical inducer of dimerization (CID), AP20187, p16+ target cells (e.g., senescent cells) underwent apoptosis, resulting in a reduction is SASP levels, while p16− cells remained viable.

Figure 18:
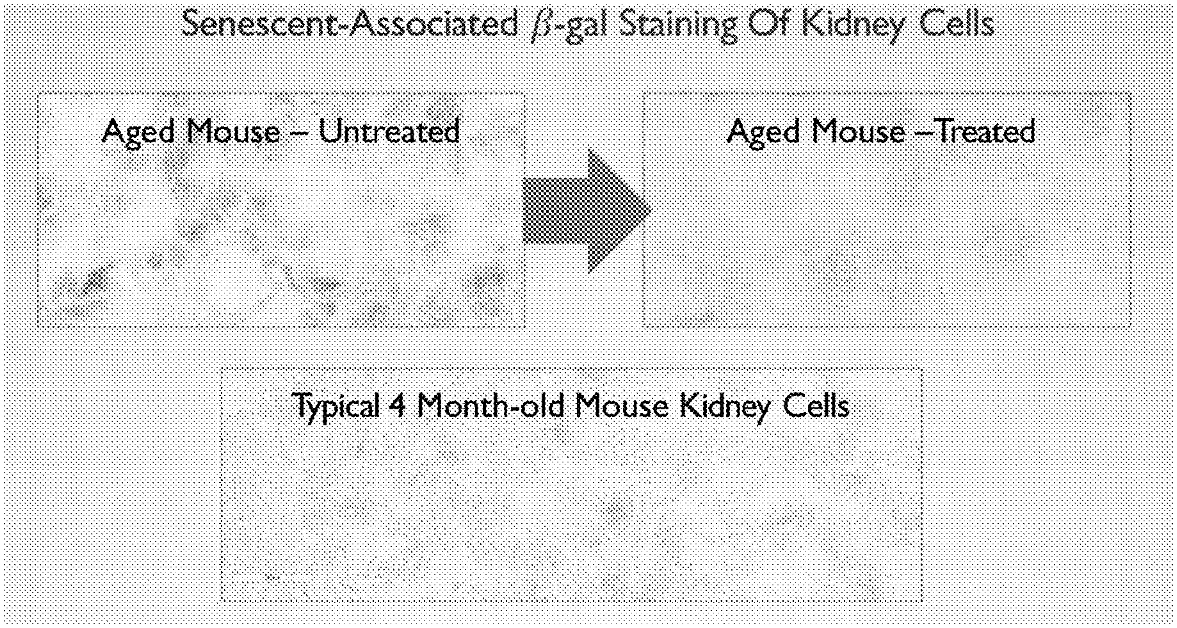
FIG. 18 is a photomicrograph of the histological staining of senescent-associated β-gal in kidney cells from an in vivo aged mouse model either untreated (upper left panel) or treated (upper right panel) following the in vivo administration (16 animals at 80 weeks of age) of a formulation comprising a vector and an expression construct, such as a lipid nanoparticle (LNP) vector, e.g., a fusogenic LNP comprising a fusogenic protein such as p14 FAST, encompassing a p16-iCasp9 expression construct, e.g., pVAX1-16s-iCasp9 or variant thereof, is administered in vivo to an aged mouse and kidney cells stained for β-gal. The lower panel is a photomicrograph of the histological staining of senescent-associated β-gal in 4-month old kidney cells from a normal mouse. These data demonstrated a dose-dependent reduction of p16+ senescent kidney cells.

Histological staining of senescent-associated β-gal in kidney cells from an in vivo aged mouse model either untreated (upper left panel) or treated (upper right panel) following the in vivo administration (16 animals at 80 weeks of age) of a formulation comprising a vector and an expression construct, such as a lipid nanoparticle (LNP) vector, e.g., a fusogenic LNP comprising a fusogenic protein such as p14 FAST, encompassing a p16-iCasp9 expression construct, e.g., pVAX1-16s-iCasp9 or variant thereof, was administered in vivo to an aged mouse and kidney cells stained for β-gal. FIG. 18. The lower panel is a photomicrograph of the histological staining of senescent-associated β-gal in 4-month old kidney cells from a normal mouse. These data demonstrated a dose-dependent reduction of p16+ senescent kidney cells.

Figure 19:
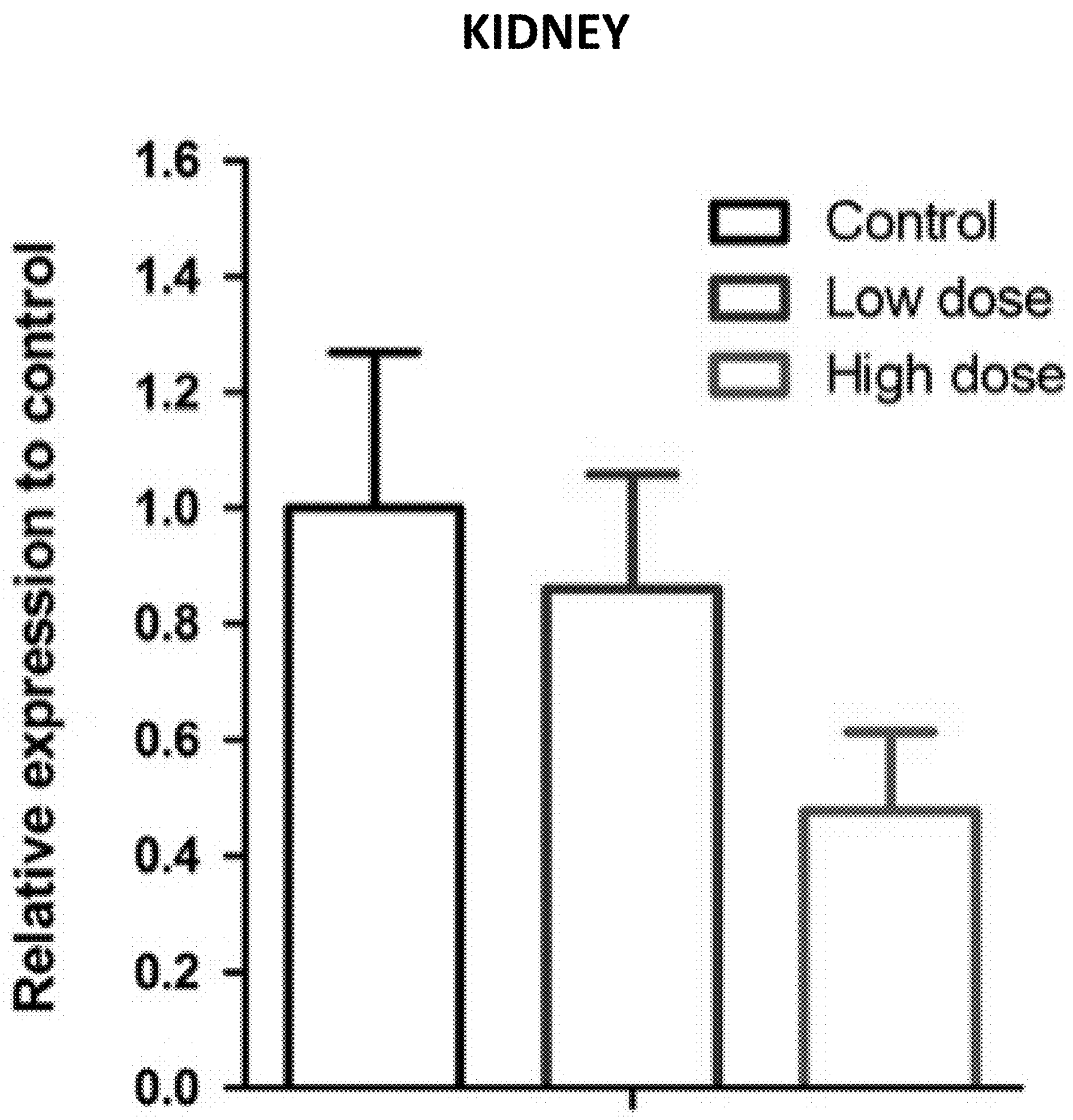
FIG. 19 is a bar graph demonstrating the dose-dependent targeting of p16+ kidney cells in naturally aged mice following the in vivo administration of a fusogenic lipid nanoparticle (LNP) formulation comprising a pVAX1-p16 expression construct. Kidney cells were subjected to a qRT-PCR reaction to detect $p16^{Ink4a}$ transcripts. Relative expression was calculated using 2ΔΔCt (Livak, *Methods* 25:402-408 (2001)).
Figure 20:
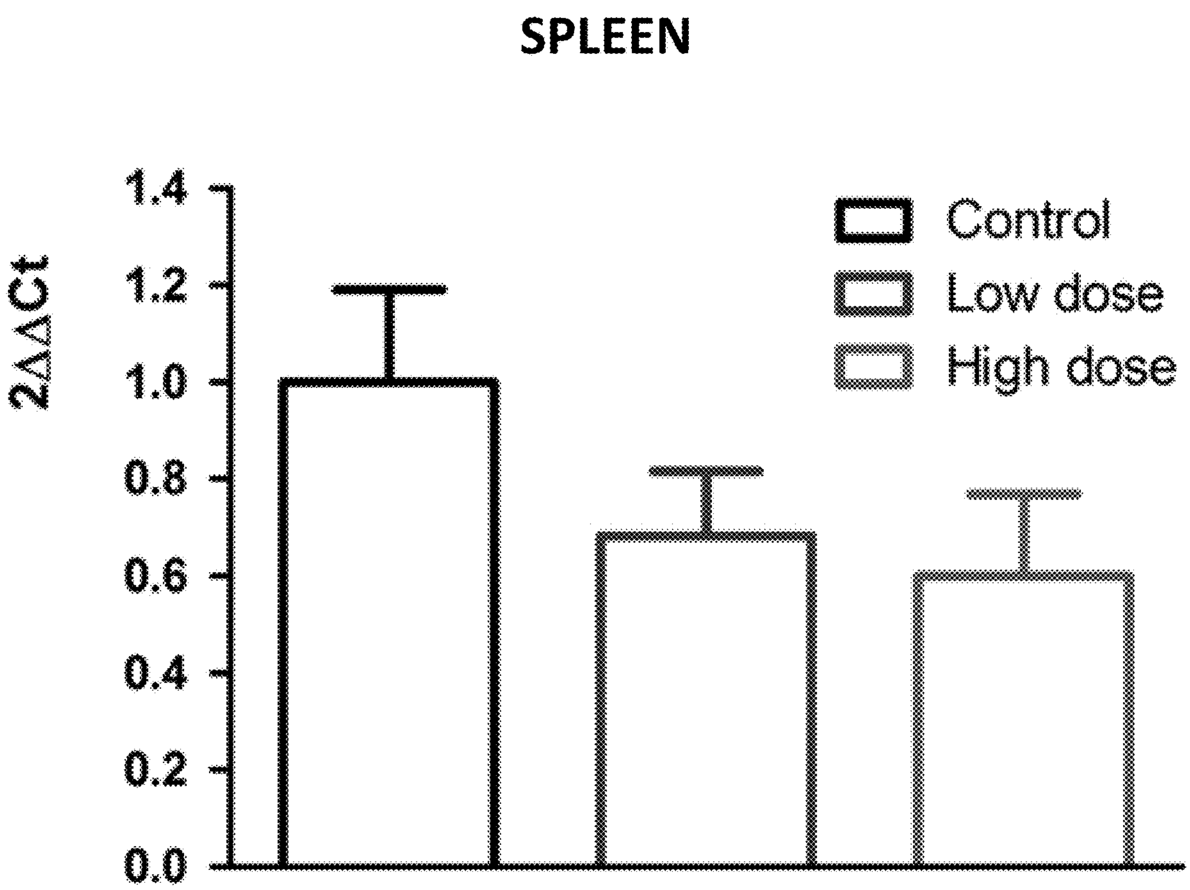
FIG. 20 is a bar graph demonstrating the dose-dependent targeting of p16+ spleen cells in naturally aged mice following the in vivo administration of a fusogenic lipid nanoparticle (LNP) formulation comprising a pVAX1-p16 expression construct. Spleen cells were subjected to a qRT-PCR reaction to detect $p16^{Ink4a}$ transcripts. Relative expression was calculated using 2ΔΔCt (Livak, *Methods* 25:402-408 (2001)).
Figure 21:
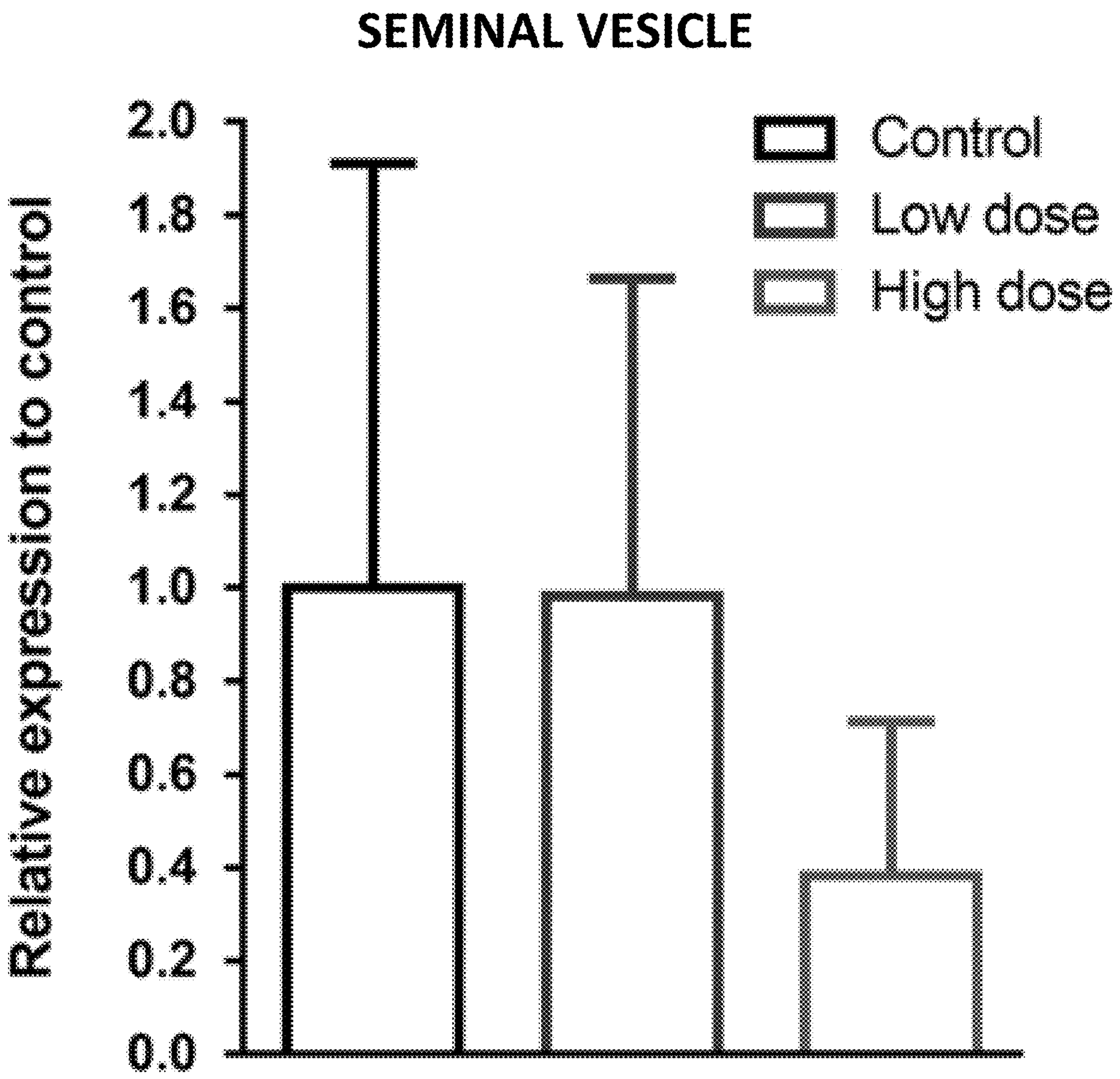
FIG. 21 is a bar graph demonstrating the dose-dependent targeting of p16+ seminal vesicle cells in naturally aged mice following the in vivo administration of a fusogenic lipid nanoparticle (LNP) formulation comprising a pVAX1-p16 expression construct. Seminal vesicle cells were subjected to a qRT-PCR reaction to detect $p16^{Ink4a}$ transcripts. Relative expression was calculated using 2ΔΔCt (Livak, *Methods* 25:402-408 (2001)).
Figure 22:
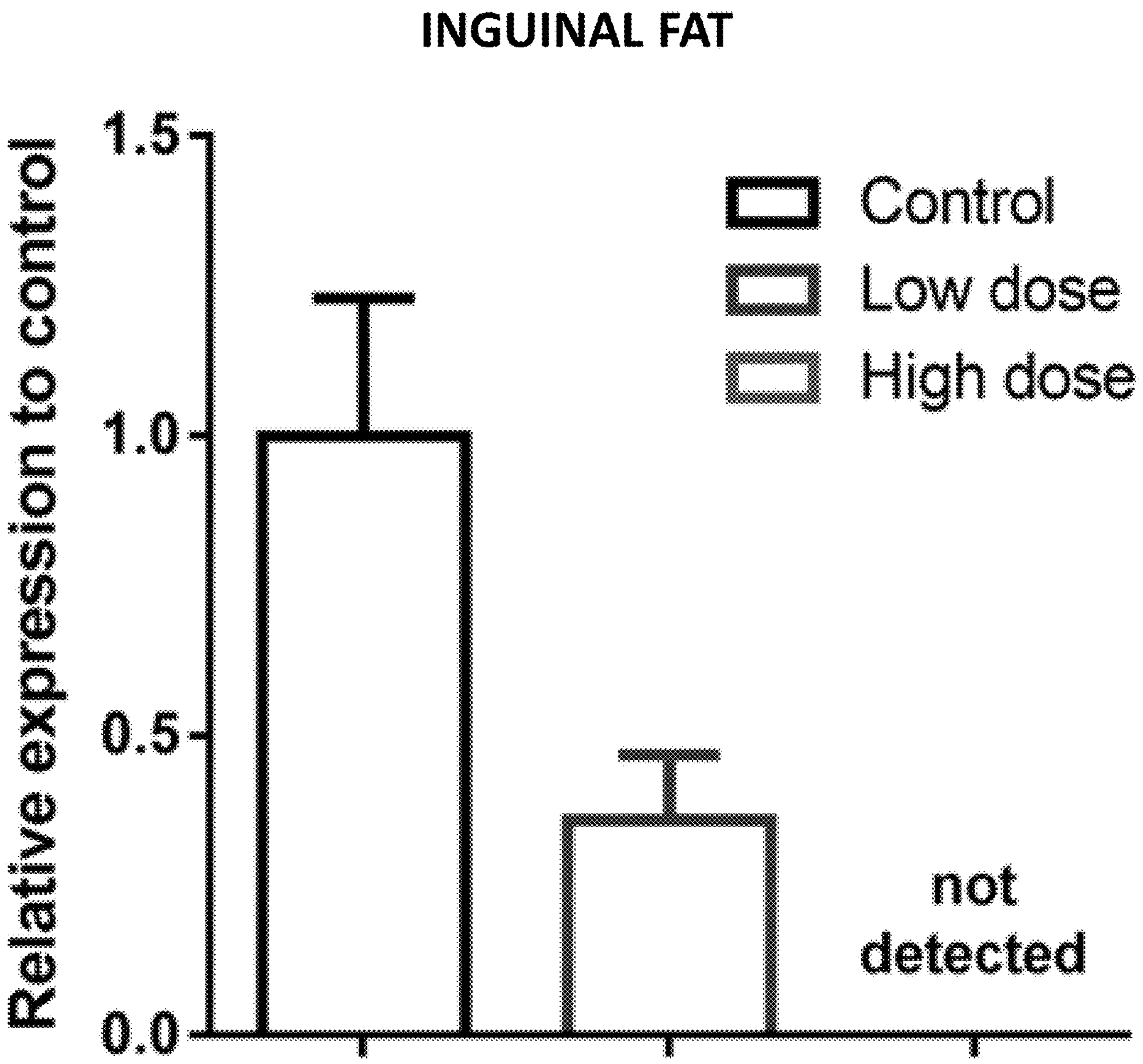
FIG. 22 is a bar graph demonstrating the dose-dependent targeting of p16+ inguinal fat cells in naturally aged mice following the in vivo administration of a fusogenic lipid nanoparticle (LNP) formulation comprising a pVAX1-p16 expression construct. Inguinal fat cells were subjected to a qRT-PCR reaction to detect $p16^{Ink4a}$ transcripts. Relative expression was calculated using 2ΔΔCt (Livak, *Methods* 25:402-408 (2001)).
Figure 23:
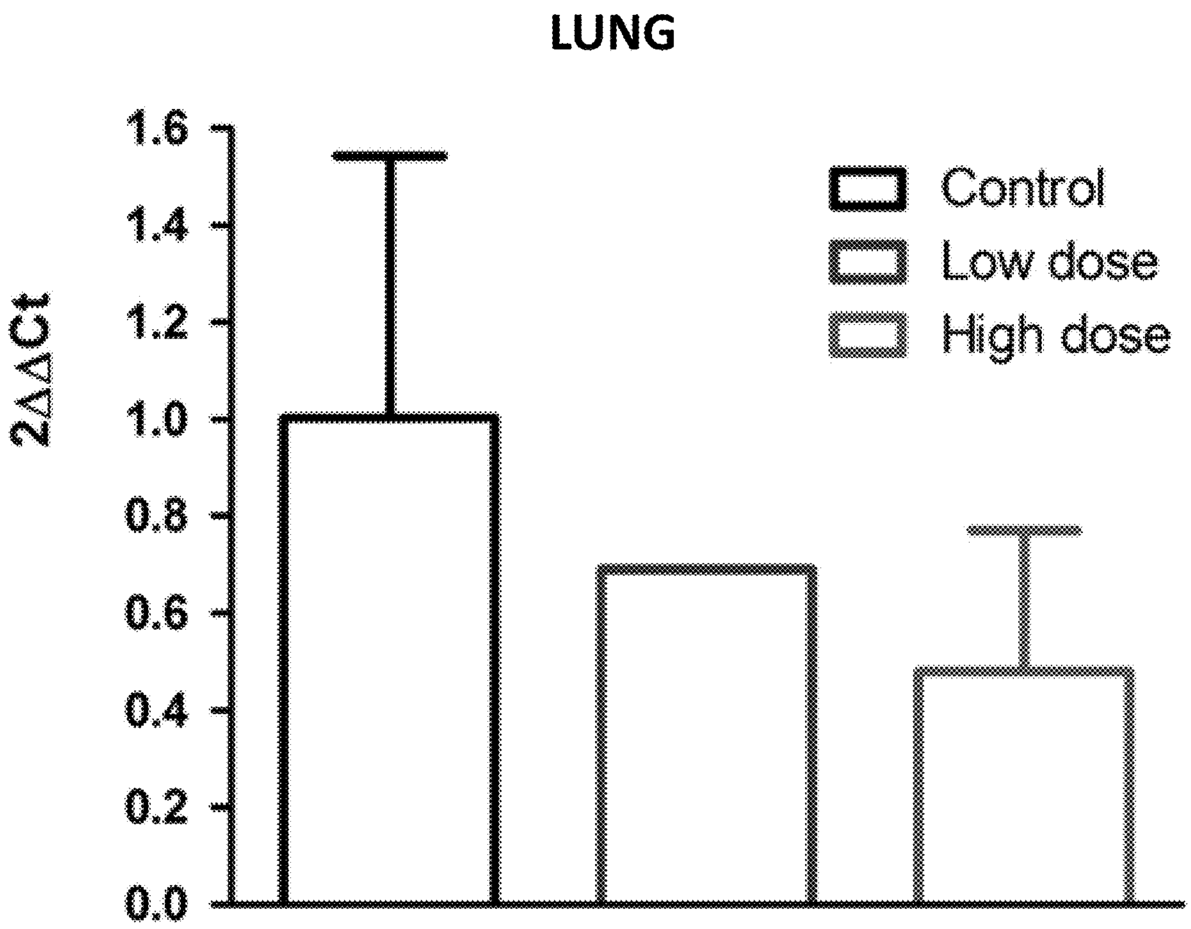
FIG. 23 is a bar graph demonstrating the dose-dependent targeting of p16+ lung cells in naturally aged mice following the in vivo administration of a fusogenic lipid nanoparticle (LNP) formulation comprising a pVAX1-p16 expression construct. Lung cells were subjected to a qRT-PCR reaction to detect $p16^{Ink4a}$ transcripts. Relative expression was calculated using 2ΔΔCt (Livak, *Methods* 25:402-408 (2001)).
Figure 24:
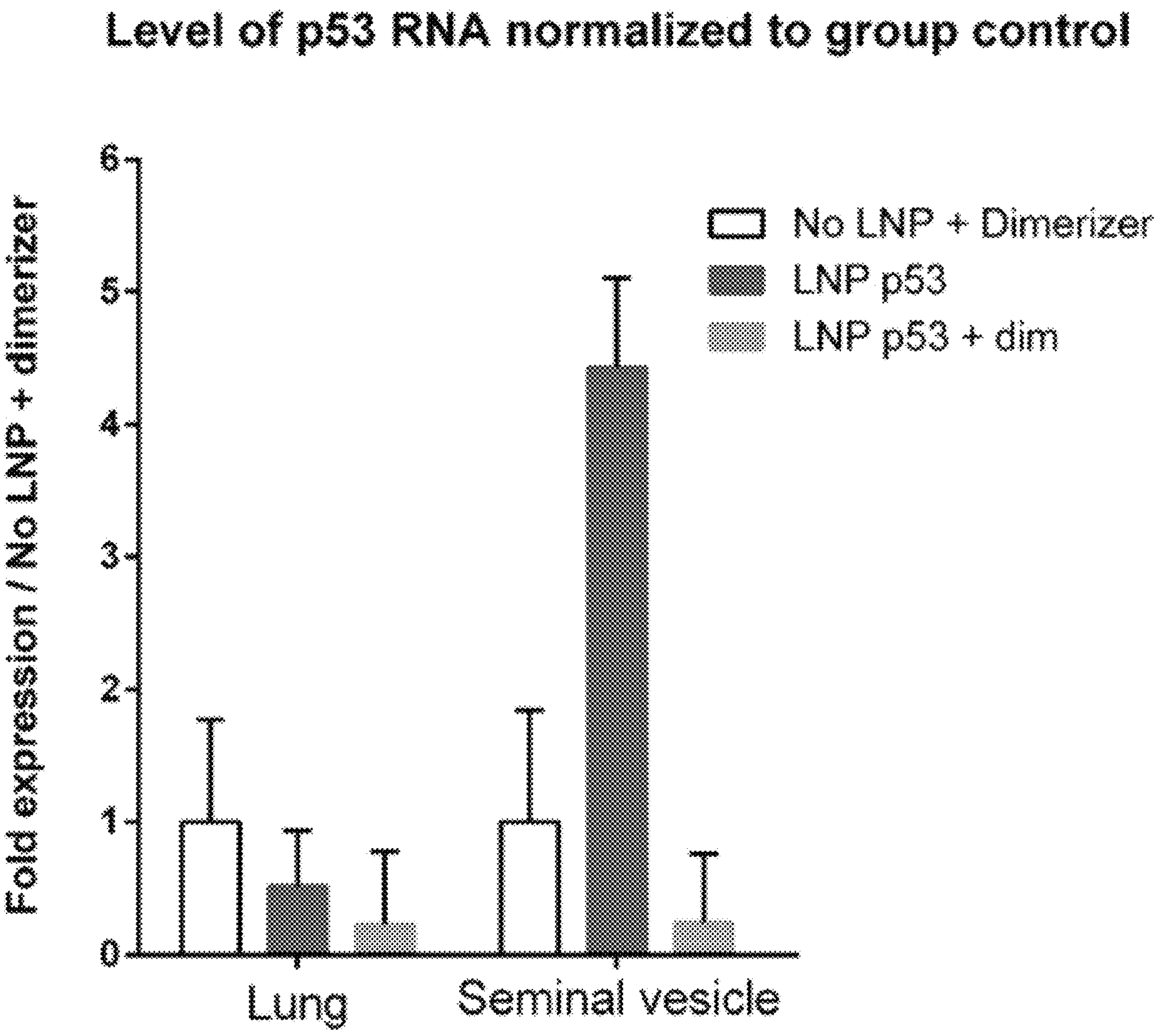
FIG. 24 is a bar graph of data demonstrating the remediation of chemotherapy-induced damage (as determined by the clearance of damaged cells (i.e., senescent cells) after treatment with doxorubicin). Senescence was induced in B6 mice with doxorubicin. Animals were treated with murine p53-iCasp9 and dimerizer or controls (dimerizer only and LNP only) and sacrificed. Tissues were assayed for p53 expression via rt-PCR.
Figure 25:
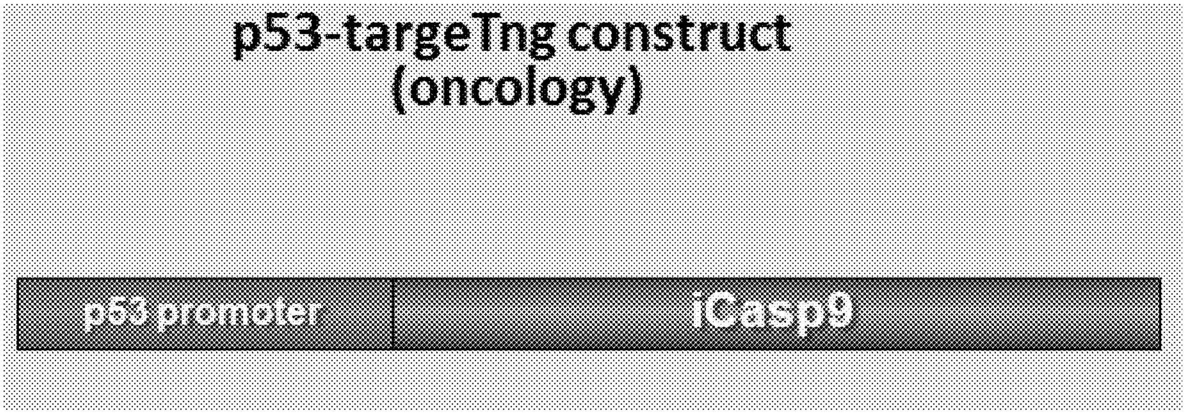
FIG. 25 is a diagrammatic representation of an exemplary p53-targeting cassette for use in treatment of cancers (oncology) by the selective killing of tumor cells according certain embodiments of the present disclosure. The p53-targeting cassette comprises a p53 transcriptional promoter, which drives the expression an inducible caspase 9 protein (iCasp9).

The dose-dependent targeting of p16+ kidney cells (FIG. 19), spleen cells (FIG. 20), seminal vesicle cells (FIG. 21), inguinal fat cells (FIG. 22), and lung cells (FIG. 23) was demonstrated in naturally aged mice following the in vivo administration of a fusogenic lipid nanoparticle (LNP) formulation comprising a pVAX1-p16 expression construct. Kidney cells were subjected to a qRT-PCR reaction to detect $p16^{Ink4a}$ transcripts. Relative expression was calculated using 2ΔΔCt (Livak, *Methods* 25:402-408 (2001)).

Example 4

In Vivo Oncology Study with NSG Mice Implanted with a Human Prostate Tumor

This Example demonstrates the target-cell specific suppression of p53-expressing prostate cancer cells in NSG mice implanted with a human prostate tumor (i.e., a PC-3 xenograft).

Figure 32:
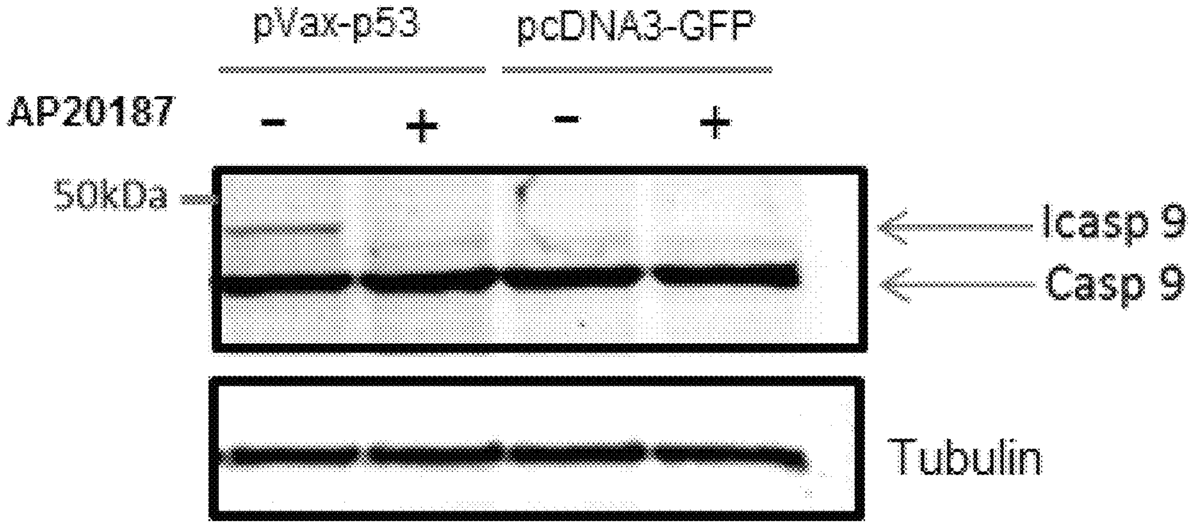
FIG. 32 is a Western blot of iCasp 9 and Casp 9 protein levels obtained with p53-expressing cells (pVax-p53) and control cells (pcDNA3-GFP). Human prostate cancer PC-3 cells were treated with Fusogenix lipid nanoparticles carrying the pVax-p53-iCasp9-luc (luciferin) plasmid (in the presence and absence of the homodimerizer AP201870) and assessed for iCasp9 expression. These data demonstrate that addition of the chemical inducer of dimerization (CID; e.g., AP20187 and AP1903) abolishes the expression of iCasp9 and luciferase in p53-expressing cells engineered to express iCasp9 or luciferase.

Human prostate cancer PC-3 cells were treated with Fusogenix lipid nanoparticles carrying the pVax-p53-iCasp9-luc (luciferin) plasmid (in the presence and absence of the homodimerizer AP201870) and assessed for iCasp9 expression and subjected to Western blot analysis of iCasp 9 and Casp 9 protein levels obtained with p53-expressing cells (pVax-p53) and control cells (pcDNA3-GFP). FIG. 32. These data demonstrated that the addition of the chemical inducer of dimerization (CID; e.g., AP20187 and AP1903) abolishes the expression of iCasp9 and luciferase in p53-expressing cells engineered to express iCasp9 or luciferase.

Figure 33:
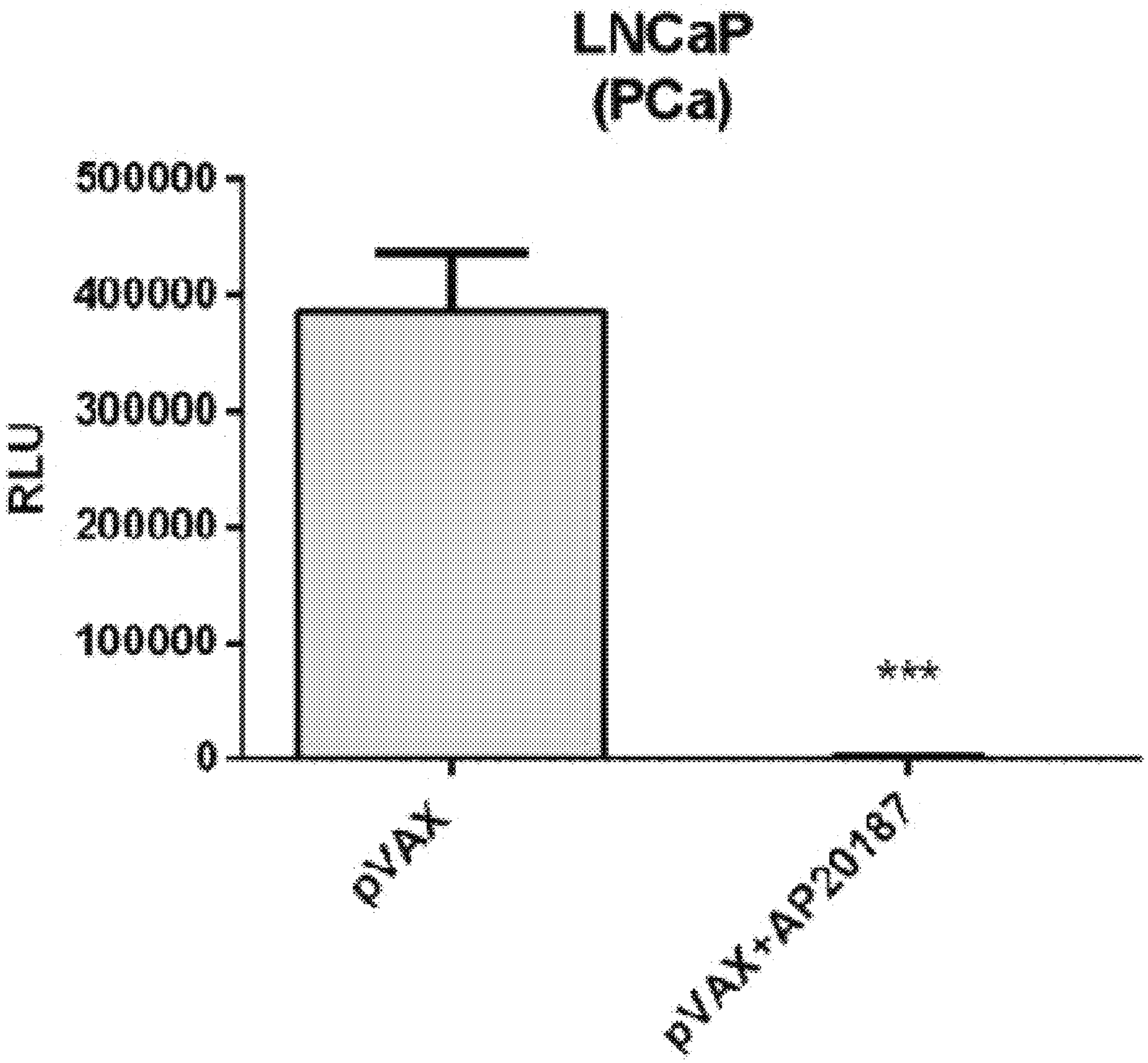
FIGS. 33-36 are bar graphs of data obtained with the p53-expressing cells presented in FIG. 32. Human prostate cancer (LNCaP (FIG. 33), DU145 (FIG. 34), PC-3 (FIG. 35) or normal epithelial (RWPE (FIG. 36)) cells were treated with Fusogenix lipid nanoparticles carrying the pVax-p53-iCasp9-luc plasmid and assessed for iCasp9 expression by Western blot and luminescence assays. These data demonstrate that addition of the chemical inducer of dimerization (CID; e.g., AP20187 and AP1903) abolishes the expression of iCasp9 and luciferase in p53-expressing cells engineered to express iCasp9 or luciferase.
Figure 34:
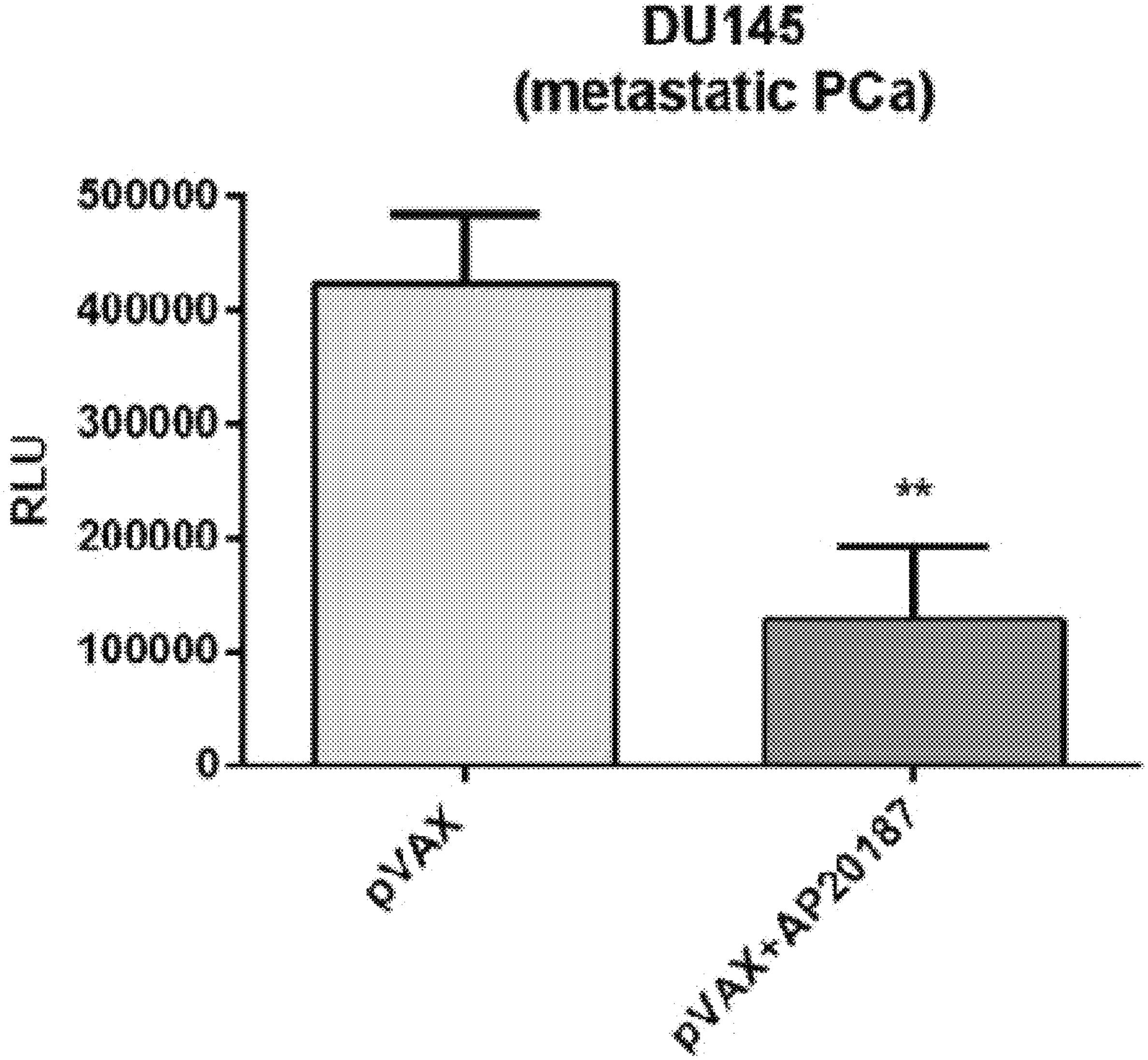
Figure 35:
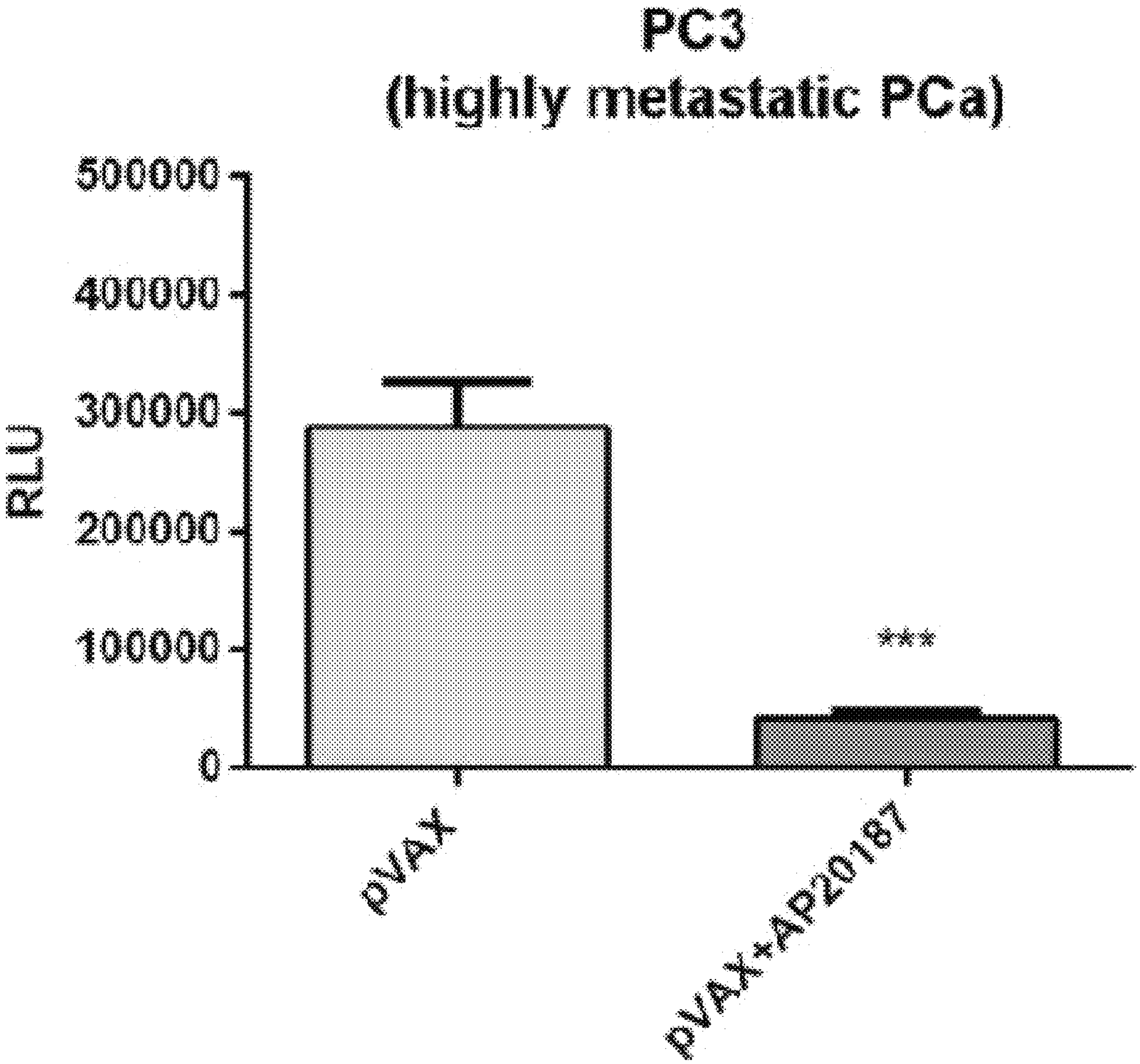
Figure 36:
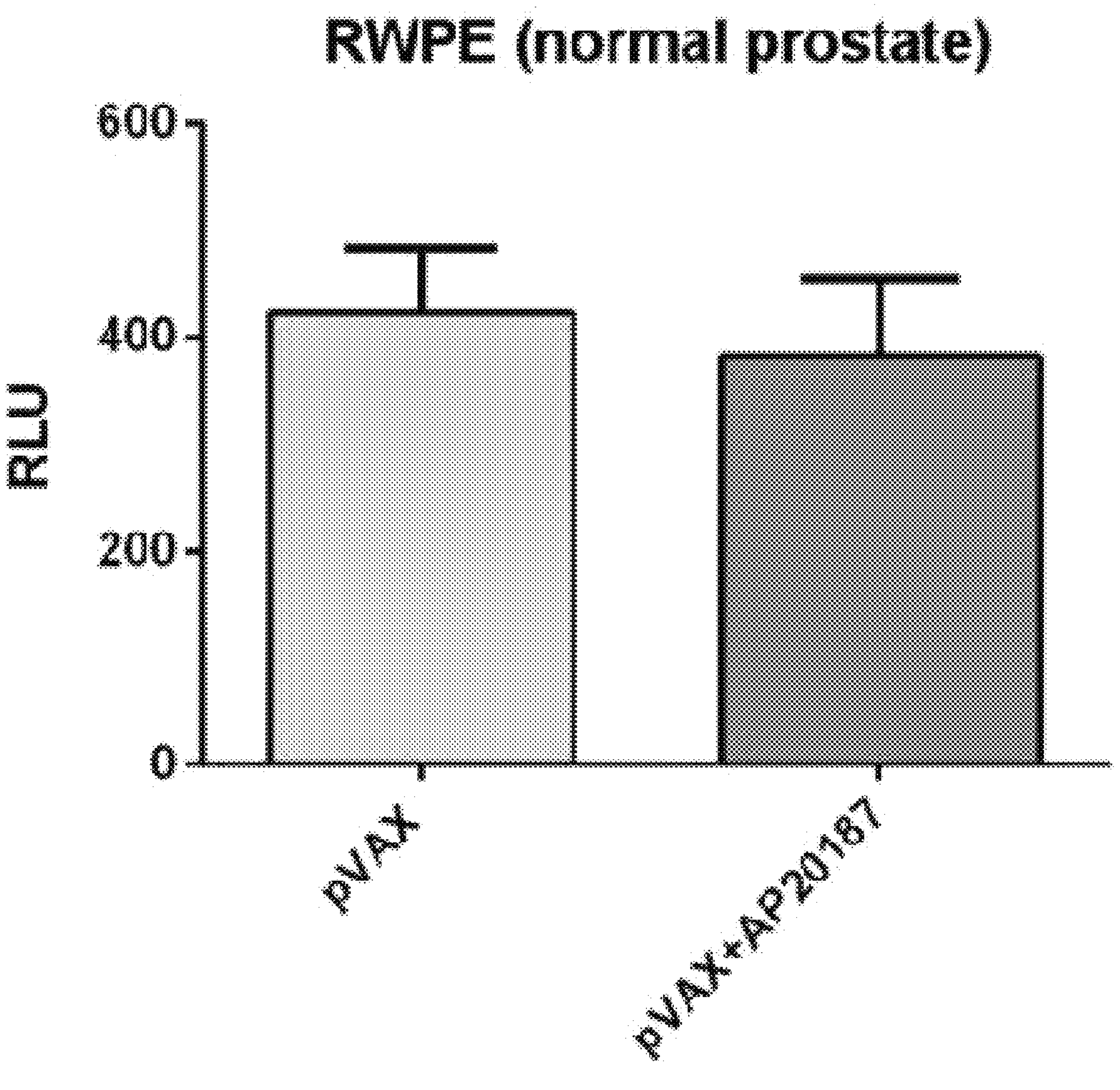

Human prostate cancer cells (LNCaP (FIG. 33), DU145 (FIG. 34), and PC-3 (FIG. 35)) and normal epithelial cells (RWPE (FIG. 36)) were treated with Fusogenix lipid nanoparticles carrying the pVax-p53-iCasp9-luc plasmid and assessed for iCasp9 expression by Western blot and luminescence assays. These data demonstrated that addition of the chemical inducer of dimerization (CID; e.g., AP20187 and AP1903) abolished the expression of iCasp9 and luciferase in p53-expressing cells engineered to express iCasp9 or luciferase.

Figure 37:
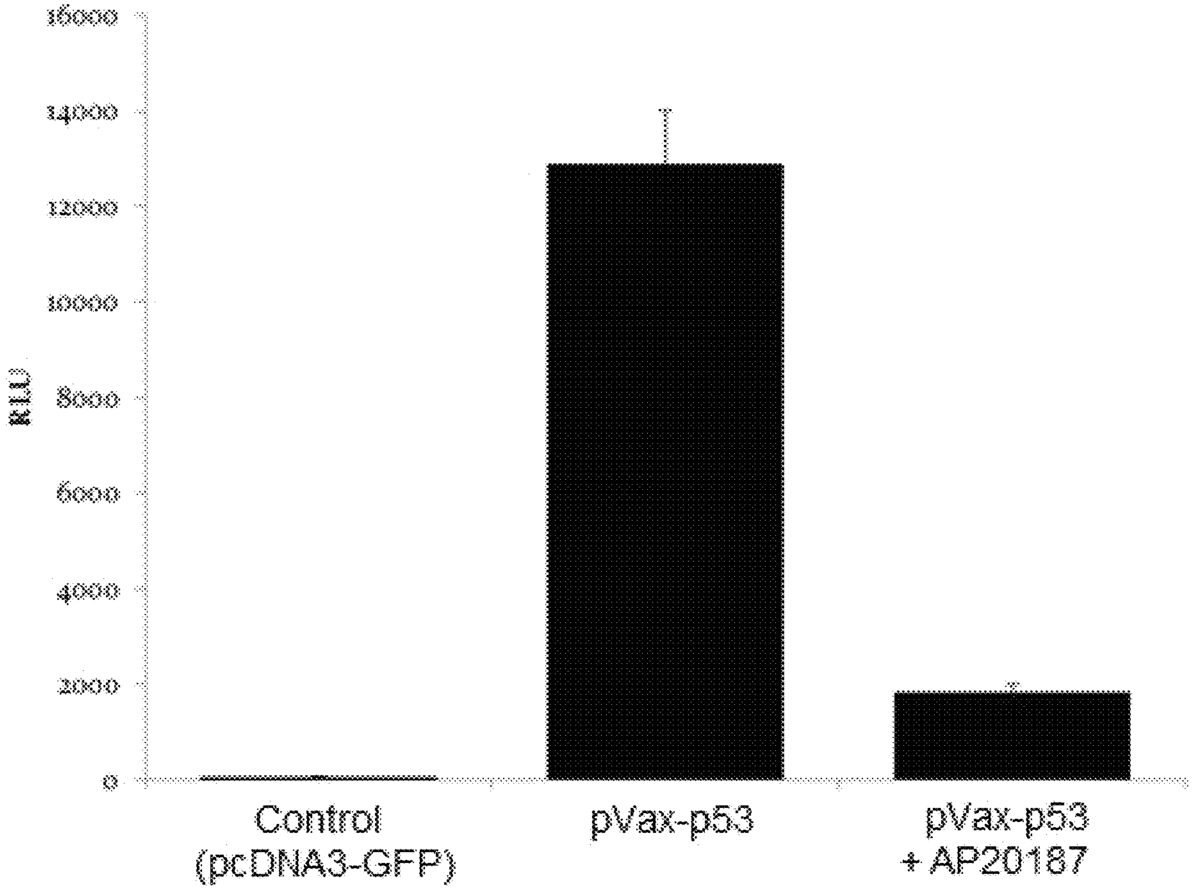
FIG. 37 is a bar graph of data from a luminescence assay of iCasp 9 and Casp 9 protein levels obtained with the p53-expressing cells presented in FIG. 32 (pVax-p53) and control cells (pcDNA3-GFP). Human prostate cancer PC-3 cells were treated with Fusogenix lipid nanoparticles carrying the pVax-p53-iCasp9-luc (luciferin) plasmid (in the presence and absence of the homodimerizer AP20187) and assessed for iCasp9 expression. These data demonstrate that addition of the chemical inducer of dimerization (CID; e.g., AP20187 and AP1903) abolishes the expression of iCasp9 and luciferase in p53-expressing cells engineered to express iCasp9 or luciferase.
Figure 38A:
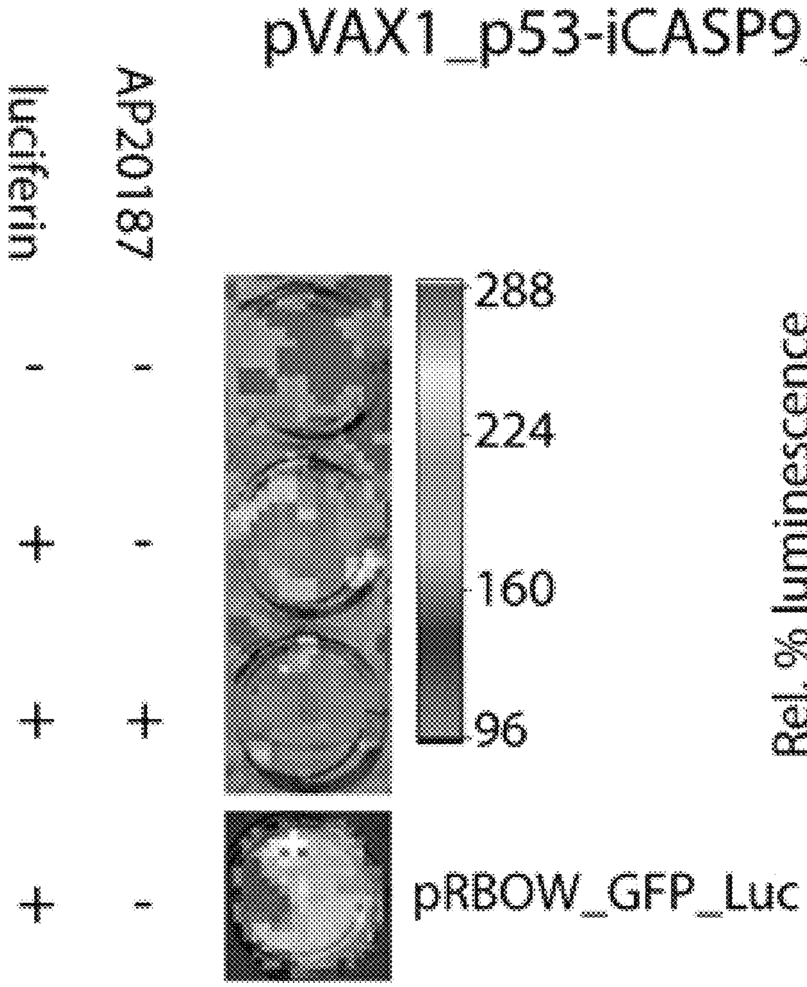
FIGS. 38A, 38B, 39A, and 39B are flow cytometry apoptosis data (Annexin V) from human prostate cancer PC-3 cells treated with pVax-p53 Fusogenix lipid nanoparticles (in the absence and presence of AP20187, FIGS. 38A and 39A and 38B and 39B, respectively). The data presented in these figures demonstrates that suicide gene therapy selectively kills p53-expressing human prostate cancer cells in culture by inducing apoptosis (Luciferase-Annexin V flow cytometry).
Figure 38B:
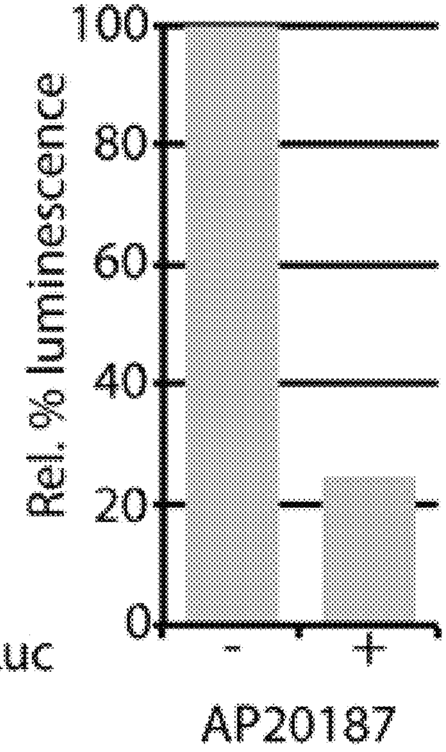
Figure 39A:
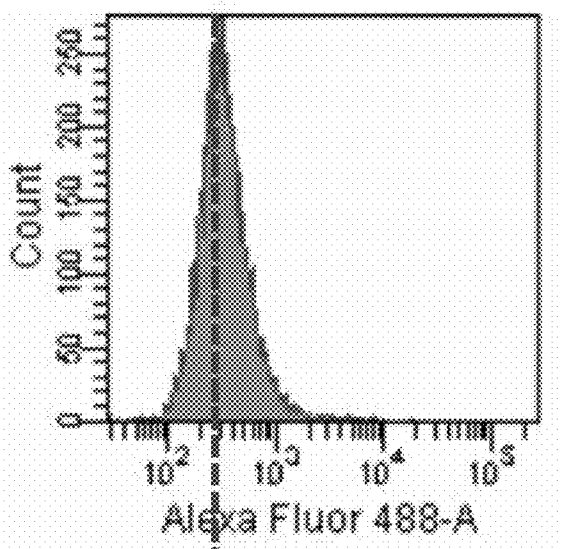
Figure 39B:
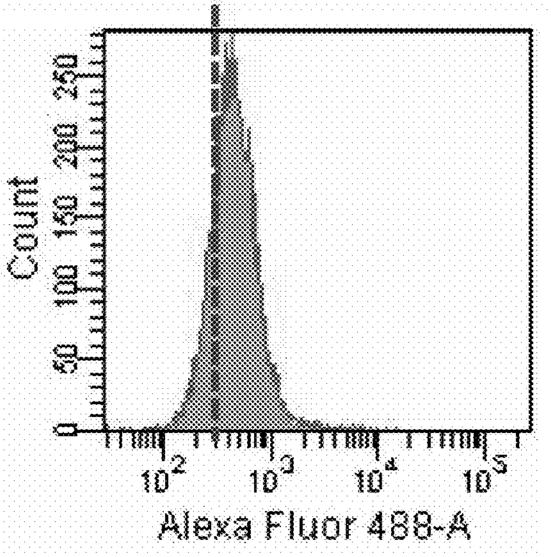

Human prostate cancer PC-3 cells were treated with Fusogenix lipid nanoparticles carrying the pVax-p53-iCasp9-luc (luciferin) plasmid (in the presence and absence of the homodimerizer AP20187) and assessed for iCasp9 expression. The data presented in FIG. 37 demonstrated that the addition of the chemical inducer of dimerization (CID; e.g., AP20187 and AP1903) abolished the expression of iCasp9 and luciferase in p53-expressing cells engineered to express iCasp9 or luciferase.

Flow cytometry apoptosis data (Annexin V) from human prostate cancer PC-3 cells treated with pVax-p53 Fusogenix lipid nanoparticles (in the absence and presence of AP20187, FIGS. 38A and 39A and 38B and 39B, respectively) demonstrated that suicide gene therapy selectively killed p53-expressing human prostate cancer cells in culture by inducing apoptosis (Luciferase-Annexin V flow cytometry).

Figure 40:
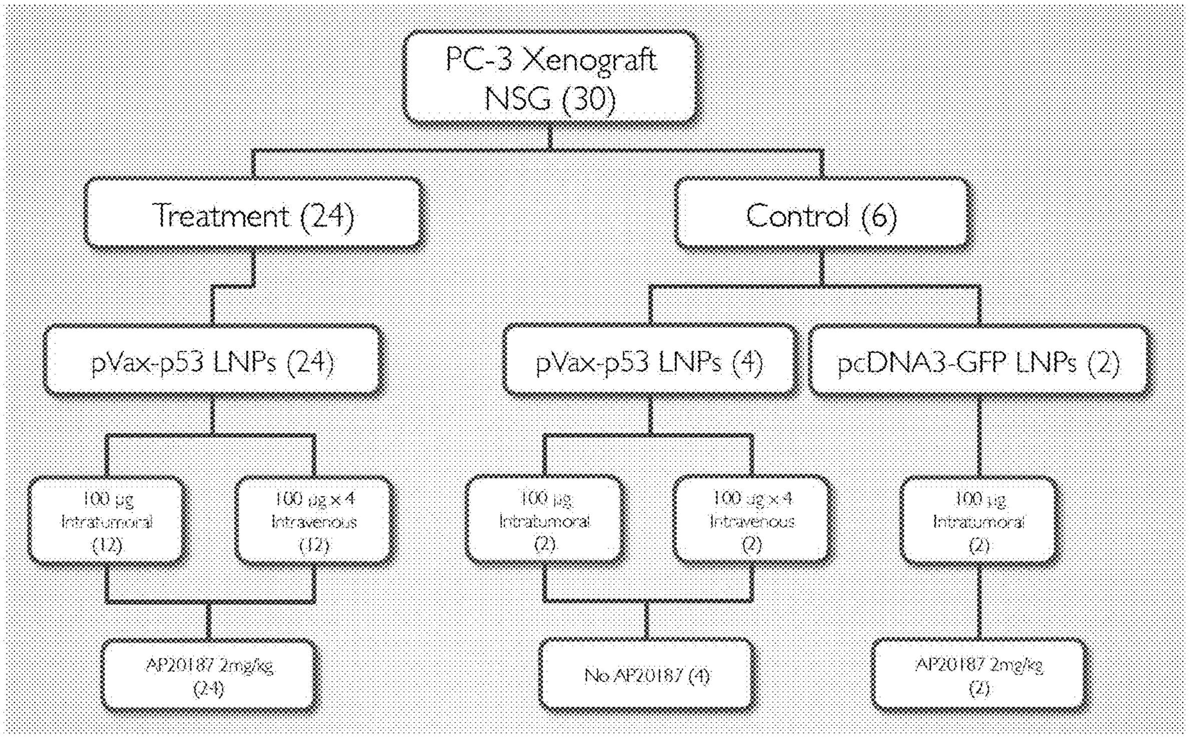
FIG. 40 is a flow diagram depicting a pre-clinical oncology study according to the present disclosure with 30×NSG mice implanted with human prostate tumor cells.
Figure 41:
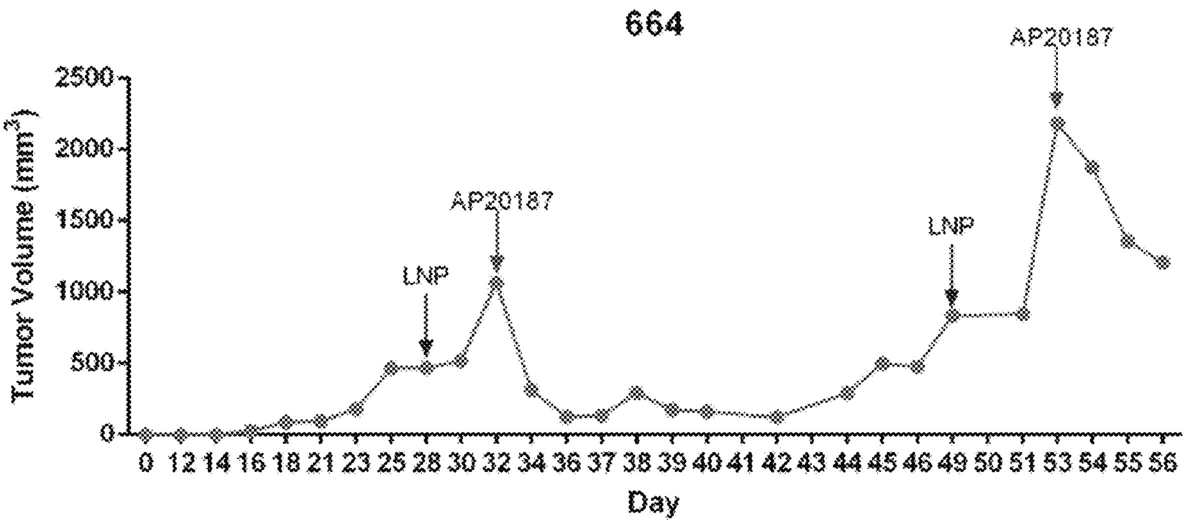
FIG. 41 is a graph of tumor volume ($mm^3$) from the pre-clinical oncology study depicted in FIG. 28 in which NSG mice bearing a subcutaneous human prostate PC-3 tumor was injected intratumorally (IT) with 100 μg Fusogenix pVax-p53 formulation, followed 96 hours later by intravenous (IV) administration of 2 mg/kg of the homodimerizer AP20187.
Figure 42A:
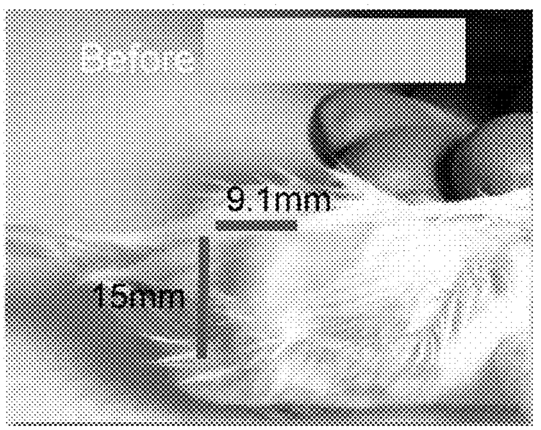
FIGS. 42A-42C are photographs of tumors from the IT injection oncology study of FIG. 41 in which NSG mouse bearing a subcutaneous human prostate PC-3 tumor was injected intratumorally with 100 μg Fusogenix pVax-p53 formulation, followed 96 hours by 2 mg/kg AP20187 IV.
Figure 42B:
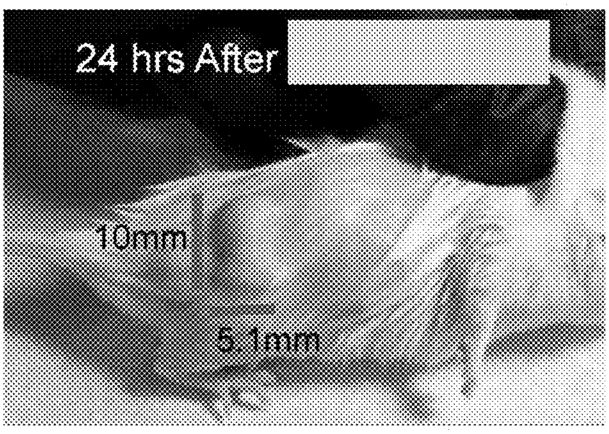
Figure 42C:
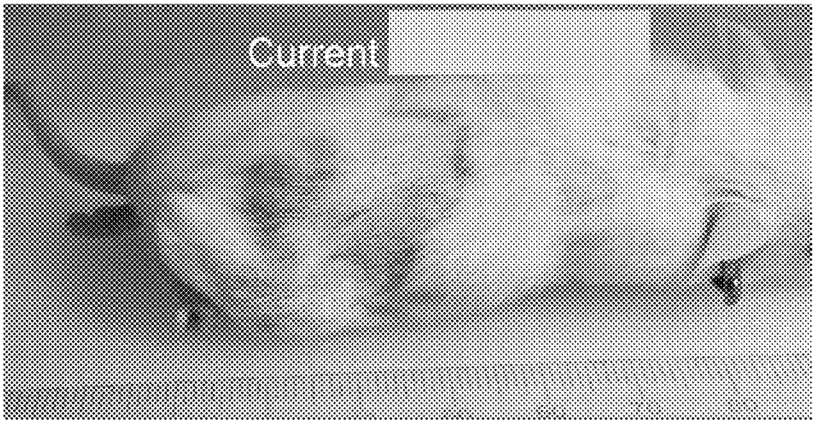
Figure 43:
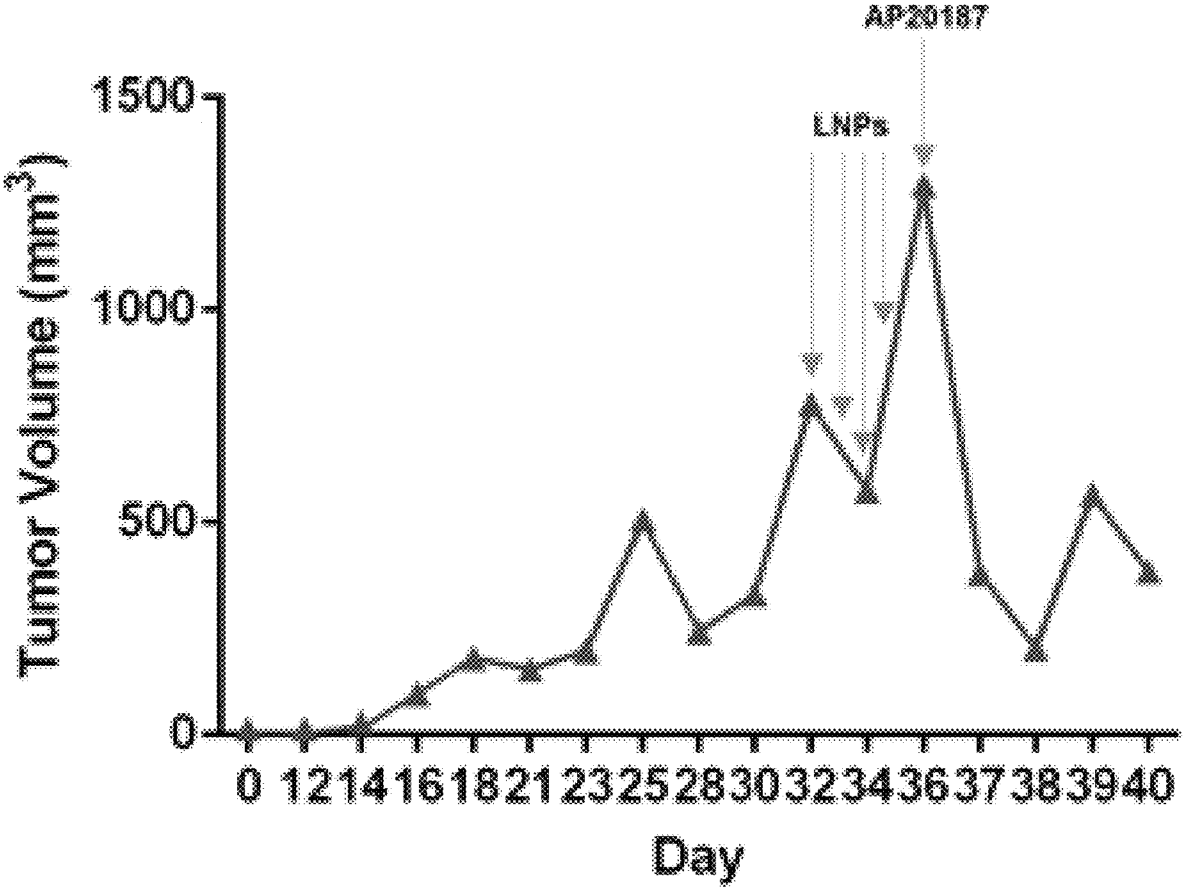
FIG. 43 is a graph from the first of four NSG mice bearing subcutaneous human prostate cancer PC-3 tumors that were injected intravenously (IV) with 4×100 μg doses of Fusogenix pVax-p53 formulation, followed 24 hours later by 2 mg/kg AP20187 IV.
Figure 44:
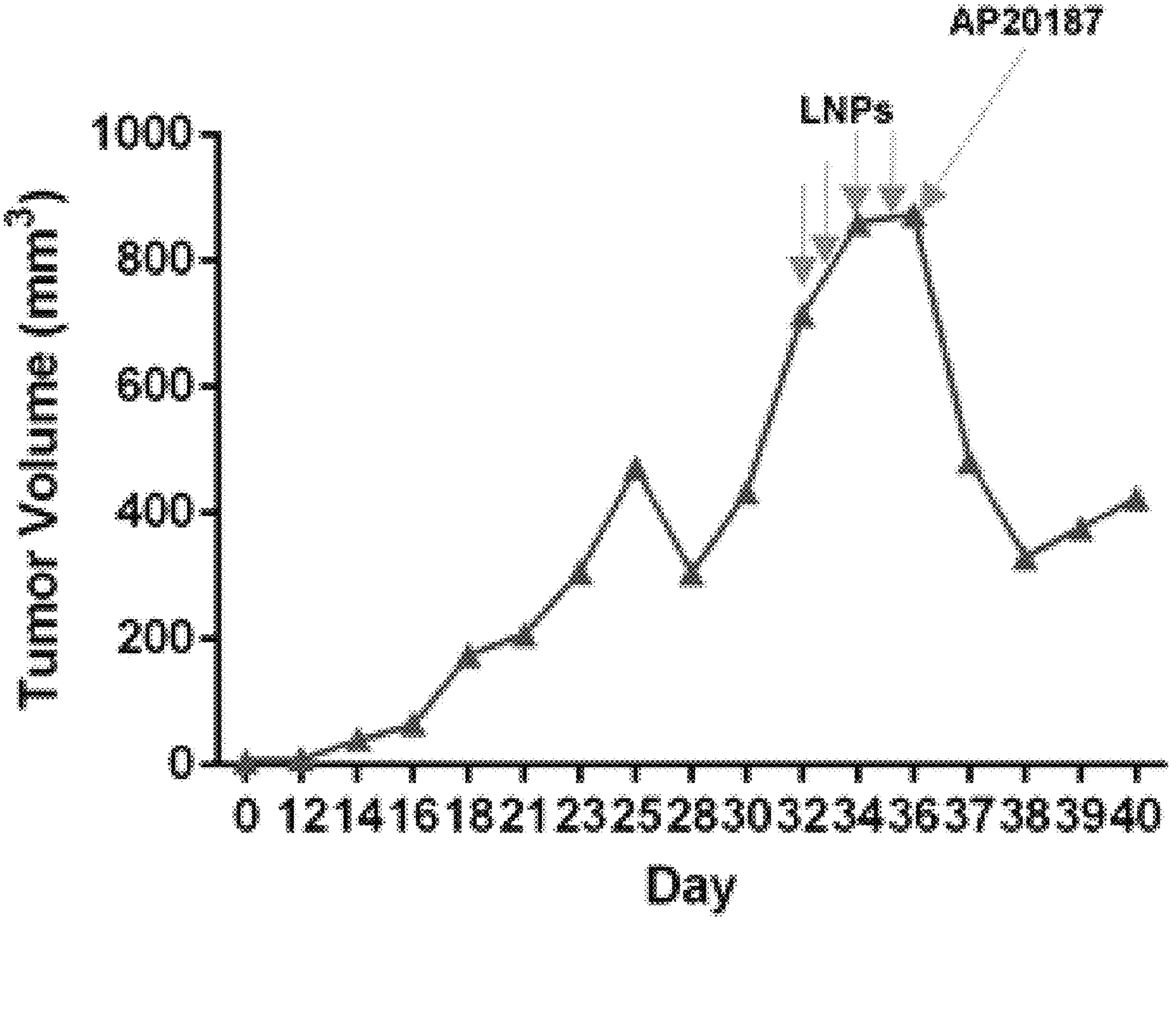
FIG. 44 is a graph from the second of four NSG mice bearing subcutaneous human prostate cancer PC-3 tumors that were injected intravenously (IV) with 4×100 μg doses of Fusogenix pVax-p53 formulation, followed 24 hours later by 2 mg/kg AP20187 IV.
Figure 45:
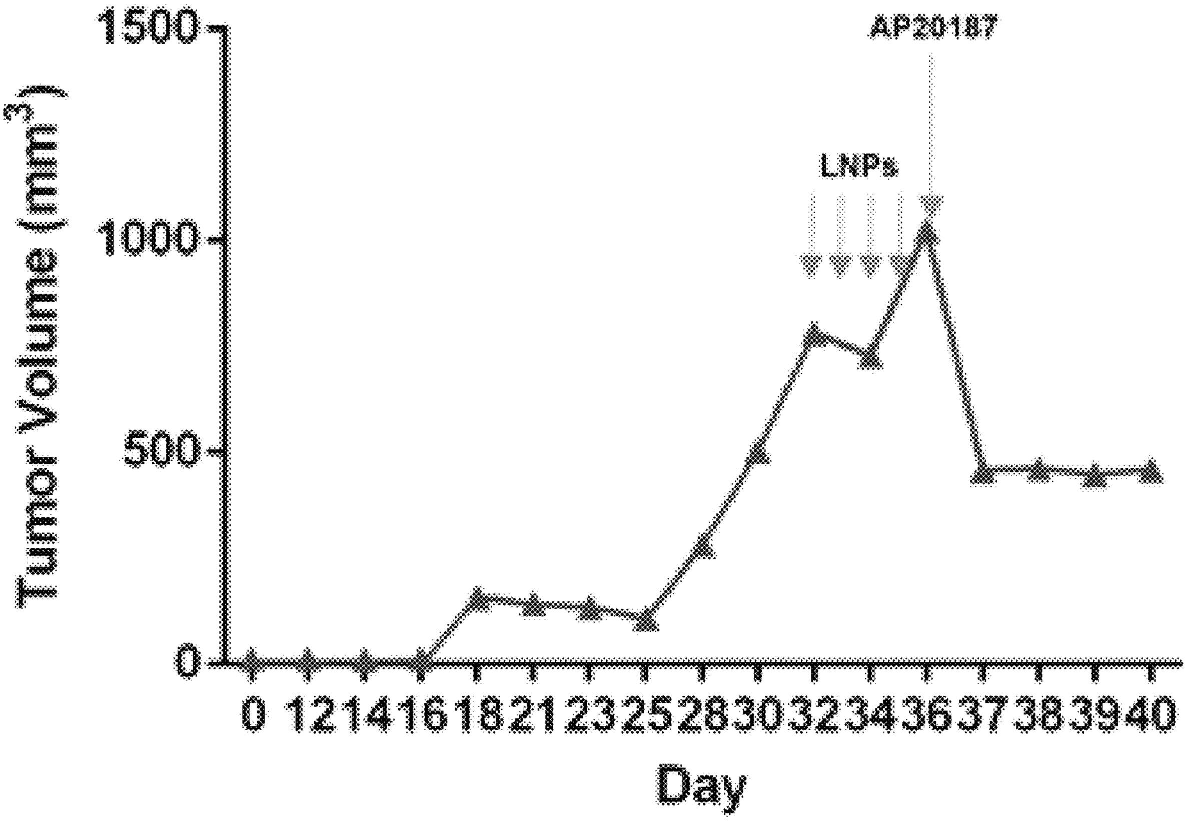
FIG. 45 is a graph from the third of four NSG mice bearing subcutaneous human prostate cancer PC-3 tumors that were injected intravenously (IV) with 4×100 μg doses of Fusogenix pVax-p53 formulation, followed 24 hours later by 2 mg/kg AP20187 IV.
Figure 46:
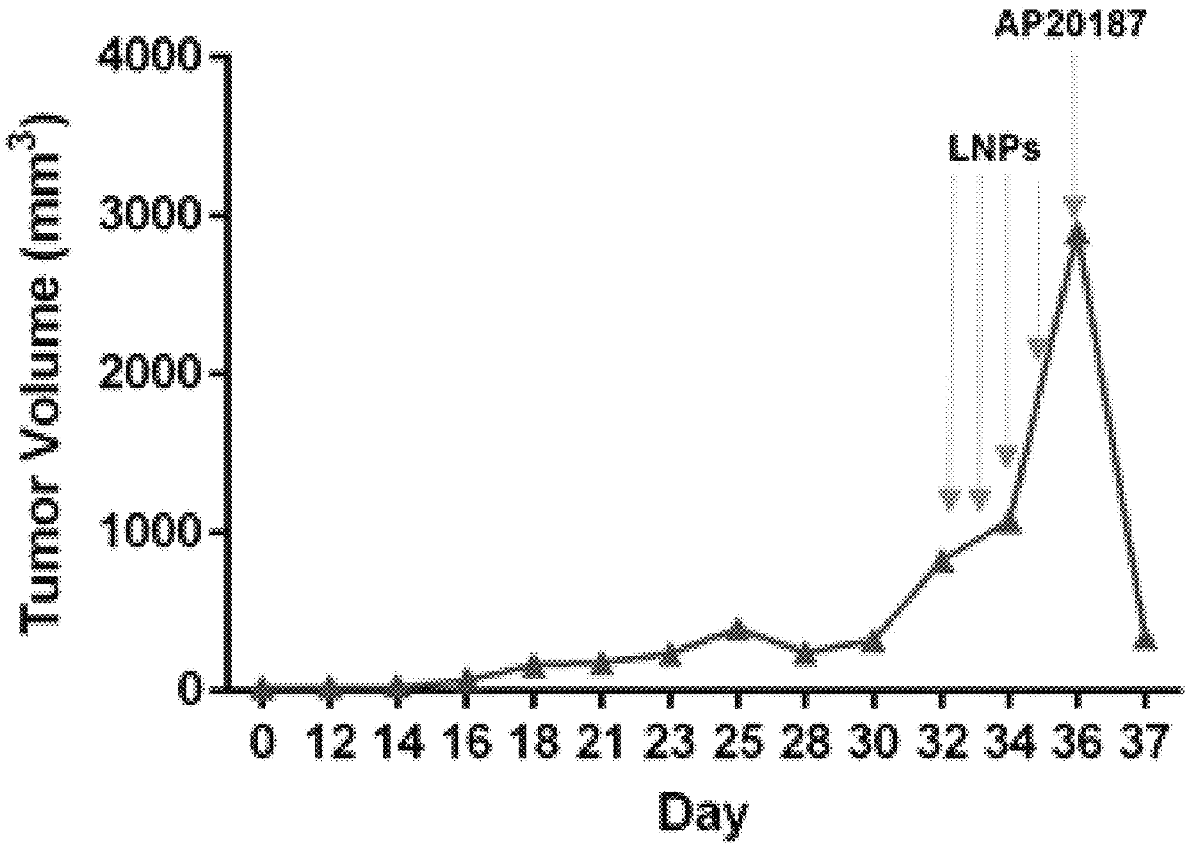
FIG. 46 is a graph from the fourth of four NSG mice bearing subcutaneous human prostate cancer PC-3 tumors that were injected intravenously (IV) with 4×100 μg doses of Fusogenix pVax-p53 formulation, followed 24 hours later by 2 mg/kg AP20187 IV.

A pre-clinical oncology study according to the present disclosure was conducted with 30×NSG mice implanted with human prostate tumor cells. FIG. 40. NSG mice bearing a subcutaneous human prostate PC-3 tumor were injected intratumorally (IT) with 100 μg Fusogenix pVax-p53 formulation, followed 96 hours later by intravenous (IV) administration of 2 mg/kg of the homodimerizer AP20187. FIG. 41. Tumors from the NSG mice bearing subcutaneous human prostate PC-3 tumors injected intratumorally with 100 μg Fusogenix pVax-p53 formulation, followed 96 hours by 2 mg/kg AP20187 IV, were photographed (FIGS. 42A-42C).

Four NSG mice bearing subcutaneous human prostate cancer PC-3 tumors that were injected intravenously (IV) with 4×100 μg doses of Fusogenix pVax-p53 formulation, followed 24 hours later by 2 mg/kg AP20187 IV. Tumor volume was measured and plotted as a function of time following IV injection. FIGS. 43-46.

Figure 47:
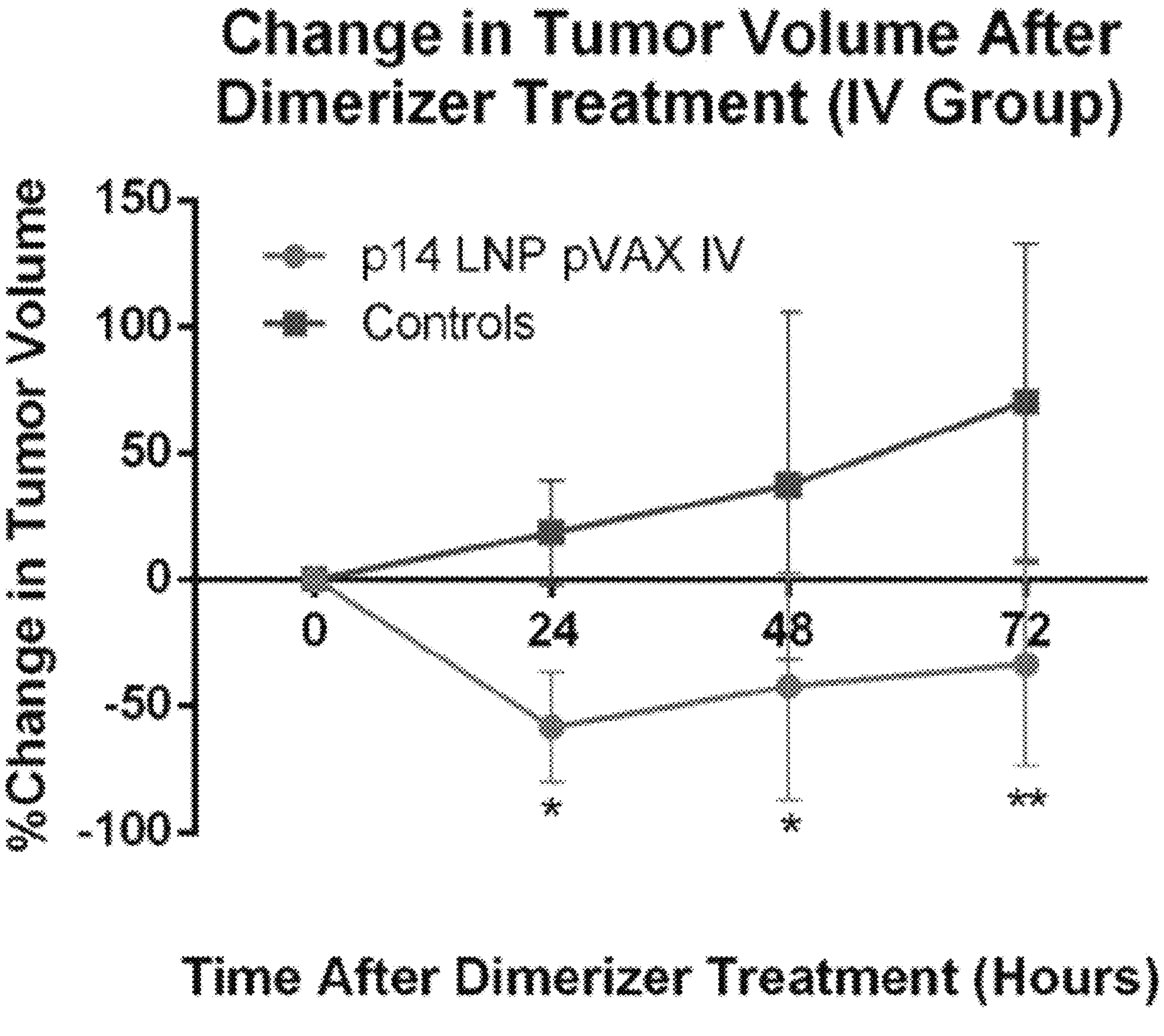
FIG. 47 is a graph showing the percentage change in tumor volume as a function of time after in vivo administration of a chemical inducer of dimerization (CID) in NSG mice (N=6 for all groups) bearing a prostate tumor that were treated with intravenous p14 LNP pVAX.
Figure 48:
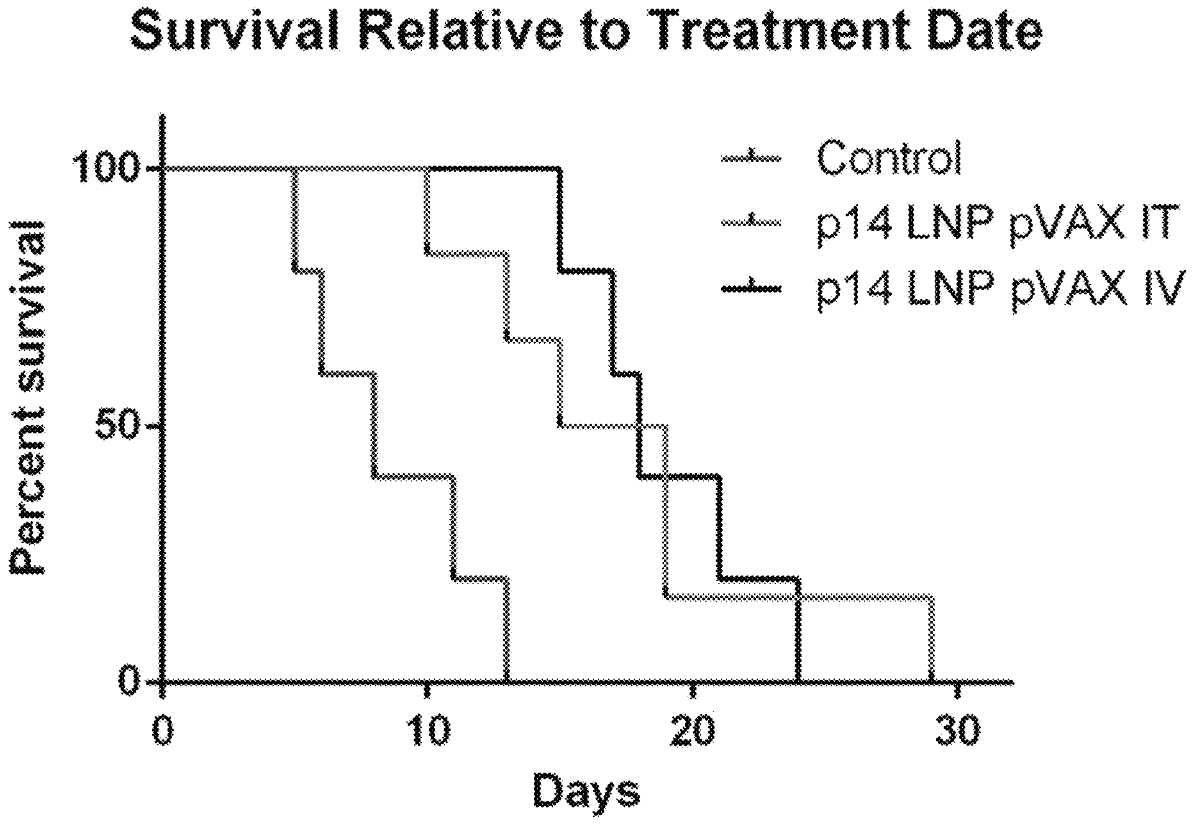
FIG. 48 is a survival curve showing the percent survival as a function of time after in vivo administration of a chemical inducer of dimerization (CID) in NSG mice (N=6 for all groups) bearing a prostate tumor that were treated with intravenous p14 LNP pVAX.

The percentage change in tumor volume was determined and plotted as a function of time after in vivo administration of a chemical inducer of dimerization (CID) in NSG mice (N=6 for all groups) bearing a prostate tumor that were treated with intravenous p14 LNP pVAX. FIG. 47. The percent survival was determined and plotted as a function of time after in vivo administration of a chemical inducer of dimerization (CID) in NSG mice (N=6 for all groups) bearing a prostate tumor that were treated with intravenous p14 LNP pVAX. FIG. 48.

Figure 49:
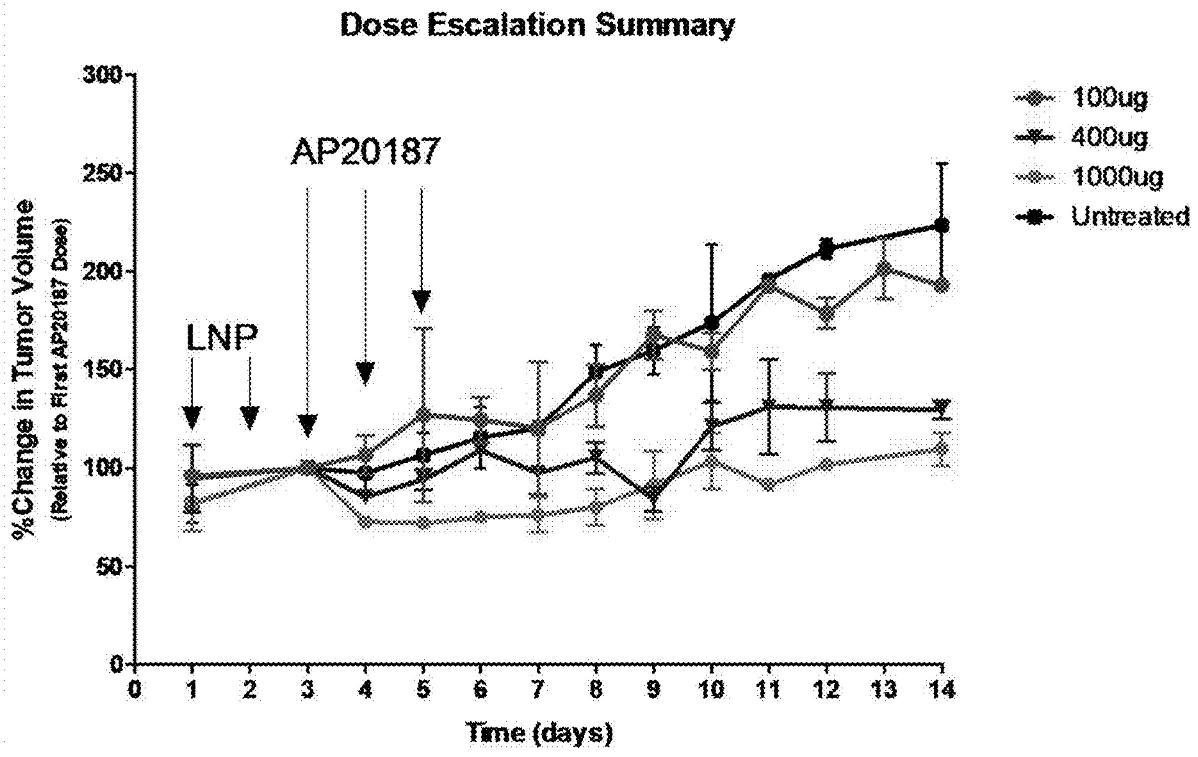
FIG. 49 is a graph of dose escalation data showing the percentage change in tumor volume as a function of time after in vivo administration of a chemical inducer of dimerization (CID) in NOD-SCID mice (N=6 for all groups) bearing a prostate tumor that were treated with 100 μg, 400 μg, and 1000 μg of intravenous p14 LNP pVAX. NOD-SCID mice were implanted subcutaneously with 500,000 PC-3 cells and randomized into treatment groups when their tumors reached 200 $mm^3$, (N=2 for all groups). Animals were injected with their assigned dose of p53-iCasp9 LNP IV twice followed by 2 mg/kg dimerizer. Tumors were measured directly every 24 hours.

A dose escalation study was carried out in which the percentage change in tumor volume as a function of time after in vivo administration of a chemical inducer of dimerization (CID) in NOD-SCID mice (N=6 for all groups) bearing a prostate tumor that were treated with 100 μg, 400 μg, and 1000 μg of intravenous p14 LNP pVAX. NOD-SCID mice were implanted subcutaneously with 500,000 PC-3 cells and randomized into treatment groups when their tumors reached 200 $mm^3$, (N=2 for all groups). Animals were injected with their assigned dose of p53-iCasp9 LNP IV twice followed by 2 mg/kg dimerizer. Tumors were measured directly every 24 hours. FIG. 49.

In total, the data presented herein demonstrate that apoptosis can be reliably induced in a p53+ prostate cancer cell-specific manner by the intravenous administration of fusogenic lipid nanoparticle formulations comprising a p53-iCasp9 expression construct.

Example 5

In Vivo Suppression of Metastases in NOD-SCID Mice Implanted with a Metastatic Tumor The suppression of metastatic tumor growth with repeat treatment of a p53-iCasp9 LNP with or without a chemical inducer of dimerization (CID) was demonstrated in a NOD-SCID mouse model system.

Figure 50:
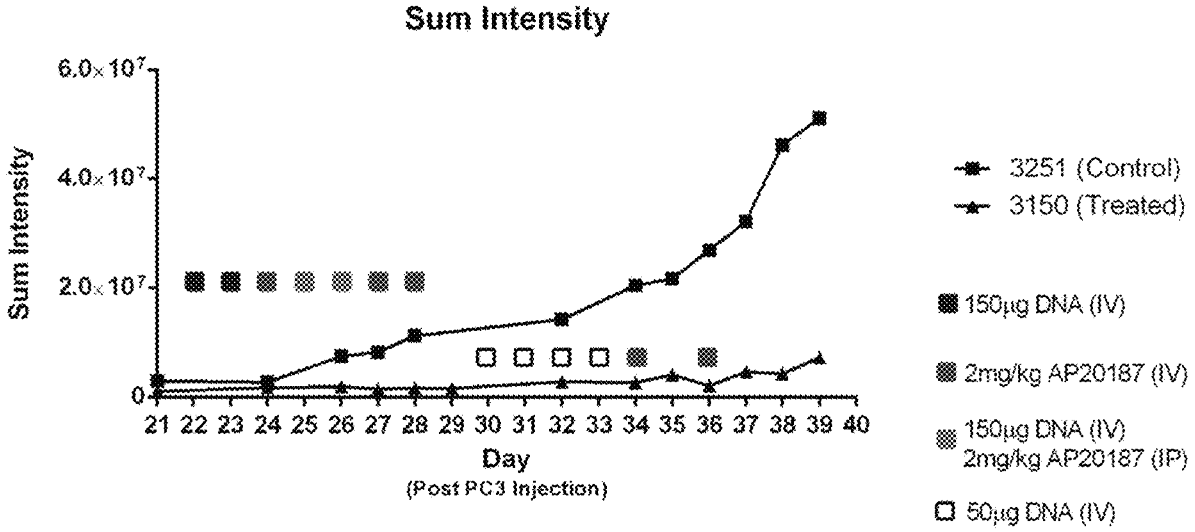
FIG. 50 is a graph showing the suppression of metastatic tumor growth with repeat treatment of a p53-iCasp9 LNP with or without a chemical inducer of dimerization (CID). NOD-SCID mice were injected with 500,000 PC-3M-luciferase cells on Day 0, LNP dosing was started on Day 22 with 150 μg p53-iCasp9 LNP. Dimerizer doses started Day 24 at 2 mg/kg. Mice were imaged every 24-48 hours to detect whole animal luminescence.

NOD-SCID mice were injected with 500,000 PC-3M-luciferase cells on Day 0, LNP dosing was started on Day 22 with 150 μg p53-iCasp9 LNP. Dimerizer doses started Day 24 at 2 mg/kg. Mice were imaged every 24-48 hours to detect whole animal luminescence. FIG. 50.

Example 6

In Vivo Suppression of Melanoma in Isogenic C57B6 Mice Implanted with B16 Murine Melanoma Cells Isogenic C57B6 mice implanted with B16 murine melanoma cells were treated with LNPs containing a construct encoding iCasp9 and murine CD40L under control of the murine p53 promoter followed by the AP20187 dimerizer.

Figure 51:
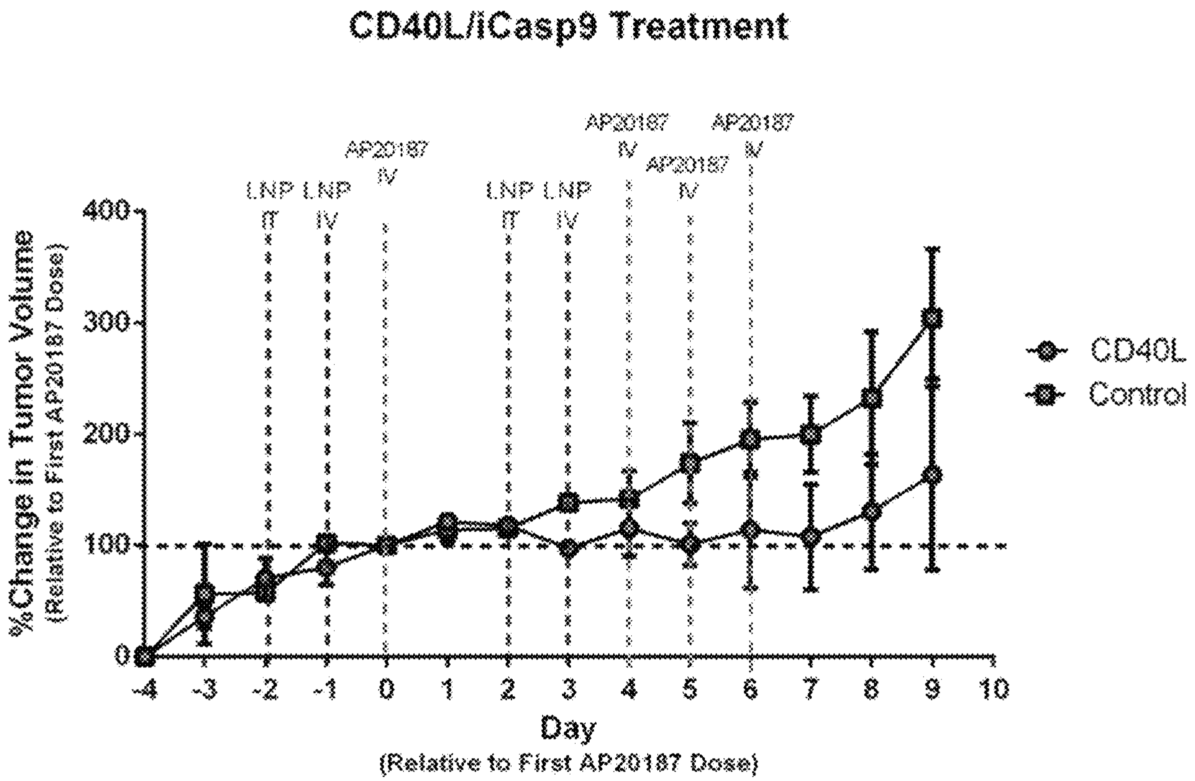
FIGS. 51 and 52 are graphs showing the percentage change in tumor volume (FIG. 51) and percent survival (FIG. 52) as a function of time after in vivo administration of a chemical inducer of dimerization (CID) in isogenic C57B6 mice implanted with B16 murine melanoma cells treated with LNPs containing a construct encoding iCasp9 and murine CD40L under control of the murine p53 promoter. Even though the rapid (10 hour) doubling time of the B16 cells made them largely refractory to the iCasp9-induced apoptosis, they still secreted enough CD40L to effectively halt the tumor's growth. A construct encoding GMCSF+OVA antigen was also tested and determined to be more effective than iCasp9 alone, but less effective than the CD40L version. N=3 for both groups.
Figure 52:
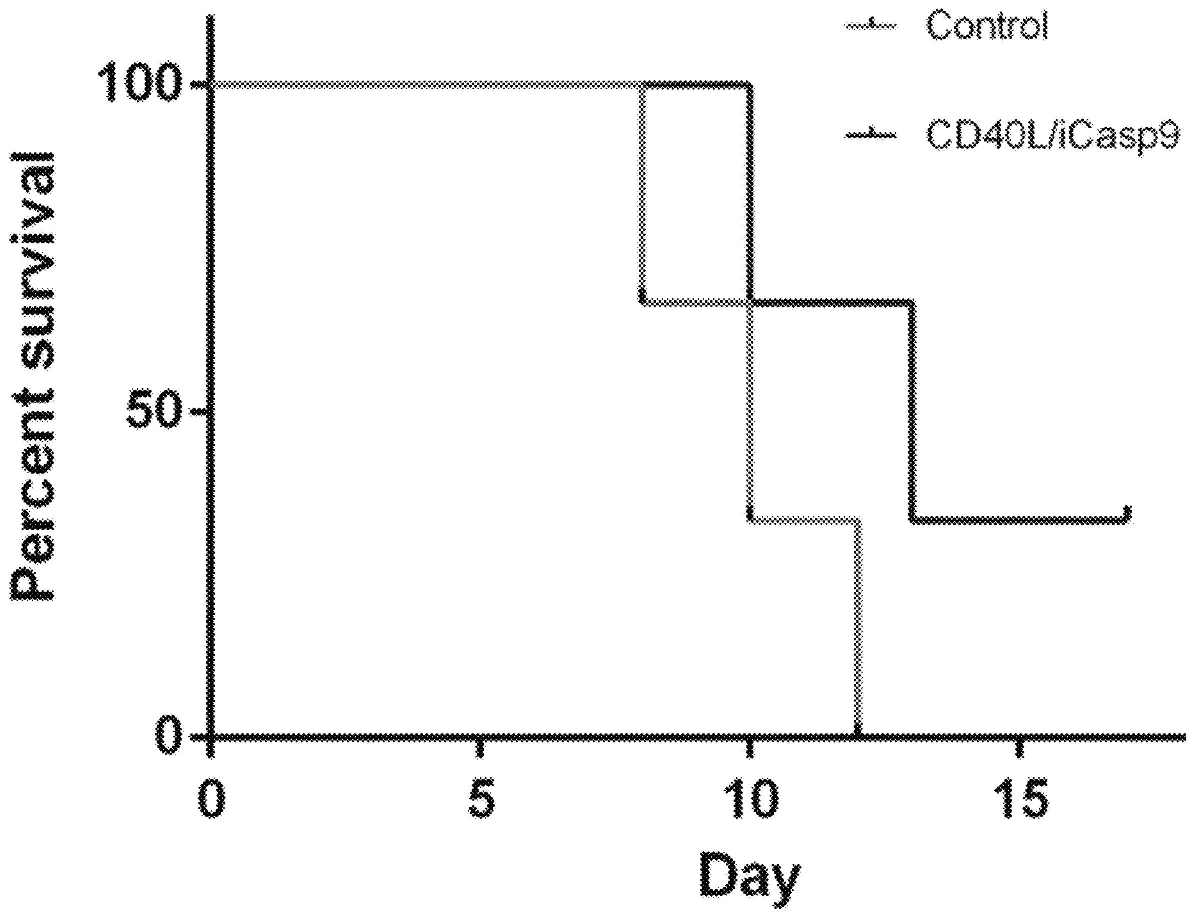

The percentage change in tumor volume (FIG. 51) and percent survival (FIG. 52) mas measured as a function of time after in vivo administration of a chemical inducer of dimerization (CID) in isogenic C57B6 mice implanted by subcutaneous injection with 250,000 B16 murine melanoma cells treated (grown to 400 $mm^3$) with LNPs containing a construct encoding iCasp9 and murine CD40L under control of the murine p53 promoter.

These data demonstrated that, even though the rapid (10 hour) doubling time of the B16 cells made them largely refractory to the iCasp9-induced apoptosis, they still secreted enough CD40L to effectively halt the tumor's growth. A construct encoding GMCSF+OVA antigen was also tested and determined to be more effective than iCasp9 alone, but less effective than the CD40L version. N=3 for both groups.

Example 7

In Vivo Suppression of Lung Cancer Metastasis in Mice Implanted with B16F10 Murine Melanoma Cells This Example demonstrates the in vivo p53+ target cell suppression murine p53+ B16F10 melanoma target cells implanted in a lung metastasis mouse model system.

Figure 53:
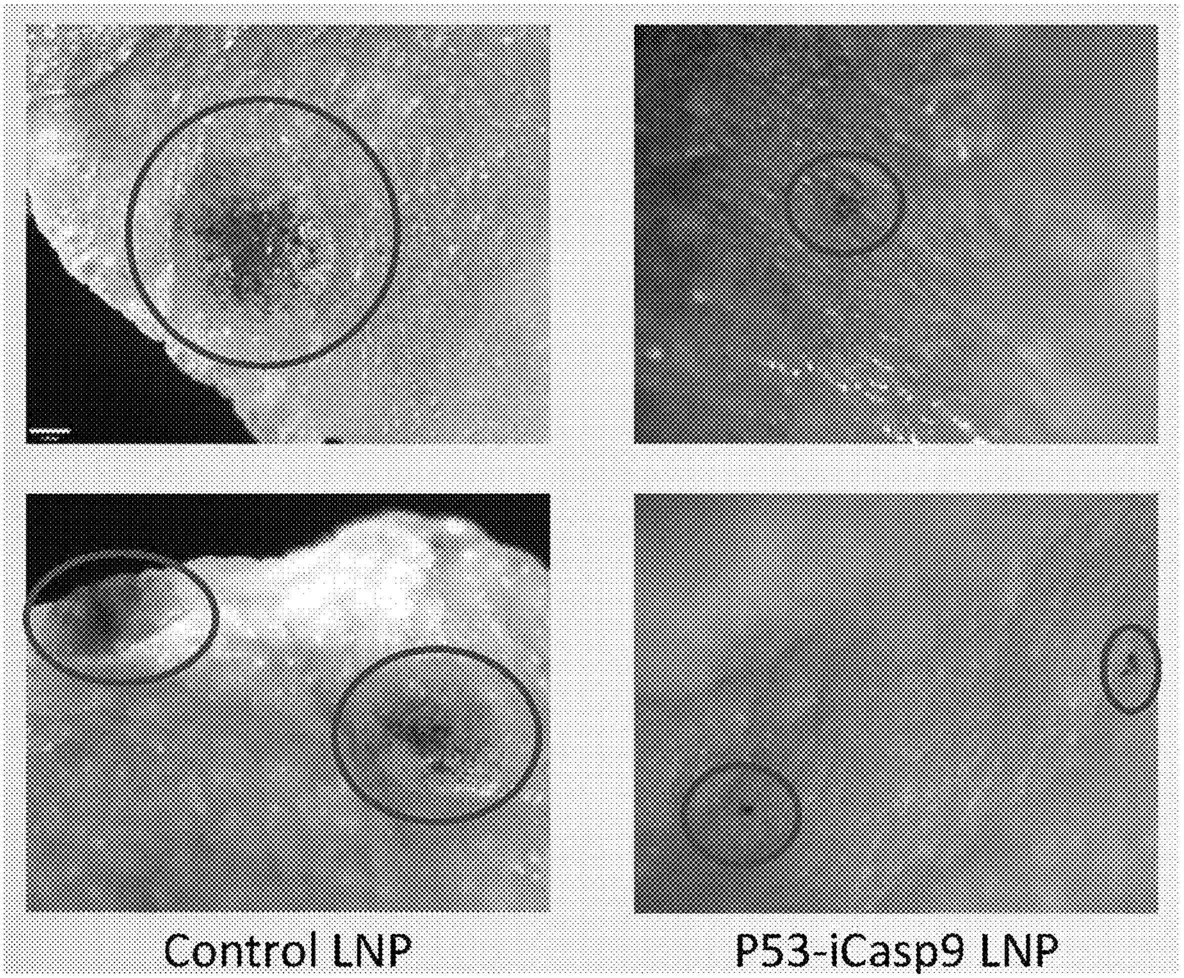
FIGS. 53 and 54 are photographs and a bar graph of a B15F10 lung metastasis model data in which 100 μg of a control LNP or a p53-iCasp9 LNP was administered intravenously at days 3, 6, 9, and 12 following the intravenous injection of 75,000 B16F10 cells. At days 5, 8, 11, and 13, a chemical inducer of dimerization (CID) was administered intraperitoneally. Animals were sacrificed at day 14 and lung metastases were quantified.
Figure 54:
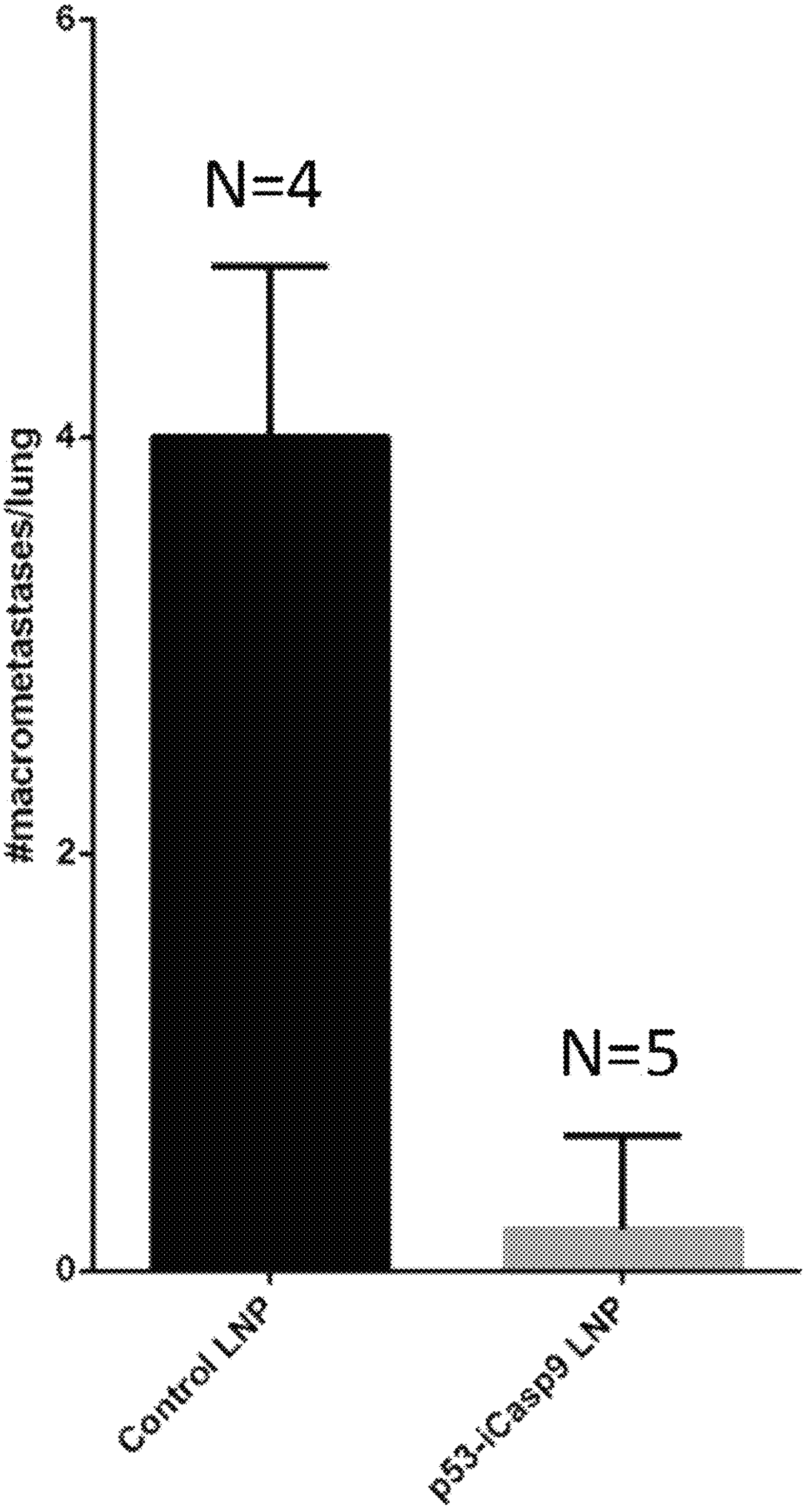

A B16F10 lung metastasis model system was employed in which 100 μg of a control LNP or a p53-iCasp9 LNP was administered intravenously at days 3, 6, 9, and 12 following the intravenous injection of 75,000 B16F10 cells. At days 5, 8, 11, and 13, a chemical inducer of dimerization (CID) was administered intraperitoneally. Animals were sacrificed at day 14 and lung metastases were quantified. FIGS. 53 and 54.

What is claimed is:

1. An expression construct for production of a therapeutic protein within a target cell, the expression construct comprising:

a) a p53 transcriptional promoter; and b) a heterologous nucleic acid that is under regulatory control of the p53 transcriptional promoter, wherein the heterologous nucleic acid encodes a therapeutic protein that reduces growth, survival, or a combination thereof, of the target cell.

2. A lipid-based nanoparticle (LNP) comprising the expression construct of claim 1.

3. The LNP of claim 2, wherein the LNP comprises a fusogenic peptide.

4. The LNP of claim 3, wherein the fusogenic peptide is a fusion-associated small transmembrane (FAST) protein.

5. The LNP of claim 3, wherein the fusogenic peptide comprises an ectodomain amino acid sequence from a first reovirus FAST protein and an endodomain amino acid sequence from a second reovirus FAST protein.

6. The LNP of claim 3, wherein the fusogenic peptide comprises an amino acid sequence with at least 80% sequence identity to an ectodomain of p14 FAST protein.

7. The LNP of claim 3, wherein the fusogenic peptide comprises an amino acid sequence with at least 80% sequence identity to an endodomain of p15 FAST protein.

8. The LNP of claim 2, wherein the LNP comprises an electroneutral lipid.

9. The LNP of claim 2, wherein the target cell is a mammalian target cell.

10. The LNP of claim 2, wherein the target cell is a human target cell.

11. The LNP of claim 2, wherein the target cell is a cancer cell.

12. The LNP of claim 11, wherein the target cell is a melanoma cell.

13. The LNP of claim 11, wherein the target cell is a brain cancer cell, a prostate cancer cell, a lung cancer cell, a colorectal cancer cell, a breast cancer cell, a liver cancer cell, a hematologic cancer cell, or a bone cancer cell.

14. The LNP of claim 2, wherein the target cell is a senescent cell.

15. The LNP of claim 14, wherein the target cell is a senescent kidney cell.

16. The LNP of claim 14, wherein the target cell is a spleen cell, a seminal vesicle cell, an inguinal fat cell, or a lung cell.

17. The LNP of claim 2, wherein the LNP is capable of delivering the expression construct to the target cell upon administration to a subject.

18. The expression construct of claim 1, wherein the therapeutic protein is a caspase, CASP3, CASP8, CASP9, BAX, DFF40, HSV-TK, cytosine deaminase, or an inducible variant thereof.

19. The expression construct of claim 1, wherein the therapeutic protein is an inducible CASP9.

20. The expression construct of claim 1, wherein the therapeutic protein is a non-inducible CASP9.

21. The expression construct of claim 1, wherein the therapeutic protein is a self-activating CASP9.

22. The expression construct of claim 1, wherein the heterologous nucleic acid further encodes an immunostimulatory protein or antigen.

23. The expression construct of claim 22, wherein the immunostimulatory protein or antigen is CD40L.

24. The expression construct of claim 22, wherein the immunostimulatory protein or antigen is a cytokine.

25. The expression construct of claim 22, wherein the immunostimulatory protein or antigen is GMCSF, IL12, OVA, Nt1, a tetanus antigen, or an influenza antigen.

26. A method of reducing growth or survival of a target cell, the method comprising contacting the target cell with the LNP of claim 2, thereby reducing growth or survival of the target cell.

27. A method of treating of a disease or condition in a subject in need thereof, the method comprising administering to the subject an effective amount of the LNP of claim 2.

* * * * *